United States Patent [19]
Dinsmore

[11] Patent Number: 6,140,116
[45] Date of Patent: Oct. 31, 2000

[54] ISOLATED AND MODIFIED PORCINE CEREBRAL CORTICAL CELLS

[75] Inventor: Jonathan Dinsmore, Brookline, Mass.

[73] Assignee: Diacrin, Inc., Charlestown, Mass.

[21] Appl. No.: 08/551,820

[22] Filed: Nov. 7, 1995

Related U.S. Application Data

[63] Continuation-in-part of application No. 08/424,856, Apr. 19, 1995, which is a continuation-in-part of application No. 08/336,856, Nov. 8, 1995, abandoned.

[51] Int. Cl.$^7$ ...................................................... C12N 5/00
[52] U.S. Cl. ......................... 435/325; 435/374; 424/93.7
[58] Field of Search ................................... 435/325, 374, 435/93.7

[56] References Cited

U.S. PATENT DOCUMENTS

| | | |
|---|---|---|
| 5,330,993 | 7/1994 | Armistead . |
| 5,411,883 | 5/1995 | Boss et al. . |
| 5,679,340 | 10/1997 | Chappel . |

FOREIGN PATENT DOCUMENTS

| | | |
|---|---|---|
| WO 91/09936 | 7/1991 | WIPO . |

OTHER PUBLICATIONS

Kopyov et al. Transplantation Procedings. vol. 24(2). pp. 547–548, Apr. 1992.
Freeman et al. Progree in Brain Research. 78. pp. 473–477, 1988.
Huffaker et al. Experimental Brain research. 77. pp. 329–336, 1989.
Garcia, A. et al. (1995) "Extensive Axonal and Glial Fiber Growth From Fetal Porcine Cortical Xenografts in the Adult Rat Cortex" *Cell Transplantation* 4(5): 515–527.
Hertel–Wulff, B. et al. (1994) "Long Term Survival of Pancreatic Islets in Diabetic Monkeys" *Cell Transplantation* 3(3): 216 (Abstract No. 20).
Akiyoshi, Donna E. et al. (1988) "Identification Of A Full–Length cDNA For An Endogenous Retrovirus of Miniature Swine" *Journal of Virology* vol. 72, No. 5, pp. 4503–4507.
Bakay, R.A.E. et al. (1985) "Preliminary Report on the Use of Fetal Tissue Transplantation to Correct MPTP–Induced Parkinson–Like Syndrome in Primates" *Appl. Neurophysiol.* 48:358–361.
Barinaga, Marcia (1994) "Neurotrophic Factors Enter the Clinic" *Science*, vol. 264, pp. 772–774.
Bjorklund, A. et al. (1982) "Cross–Specis Neutral Grafting In A Rat Model Of Parkinson's Disease" *Nature* 298: 652–654.
Björklund, A. et al. (1984) "Intracerebral Grafting of Neuronal Cell Suspensions I. Introduction and General Methods of Preparation" *Acta Physiol. Scand.* Suppl. 522:1–7.
Björklund, A. et al. (1984) "Intracerebral Grafting of Neuronal Cell Suspensions II. Survival and Growth of Nigral Cell Suspensions Implanted in Different Brain Sites" *Acta Physiol. Scand.* Suppl. 522:9–18.

Björklund, A. et al. (1984) "Intracerebral Grafting of Neuronal Cell Suspensions VI. Survival and Growth of Intrahippocampal Implants of Septal Cell Suspensions" *Acta Physiol. Scand.* Suppl. 522:49–58.
Björklund, A. et al. (1984) "Intracerebral Grafting of Neuronal Cell Suspensions VII. Recovery of Choline Acetyltransferase Activity and Acetylcholine Synthesis in the Denervated Hippocampus Reinnervated by Septal Suspension Implants" *Acta Physiol. Scand.* Suppl. 522:59–66.
Borlongan, Cesario V. et al. (1996) "Will Fetal Striatal Transplants correct The Akinetic End–Stage of Huntington's Disease" *Neurodegeneration*, vol. 5, No. 2, pp. 189–191.
Brownell, A.–L. et al. (1993) "In Vivo Visualization of Striatal Transplants in a Primate Model of Huntington's Disease (HD)" *Journal of Nuclear Medicine* 34(5):202P–203P, Abstract No. 960.
Chirgwin, John M. et al. (1979) "Isolation of Biologically Active Ribonucleic Acid From Sources" *Biochemistry*, vol. 18, No. 24, pp. 5294–5299.
Deacon, T.W. et al. (1993) "Target–Specific Long Distance Axon Growth From Porcine Striatal and Ventral Mesencephalon Xenografts in Rats" *Society for Neuroscience Abstracts* (24th Annual Meeting of The Society for Neuroscience, Nov. 7–12, 1993) 20(1–2):472, No. 205.9.
Deacon, T.W. et al. (1994) "Cytoarchitecture Development, Axon–Glia Relationships, and Long Distance Axon Growth of Porcine Striatal Xenografts in Rats" *Experimental Neurology* 130: 151–167 (1994).
Dunnett, S.B. et al. (1981) "Behavioural Recovery Following Transplantation of *Substantia nigra* in Rats Subjected to 6–OHDA Lesions of the Nigrostriatal Pathway. I. Unilateral Lesions" *Brain Research* 215:147–161.

(List continued on next page.)

*Primary Examiner*—Leon B. Lankford, Jr.
*Attorney, Agent, or Firm*—Lahive & Cockfield, LLP; Megan E. Williams; Amy E. Mandragouras, Esq.

[57] ABSTRACT

Porcine neural cells and methods for using the cells to treat neurological deficits due to neurodegeneration are described. The porcine neural cells are preferably embryonic mesencephalic, embryonic striatal cells, or embryonic cortical cells. The porcine neural cells can be modified to be suitable for transplantation into a xenogeneic subject, such as a human. For example, the porcine neural cells can be modified such that an antigen (e.g., an MHC class I antigen) on the cell surface which is capable of stimulating an immune response against the cell in a xenogeneic subject is altered (e.g., by contact with an anti-MHC class I antibody, or a fragment or derivative thereof) to inhibit rejection of the cell when introduced into the subject. In one embodiment, the porcine neural cells are obtained from a pig which is essentially free from organisms or substances which are capable of transmitting infection or disease to the recipient subject. The porcine neural cells of the present invention can be used to treat neurological deficits due to neurodegeneration in the brain of a xenogeneic subject (e.g., a human with epilepsy, head trauma, stroke, amyotrophic lateral sclerosis, Parkinson's disease, Alzheimer's disease, or Huntington's disease) by introducing the cells into the brain of the subject.

27 Claims, 21 Drawing Sheets

OTHER PUBLICATIONS

Dunnett, S.B. et al. (1984) "Intracerebral Grafting of Neuronal Cell Suspensions IV. Behavioural Recovery in Rats with Unilateral 6–OHDA Lesions Following Implantation of Nigral Cell Suspensions in Different Forebrain Sites" *Acta Physiol. Scand.* Suppl. 522:29–37.

Dunnett, S.B. et al. (1984) "Intracerebral Grafting of Neuronal Cell Suspensions V. Behavioural Recovery in Rats with Bilateral 6–OHDA Lesions Following Implantation of Nigral Cell Suspensions" *Acta Physiol. Scand.* Suppl. 522:39–47.

Fishman, J.A. (1994) "Miniature Swine As Organ Donors For Man: Strategies For Prevention of Xenotransplant–associated Infections" *Xenotransplantation*, vol. 1, pp. 47–57.

Gage, F.H. et al. (1984) "Intracerebral Grafting of Neuronal Cell Suspensions VIII. Survival and Growth of Implants of Nigral and Septal Cell Suspensions in Intact Brains of Aged Rats" *Acta Physiol. Scand.* Suppl. 522:67–75.

Gagnon Celine et al. (1993) "Grafts In The Treatment of Parkinson's Disease: Animal Models" *Reviews in Neurosciences*, vol. 4, pp. 17–40.

Grandin, Temple et al. (1988) "Perfusion Method For preparing Pig Brain Corte For Golgi–Cox Impregnation" *Stain Technology*, vol. 63, No. 3, ,pp. 177–181.

Gut, Stephan H. et al. (1989) "Solubilization and Characteriszation of the Cholecystokinin$_B$ Binding Site From Pig Cerebral Cortex" *European Journal Of Pharmacology*, Vol. 172, pp. 339–346.

Hantraye, P. et al. (1991) "Fetal Striatal Cross–Species Implants Ameliorate Abnormal Movements in a Primate Model of Huntington's Disease" *Society for Neuroscience Abstracts* 17:902, Abstract No. 359.3.

Hantraye, P. et al. (1992) "Intrastriatal Transplantation of Cross–Species Fetal Striatal Cells Reduces Abnormal Movements in a Primate Model of Huntington Disease" *PNAS USA* 89:4187–4191.

Helm, G.A. et al. (1991) "Fetal Striatal Allografts in the Rhesus Monkey: An Electron Microscopic Golgi Study" *Society for Neuroscience Abstracts* 17:902, Abstract No. 359.4.

Hirata, A.A. and P. I. Terasaki (1972) "Masking of Human Transplantation Antigens by Divers Substances" *Journal of Immunology* 108(6):1542–1550.

Isacson, O. et al. (1984) "Functional Neuronal Replacement by Grafted Striatal Neurones in the Ibotenic Acid–lesioned Rat Striatum" *Nature* 311:458–460.

Isacson, O. et al. (1985) "Neural Grafting in a Rat Model of Huntington's Disease: Progressive Neurochemical Changes After Neostriatal Ibotenate Lesions and Striatal Tissue Grafting" *Neuroscience* 16(4):799–817.

Isacson, O. et al. (1989) "A Primate Model of Huntington's Disease: Cross–species implantation of Striatal Precursor cells to the Excitotoxically Lesioned Baboon Caudate–Putamen" *Experimental Brain Research* 75:213–220.

Jackowski, Andre (1995) "Neural Injury Repair: Hope For The Future As Barriers To Effective CNS Regeneration Become Clearer" *British Journal Neurosurgery*, vol. 9, pp. 303–317.

Kopin, I.J. (1993) "Parkinson's Disease: Past, Present, and Future" *Neuropharmacol.* 9(1): 1–12.

Labandeira–Garcia, J.L. et al. (1991) "Development of Intrastriatal Striatal Grafts and Their Afferent Innervation From the Host" *Neuroscience* 42(2):407–426.

Lindvall, O. et al. (1994) "Evidence for Long–term Survival and Function of Dopaminergic Grafts In Progressive Parkinson's Disease" *Annals of Neurology* 35(2): 172–180.

Liu, F.–C. et al. (1993) "Intrastriatal Grafts Derived From Fetal Striatal Primordia—IV. Host and Donor Neurons Are Not Intermixed" *Neuroscience* 55(2):363–372.

Madrazo, I. et al. (1991) "Fetal Neural Grafting for the Treatment of Huntington's Disease (HD)—Report of the First Case" *Society for Neuroscience Abstracts* 17:902, Abstract No. 359.1.

Madrazo, Ignacio et al. (1990) "Fetal Homotransplants (Ventral Mesencephalon and Adrenal Tissue) To The Striatum of Parkinsonian Subjects" *Arch Neurol*, vol. 47, pp. 1281–1285.

Matsas, R. and Kenny, A.J. (1989) "Immunocytochemical Localization Of Endopeptidase–24.11 In Cultured Neurons From Pig Striatum" *Neuroscience*, vol. 31, No. 1, pp. 237–246.

McAllister II, J.P. et al. (1989) "Minimial Connectivity Between Six Month Neostriatal Transplants and the Host Substantia nigra" *Brain Research* 476:345–350.

Pakzaban, P. et al. (1993) "Increased Proportion of Acetylcholinesterase–rich zones and improved morphological integration in host striatum of fetal grafts derived from the lateral but not not the medial ganglionic eminence" *Experimental Brain Research* 97:13–22.

Pakzaban, P. et al. (1995) "A Novel Mode of Immunoprotection of Neural Xenotransplants: Masking of Donor Major Histocompatibility Complex Class I Enhances Transplant Survival in the Central Nervous System" *Neuroscience* 65(4): 983–996.

Peschanski, M. et al. (1995) "Rationale For Intrastriatal Grafting Of Striatal Neuroblasts In Patients With Huntington's Disease" *Neuroscience*, vol. 68, No. 2 pp. 273–285.

Pittius, c.W. et al. (1987) "Ontogenetic Development of Proenkephalin A And proenkephalin B Messenger RNA In Fetal Pigs" *Exp Brain Res*, vol. 69, pp. 208–212.

Pritzel, M. et al. (1986) "Afferent and efferent connections of striatal grafts implanted into the ibotenic acid lesioned neostriatum in adult rats" *Experimental Brain Research* 65:112–126.

Rutherford, A. et al. (1987) "Electrophysiological demonstration of host cortical inputs to striatal grafts" *Neuroscience Letters* 83:275–281.

Redmond, E.D. Jr. et al. (1993) "Neural Transplantation for Neurodegenerative Diseases: Past, Present, and Future" *Annals of the New York Academy of Sciences* 695: 258–266.

Schmidt, R.H. et al. (1984) "Intracerebral Grafting of Neuronal Cell Suspensions III. Activity of Intrastriatal Nigral Suspension Implants as Assessed by Measurements of Dopamine Synthesis and Metabolism" *Acta Physiol. Scand.* Suppl. 522:19–28.

Shrine, Jim (1994) "Regeneron Drops Phase III Of CNTF" *Bioworld Today*, vol. 5, No. 123 pp. 1–6.

Sloan, D.J. et al. (1991) "The Immune Response to Intracerebral neural Grafts" *TINS*, vol. 14, No. 8, pp. 341–346.

Smith, Douglas, M. (1993) "Endogenous Retroviruses In Xenografts" *New England Journal of Medicine*, vol. 19, pp. 142–143.

Spector, Dennis H. et al. (1983) "A Model Three–Dimensional Culture System For Mammalian Dopaminergic Precursor Cells: Application for Functional Intracerebral Transplantation" *Experimental Neurology*, vol. 124, pp. 253–264.

Van Roon, W.M.C. et al. (1995) "Fetal Porcine Ventral Mesencephalon Grafts: Dissection Procedure and Cellular Characterization In Culture" *Restorative Neurology and Neuroscience* 7(4): 199–205.

Walker, P.D. and J.P. McAllister II (1987) "Minimal connectivity between neostriatal transplants and the host brain" *Brain Research* 425:34–44.

Wictorin, K. and A. Björklund (1989) "Connectivity of Striatal Grafts Implanted into the Ibotenic Acid–lesioned Striatum—II. Cortical Afferents" *Neuroscience* 30(2):297–311.

Wictorin, K. et al. (1989) "Connectivity of Striatal Grafts Implanted into the Ibotenic Acid–lesioned Striatum—III. Efferent Projecting Graft Neurons and Their Relation to Host Afferents Within The Grafts" *Neuroscience* 30(2):313–330.

Wictorin, K. et al. (1991) "Long Axonal Growth in Adult Rat Striato–Nigro–Striatal System From Grafts of Human Neuroblasts" *Society for Neuroscience Abstracts* 17:902, Abstract No. 359.2.

Wictorin, K. et al. (1992) "Long Distance Directed Axonal Growth From Human Dopaminergic Mesencephalilc Neuroblasts Implanted Along the Nigrostriatal Pathway in 6–Hydroxydopamine Lesioned Adult Rats" *Journal of Comparative Neurology* 323: 475–494.

Wolff, J.A. et al. (1989) "Grafting Fibroblasts Genetically Modified To Produce L–dopa In A Rat Model of Parkinson Disease" *Proc. Natl. Acad. Sci.* USA 86: 9011–9014.

Xu, Z.C. et al. (1991) "Restoration of Thalamostriatal Projections in Rat Neostriatal Grafts: An Electron Microscopic Analysis" *Journal of Comparative Neurology* 303:22–34.

Yumoto, Noboru et al. (1986) "Solubilization and Characterization of Prostaglandin $E_2$ Binding Protein From Porcine Cerebral Cortex" *Journal of Neurochemistry* vol. 46, No. 1, pp. 125–132.

Zhou, F.C. and N. Buchwald (1989) "Connectivities of The Striatal Grafts In Adult Rat Brain: A Rich Afference And Scant Striatonigral Efference" *Brain Research* 504:15–30.

FIG. 1

| Pig number | Days gestation | Fetal CRL (mm) | Viability |
|---|---|---|---|
| 3 | 35 | 35 | < 10% |
| 5 | 27 | 22 | 73% |
| 6 | 32 | 30 | 20% |
| 9 | 26 | 18 | 81% |
| 14 | 28 | 25 | 76% |
| 15 | 26 | 20 | 85% |
| 20 | 28 | 25 | 77% |

FIG.2

DATA COMPARISON OF RATS WITH 6OHDA LESIONS AND SURVIVING PORCINE DOPAMINERGIC TRANSPLANTS

| RAT# | Imm.treat | Striatal graft location | # Dopamine cells | Initial rot. | Final rot. | Net rot. reduction |
|---|---|---|---|---|---|---|
| PRVM7-7 | Fab | dorsal-medial (+) | 468 | 939 | -10 | 979 |
| PRVM7-11 | Fab | medial (+) | 546 | 869 | -163 | 1032 |
| PRVM7-10 | Fab | lateral-ventral (+) | 1248 | 1089 | -51 | 1140 |
| PRVM7-5 | Fab | ventral (•) | 1476 | 1026 | 441 | 585 |
| PRVM6-16 | Cyclo | ventral,rostral,lateral (+) | 348 | 1005 | -28 | 1033 |
| PRVM1-3 | Cyclo | medial (+) | 364 | 314 | -149 | 463 |
| PRVM1-14 | Cyclo | central (+) | 472 | 389 | 2 | 387 |
| PRVM1-11 | Cyclo | medial-dorsal (+) | 488 | 1043 | 510 | 533 |
| PRVM5-13 | Cyclo | medial and ectopic (+) | 1938 | 1599 | 387 | 1212 |

Notes:
Transplanted rats (at least 11 weeks post-transplantation).
Included are all animals with more than 300 surviving dopaminergic cells present on histological examination.
Rats with fewer cells did not show rotational recovery.
(+) indicates dopamine terminals present in dorsolateral striatum.

FIG. 6A
FIG. 6B
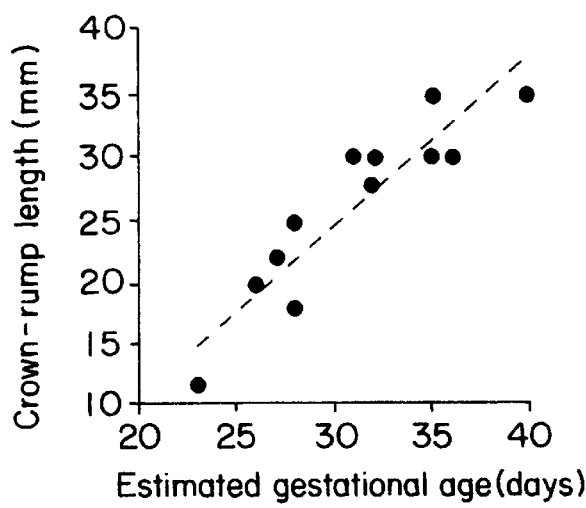
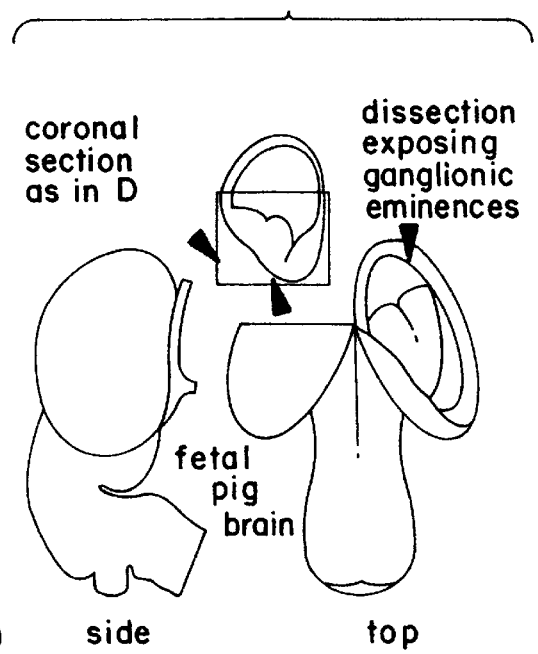
FIG. 7C
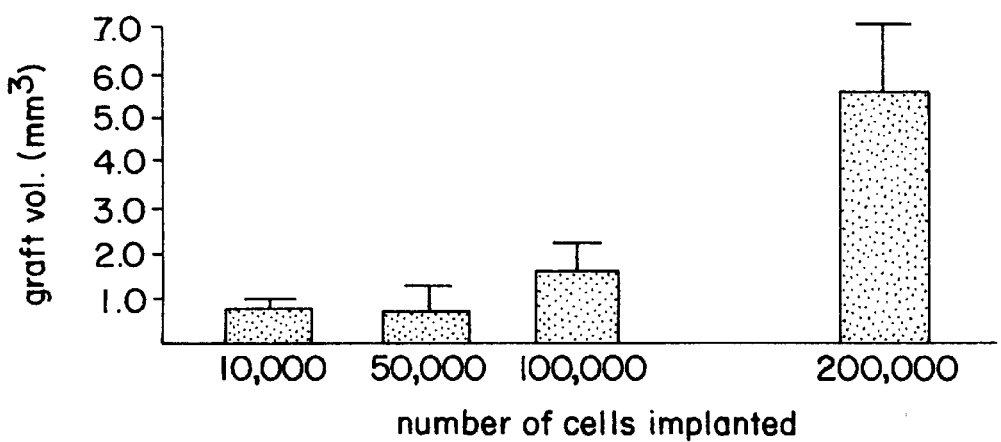

FIG.17A 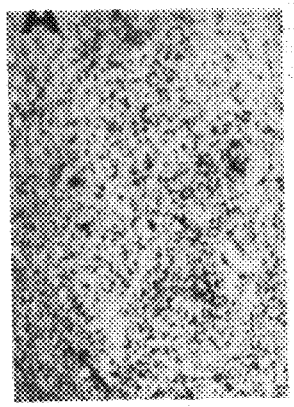 FIG.17B  FIG.17C 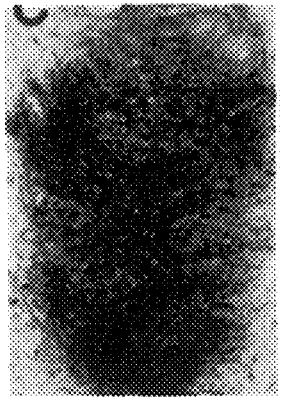 FIG.17D 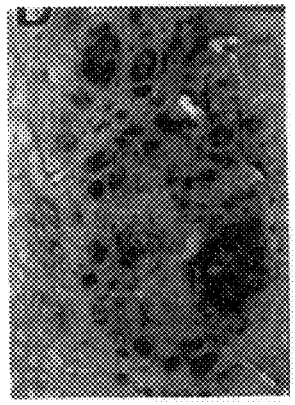
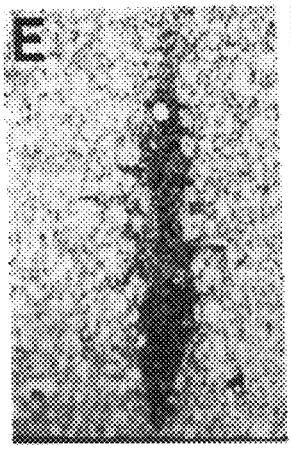 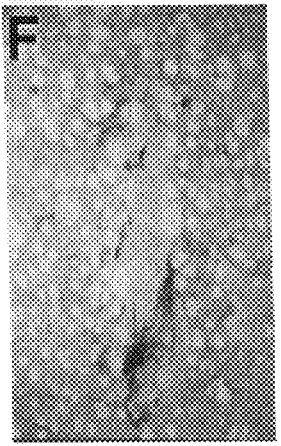 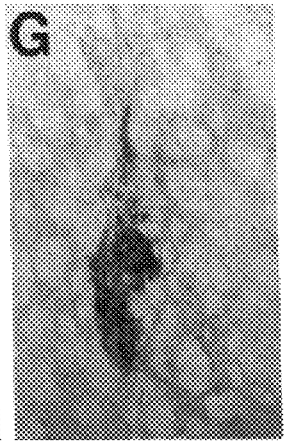 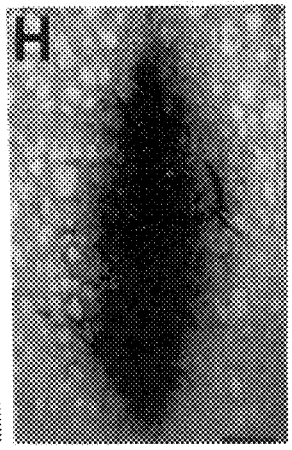
FIG.17E  FIG.17F  FIG.17G  FIG.17H

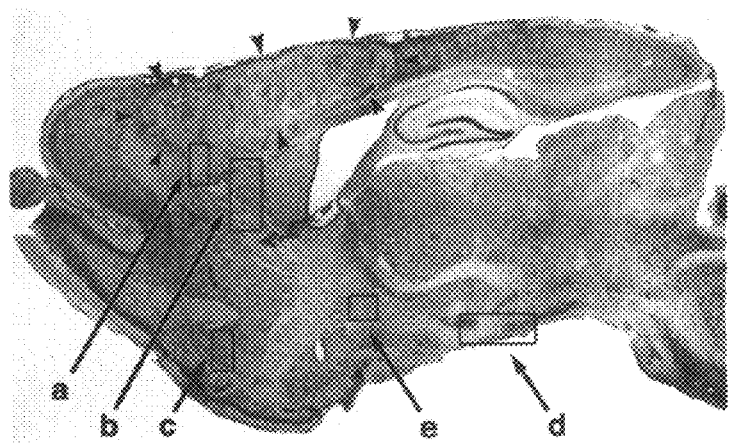
FIG.20A
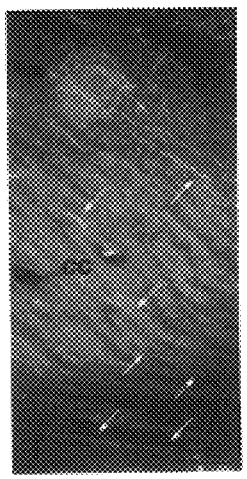 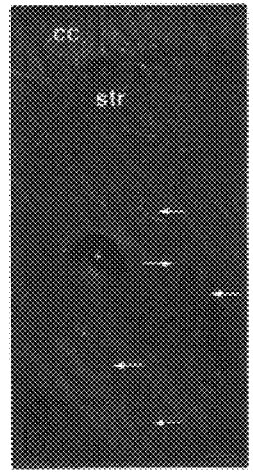 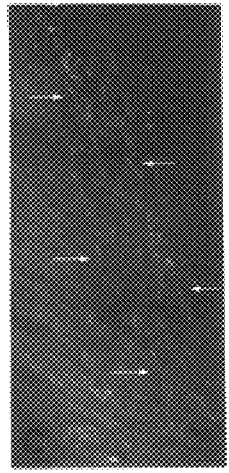
FIG.20B    FIG.20C    FIG.20D
 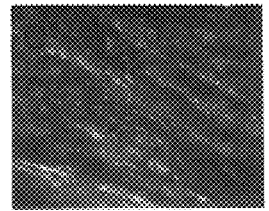
FIG.20E    FIG.20F

ISOLATED AND MODIFIED PORCINE CEREBRAL CORTICAL CELLS

RELATED APPLICATIONS

This application is a continuation-in-part application of U.S. Ser. No. 08/424,856, filed Apr. 19, 1995, which is a continuation-in-part application of U.S. Ser. No. 08/336,856, filed Nov. 8, 1994 now abandoned. The contents of these applications are hereby incorporated by reference.

BACKGROUND OF THE INVENTION

With the exception of L-DOPA pharmacological administration for Parkinson's disease, neurodegenerative diseases in general lack effective treatment. Previous studies of neurodegenerative diseases suggest that symptoms arise secondary to defects in local neural circuitry and cannot be treated effectively with systemic drug delivery. Consequently, alternative treatments for neurodegenerative diseases have emerged. Such treatments include transplantation of genetically engineered cells (See e.g., Breakefield, X. O. et al. (1989) Neurobiol. Aging 10:647–648; Gage, F. H. et al. (1987) Neuroscience 23:795–807; Horellou P. et al. (1990) Eur. J. Neurosci. 2:116–119; Rosenberg, M. B. et al. (1988) Science 242:1575–1578; Wolff, J. A. et al. (1989) Proc. Natl. Acad. Sci. USA 86:9011–9014) or fetal cells (See e.g., Björklund, A. et al. (1983) Acta. Physiol. Scand. Suppl. 522:1–75; Dunnett, S. B. et al. (1990) in Brain Repair (eds. Björklund, A. et al.) Wenner-Gren International Symposium Series 56:335–373 (McMillan Press, London); Isacson, O. et al. (1984) Nature 311;458–460) into the area of neurodegeneration in an effort to reconstitute damaged neural circuits, and to replace lost neurons and neurotransmitter systems.

Engineered cells can be derived from cell lines or grown from recipient host fibroblasts or other cells and then modified to produce and secrete substances following transplantation into a specific site in the brain. Neuroactive substances amenable to this delivery mode include neuropeptides and chemical transmitters. For example, one group of researchers developed a biological system in which genetically engineered nerve growth factor-producing rat fibroblasts, when implanted into the rat striatum prior to infusion of neurotoxins were reported to protect neurons from excitotoxin-induced lesions (Schumacher, J. M. et al. (1991) Neuroscience 45(3):561–570). Another group which transplanted rat fibroblasts genetically modified to produce L-DOPA or dopamine into 6-hydroxydopamine lesions of the nigrostriatal pathway in rats reported that the transplanted fibroblasts reduced behavioral abnormalities in the lesioned rats (Wolff, J. A. et al. (1989) Proc. Natl. Acad Sci. USA 86:9011–9014). Alternative to genetically engineered cells, cells to be implanted into the brain can be selected because of their intrinsic release of critical compounds, e.g., catecholamines by PC12 cells and nerve growth factor by immortalized hippocampal neurons.

Transplantation of cells engineered to produce and secrete neuroactive substances can be used alone or in combination with transplantation of fetal neural progenitor cells into areas of neurodegeneration in the brain. In order to repair functional connections damaged by neurodegeneration in, for example, the striatum, cells transplanted into the area of striatal neuron loss must re-establish synaptic connectivity with neurons in a number of target structures located a considerable distance from the area of neurodegeneration. Axonal tracing of connections of intrastriatal allografts in rats demonstrate that both afferent and efferent connections are established between graft neurons and host neurons in appropriate areas (Labandeira-Garcia, J. L. et al. (1991) Neuroscience 42:407–426; Liu, F. C. et al. (1990) J. Comp. Neurol. 295:1–14; Wictorin, K. et al. (1988) Neuroscience 27:547–562; Wictorin, K. et al. (1989) Neuroscience 30:297–311; Xu, Z. C. et al. (1991) J. Comp. Neurol. 303:22–34) and host-graft connections have been substantiated by electrophysiological and ultrastructural analysis. Rutherford, A. et al. (1987) Neuroscience Lett. 83:275–281; Xu, Z. C. et al. (1991) J. Comp. Neurol. 303:22–34. However, the extent of efferent connections from striatal allografts is limited, with respect to number of connections (Walker, P. D. et al. (1987) Brain Res. 425:34–44; Wictorin, K. et al. (1989) Neuroscience 30:297–311) and with respect to connections to distant targets (McAllister, J. et al. (1989) Brain Res. 476:345–350; Pritzel et al. (1986); Wictorin, K. et al. (1989) Neuroscience 30:297–311; Zhou, H. F. et al. (1989) Brain Res. 504:15–30). There is a need, therefore, for sources of neural progenitor cells and methods of neural transplantation which promote or enhance development of efferent connections from the transplant to the recipient brain tissue and connections with distant recipient brain targets.

In order to replace dopaminergic cells damaged by neurodegeneration in, for example, the substantia nigra, cells transplanted into the area of dopaminergic neuron loss must saturate the striatum with terminals and produce dopamine via a feedback control system. Cells which are engineered to express enzymes which act in the biosynthesis of dopamine are known to constitutively secrete dopamine. Kang, U. J. et al. (1993) J. Neurosci. 13(12):5203–5211. The constitutive secretion of dopamine was reported to be without significant storage capacity in vesicles or regulation at the level of secretion. Kang, U. J. et al. (1993) J. Neurosci. 13(12):5203–5211; See also Fisher, L. J. et al. (1993) Ann. N.Y. Acad. Sci. 695:278–284 (citing constitutive secretion of neurotransmitter as unaddressed issue). Thus, there is also a need for sources of neural progenitor cells which produce neurotransmitters via a feedback control mechanism.

SUMMARY OF THE INVENTION

The present invention is based, at least in part, on the discovery that porcine neural cells and, in particular, porcine embryonic neural cells isolated during certain stages of gestational development, when transplanted into the brain of a xenogeneic subject, promote the development of efferent connections between graft cells and distant brain targets in the host subject and receive afferent input from the host. Moreover, the porcine neural cells of the invention provide a source of neurotransmitters which are regulated by feedback control systems.

Accordingly, the instant invention pertains to a porcine neural cell or an isolated population of porcine neural cells suitable for transplantation into a xenogeneic subject, particularly a human subject. The porcine neural cell, in unmodified form, has at least one antigen on the cell surface which is capable of stimulating an immune response against the cell in a xenogeneic subject, for example, a human. The antigen on the surface of the porcine neural cell is altered to inhibit rejection of the cell when introduced into a xenogeneic subject. In one embodiment, the cell surface antigen which is altered is an MHC class I antigen. This MHC class I antigen can be contacted, prior to transplantation into a xenogeneic subject with at least one MHC class I antibody, or a fragment or derivative thereof, which binds to the MHC class I antigen on the cell surface but does not activate complement or induce lysis of the cell. One example of an MHC class I antibody is an MHC class I F(ab')$_2$ fragment, such as an MHC class I F(ab')$_2$ fragment of a monoclonal antibody PT85.

Particularly preferred porcine neural cells for use in treatment of human neurological deficits due to neurodegenerative diseases are mesencephalic, striatal, and cortical cells. Typically, these neural cells are obtained from embryonic pigs during selected stages of gestational development. For example, it has been determined that embryonic ventral mesencephalic cells obtained from an embryonic pig between about days 20 and 30, more preferably about days 24 and 30, and still more preferably about days 25 and 28, and yet more preferably about days 26 and 28, and most preferably about day 27 of gestation are suitable for transplantation into xenogeneic subjects, particularly human subjects. Similarly, it has been determined that porcine striatal cells obtained from an embryonic pig between about days 20 and 50, more preferably about days 30 to 40, and most preferably about days 31 and 38 are suitable for transplantation into xenogeneic subjects. In one embodiment, the striatal cells are obtained from a ganglionic eminence, e.g., a lateral ganglionic eminence, of porcine striatum, e.g., embryonic porcine striatum. It has also been determined that embryonic cortical cells obtained from an embryonic pig between about days 30 and 50, more preferably between about days 31 and 40 of gestation are suitable for transplantation into xenogeneic subjects. The population of porcine neural cells of this invention can include at least two different cell types selected from, for example, neural progenitor cells, glial progenitor cells, and glial cells. In addition, the neural cells of the invention can be grown as cell cultures. For example, the present invention includes a cell culture of porcine mesencephalic cells (e.g., ventral mesencephalic cells) wherein at least about 1% to 5% of the porcine mesencephalic cells produce tyrosine hydroxylase. Preferably at least about 10%, more preferably at least about 20%, yet more preferably at least about 30%, still more preferably at least about 40%, most preferably at least about 50% or more of the cells of the cell culture are porcine mesencephalic cells. Another aspect of the invention includes an isolated porcine mesencephalic cell (e.g., ventral mesencephalic cell) which, when transplanted into a xenogeneic subject, produces dopamine.

Another aspect of this invention pertains to an isolated population of porcine striatal cells. Preferred sources of such porcine striatal cells include embryonic porcine striatum, and, in particular, a ganglionic eminence, e.g., a lateral ganglionic eminence, of the striatum isolated at the above-described gestational ages. Similarly, the porcine striatal cells can be modified as described above. The isolated population of porcine striatal cells generally comprises neural progenitor cells but can comprise at least two different cell types selected from, for example, neural progenitor cells, glial progenitor cells, and glial cells. In one embodiment, the glial cells express a cell surface glycoprotein CD44. Such cells can be transplanted into a xenogeneic subject to enhance GABA-ergic transmission at a site of transplantation of the porcine striatal cells. Cell cultures comprising porcine striatal cells (e.g., embryonic porcine striatal cells, e.g., obtained from a lateral ganglionic eminence) wherein preferably at least about 10%, more preferably, at least about 20%, yet more preferably at least about 30%, still more preferably at least about 40%, most preferably at least about 50% or more of the cells of which are porcine striatal cells are also contemplated by the present invention. These cell cultures can also include glial cells, for example, at least about 10%, more preferably, at least about 20%, yet more preferably at least about 30%, still more preferably at least about 40%, most preferably at least about 50% or more glial cells. Another aspect of the invention includes an isolated porcine striatal cell which, upon transplantation into a xenogeneic subject, extends at least one neural process to at least one region of the brain of the subject. Preferred target regions of the subject include normal striatal cell efferent target regions of the brain, such as the substantia nigra and globus pallidus.

A further aspect of the invention pertains to an isolated population of porcine cortical cells. A preferred source of such porcine cortical cells includes embryonic porcine cortex. A preferred location from which the porcine cortical cells is isolated is the basal forebrain. These porcine cortical cells can be modified as described above. The porcine embryonic cortical cells are selected at gestational ages such that at least a portion of neural process outgrowth has begun. Preferably, the cells are selected such that both short and long distance neural process outgrowth has begun. The population of cortical cells can include at least two different cell types selected from, for example, neural progenitor cells, glial progenitor cells, and glial cells. Such cells can be transplanted into a xenogeneic subject to replace damaged or destroyed cortical cells. The transplanted cortical cells are capable of projecting target-specific axons throughout the brain. Cell cultures comprising porcine cortical cells (e.g., embryonic porcine cortical cells) wherein preferably at least about 10%, more preferably at least about 20%, yet more preferably at least about 30%, still more preferably at least about 40%, most preferably at least about 50% or more of the cells of which have at least one neural process are also contemplated by the present invention. A further aspect of the invention includes an isolated porcine cortical cell which, upon transplantation into a xenogeneic subject, extends at least one neural process to at least one cortical or subcortical target region in the brain of the subject. Typical cortical cell efferent target regions of the brain include neocortex, hippocampus, corpus callosum, cingulum bundle, internal capsule, and cerebral peduncle.

A still further aspect of the invention pertains to a porcine neural cell or a population of neural cells isolated from a pig which is essentially free from organisms which are capable of transmitting infection or disease to a xenogeneic recipient, e.g., a human, of the cells.

Categories of pathogens from which the swine are free can include parasites, bacteria, mycoplasma, and viruses. In one embodiment, the pig from which the neural cells are isolated is free of one or more of the following organisms: Toxoplasma, eperythrozoon, brucella, listeria, mycobacterium TB, leptospirillum, haemophilus suis, M. Hyopneumonia, porcine respiratory reproductive syndrome, rabies, pseudorabies, parvovirus, encephalomyocarditus virus, swine vesicular disease, techen (Porcine polio virus), hemagglutinating encephalomyocarditus, suipoxvirus, swine influenza type A, adenovirus, transmissible gastroenteritis virus, bovine viral diarrhea, and vesicular stomatitis virus. The cells can be modified as described above to inhibit rejection of the cell upon introduction into a xenogeneic subject. The porcine neural cells of the invention can be grown as a cell culture in a medium suitable to support the growth of the cells. Such cell cultures can also include at least one agent or factor selected from the group consisting of an angiogenic factor, a neurotrophic factor, an antiapoptotic factor, an antioxidant, and an agent which inhibits nitric oxide production. Examples of angiogenic factors include vascular endothelial growth factor, platelet-derived growth factor, fibroblast growth factor, and epidermal growth factor.

Examples of neurotrophic factors include glial cell line-derived growth factor, brain-derived neurotrophic factor, ciliary neurotrophic factor, midkine, insulin-like growth factor I and II, insulin, fibroblast growth factor, neurotrophin-3, neurotrophin 4/5, transforming growth factor β, FK506, and cyclosporine A. Examples of antiapoptotic factors include the bcl-2 gene product, the bcl-xL gene product, the bcl-Xβ gene product, the crmA gene product, nerve growth factor, platelet-derived growth factor, superoxide dismutase, catalase, and N-acetyl cysteine. Antioxidants which can be added to the cell culture include superoxide dismutase, glutathione peroxidase, N-acetyl cysteine, a lazaroid, vitamin C, vitamin E, and beta carotene. Examples of agents which inhibit nitric oxide production include gangliosides, FK506, cyclosporine A, and superoxide dismutase. In addition, the porcine neural cells can be inserted into a delivery device, e.g., a syringe, which facilitates the introduction of the cells into a subject. Preferred neural cell types, cell ages, and cells sources are described above. Methods for isolating porcine neural cells from such a pig, in which the pig is tested for the presence or absence of organisms which are capable of transmitting infection or disease to a recipient of the cells, and neural cells isolated, are also within the scope of this invention. Additionally, methods for treating neurodegeneration in the brain of a subject, e.g., a human, by introducing porcine neural cells isolated from such a pig into the subject are contemplated by the present invention.

This invention also provides methods for treating neurological deficits due to neurodegeneration in the brain of a xenogeneic subject by transplantation of the porcine neural cells of the invention, e.g., modified or unmodified porcine neural cells, into an area of neurodegeneration, e.g., striatum, in the brain of the subject, e.g., a human with Huntington's disease. Transplantation of the porcine neural cells can be accompanied by administration of least one agent or factor selected from the group consisting of an angiogenic factor, a neurotrophic factor, an antiapoptotic factor, an antioxidant, and an agent which inhibits nitric oxide production as described herein as well as an immunosuppressive agent, e.g., cyclosporine A, FK506, RS-61443, or a T cell antibody, to the subject.

In one embodiment, neurological deficits due to neurodegeneration in the brain of a xenogeneic subject are treated by transplantation of porcine striatal cells (e.g., embryonic porcine striatal cells such as striatal cells obtained from a ganglionic eminence, e.g., a lateral ganglionic eminence, of porcine striatum) into an area of neurodegeneration in the brain of the subject. The method can be used to treat neurodegeneration in the basal ganglia, and in particular, neurodegeneration in the striatum of a subject, such as a human with Huntington's disease. It is preferred that porcine striatal cells obtained from the lateral ganglionic eminence of embryonic porcine striatum (e.g., embryonic days 20 to 50, more preferably about embryonic days 30 to 40, and most preferably about embryonic days 31 to 38) are transplanted into the site of neurodegeneration. The neural cells of the invention can also be used to treat epilepsy. For example, GABA-ergic neural cells such as striatal cells or cortical cells of the invention can be transplanted into the brain, e.g., in an area of neurodegeneration or epileptic focus, of a subject with epilepsy, such as can occur, for example, in the hippocampus, e.g., the CA1 region of the hippocampus, the entorhinal cortex, or the substantia nigra.

In another embodiment, neurological deficits due to neurodegeneration in the brain of a xenogeneic subject are treated by transplantation of porcine mesencephalic cells of the invention into the area of neurodegeneration in the brain of the subject. The method can be used to treat neurodegeneration in mesencephalon, and in particular, neurodegeneration in the mesencephalon of a subject, such as a human with Parkinson's disease. It is preferred that the porcine mesencephalic cells be embryonic ventral mesencephalic cells obtained from the ventral mesencephalon of an embryonic pig between about days 20 and 30, more preferably about days 24 and 30, still more preferably about days 25 and 28, and yet more preferably about days 26 and 28, and most preferably about day 27 of gestation. Such cells can be transplanted into the site of neurodegeneration in the brain of the xenogeneic subject.

In yet another embodiment, neurological deficits due to neurodegeneration in the brain of a xenogeneic subject are treated by transplantation of porcine cortical cells of the invention into the area of neurodegeneration in the brain of the subject. The method can be used to treat neurodegeneration in the cortex, and in particular, neurodegeneration in the cortex of a subject, e.g., a human with a disorder such as stroke, head trauma, amyotrophic lateral sclerosis, multiple sclerosis, Huntington's disease, and Alzheimer's disease. It is preferred that the porcine cortical cells be embryonic cortical cells obtained from the cortex of an embryonic pig between about days 25 and 50 and more preferably about days 28 and 40 of gestation. Such cells can be transplanted into the site of neurodegeneration in the brain of the xenogeneic subject.

The invention also features a method for isolating cells from a lateral ganglionic eminence of fetal porcine striatum. This method includes dissecting a lateral ganglionic eminence from a medial ganglionic eminence of the striatum of a embryonic pig between about thirty to forty days of gestational age.

BRIEF DESCRIPTION OF THE DRAWINGS

FIG. 1 shows results of cell viability tests after isolation of ventral mesencephalic (VM) cells from embryonic pigs of different ages.

FIG. 2 shows the results of histological analysis and behavioral tests performed on rats containing embryonic pig mesencephalic grafts introduced into 6-hydroxydopamine lesioned animals. The grafts were shown to contain large numbers of dopamine neurons (the neurons required to treat Parkinson's disease) and to correct behavioral deficits in the rats. The method used to analyze the behavior of the rats receiving the grafts is described below under the heading "Method for Treating Neurological Deficits due to Neurodegeneration in the Brain of a Xenogeneic Subject Using Porcine Neural Cells Obtained from an Essentially Pathogen-Free Swine".

FIG. 5A shows the graft stained for the neural marker neurofilament 70 kD. FIGS. 5B and 5C show the graft stained for glial elements with anti-MHC-I and anti-CD44, respectively.

FIGS. 6A–6D depict fetal pig donor characteristics and dissection protocol. FIG. 6A is a graph showing the relationship between crown-to-rump-length and estimated gestational age of pig fetuses recorded during the course of the studies described herein (including those not transplanted). FIG. 6B is a schematic drawing of an E35 fetal pig brain showing the position of the ganglionic eminences within the telencephalic vesicles. FIGS. 6C and 6D are coronal sections of an E35 fetal pig brain showing two levels through the ganglionic eminences. The sulcus separating the lateral ganglionic eminence (LGE) from the medial ganglionic eminence (MGE) is clearly evident in the more anterior section (FIG. 6C) and becomes a shallow depression more posteriorly (FIG. 6D). M=medial ganglionic eminence; L=lateral ganglionic eminence. Scale bar=200 µm.

FIGS. 7A–7C depict a summary of a dose/response experiment to determine the relationship between numbers of viable fetal porcine cells transplanted and the subsequent volume of the resulting 8 week old striatal xenografts as measured from AChE-stained sections. FIG. 7A shows two grafts in a 100,000/50,000 cell comparison. FIG. 7B depicts two grafts in a 200,000/10,000 cell comparison. FIG. 7C depicts the dose-response relationship between number of implanted fetal pig LGE cells and the volume of the xenograft after 2 months. Scale bar=200 µm.

FIG. 14A depicts cyclosporine A (CyA) treated rats and (n=11) and FIG. 14B depicts non-CyA treated rats (n=11).

FIGS. 17A–17H depicts photographs of adjacent coronal sections through a representative porcine mesencephalic graft of a CyA treated rat (FIGS. 17A–17D) and non-CyA treated rat (FIGS. 17E–17H) stained for Nissl (FIGS. 17A and 17E), NF70 (FIGS. 17B and 17F), and CD44 (FIGS. 17D and 17H). Scale bar=200 µm.

FIGS. 20A–20F are photographs showing axonal and glial fiber outgrowth from porcine cortical xenografts.

DETAILED DESCRIPTION OF THE INVENTION

Figure 3:
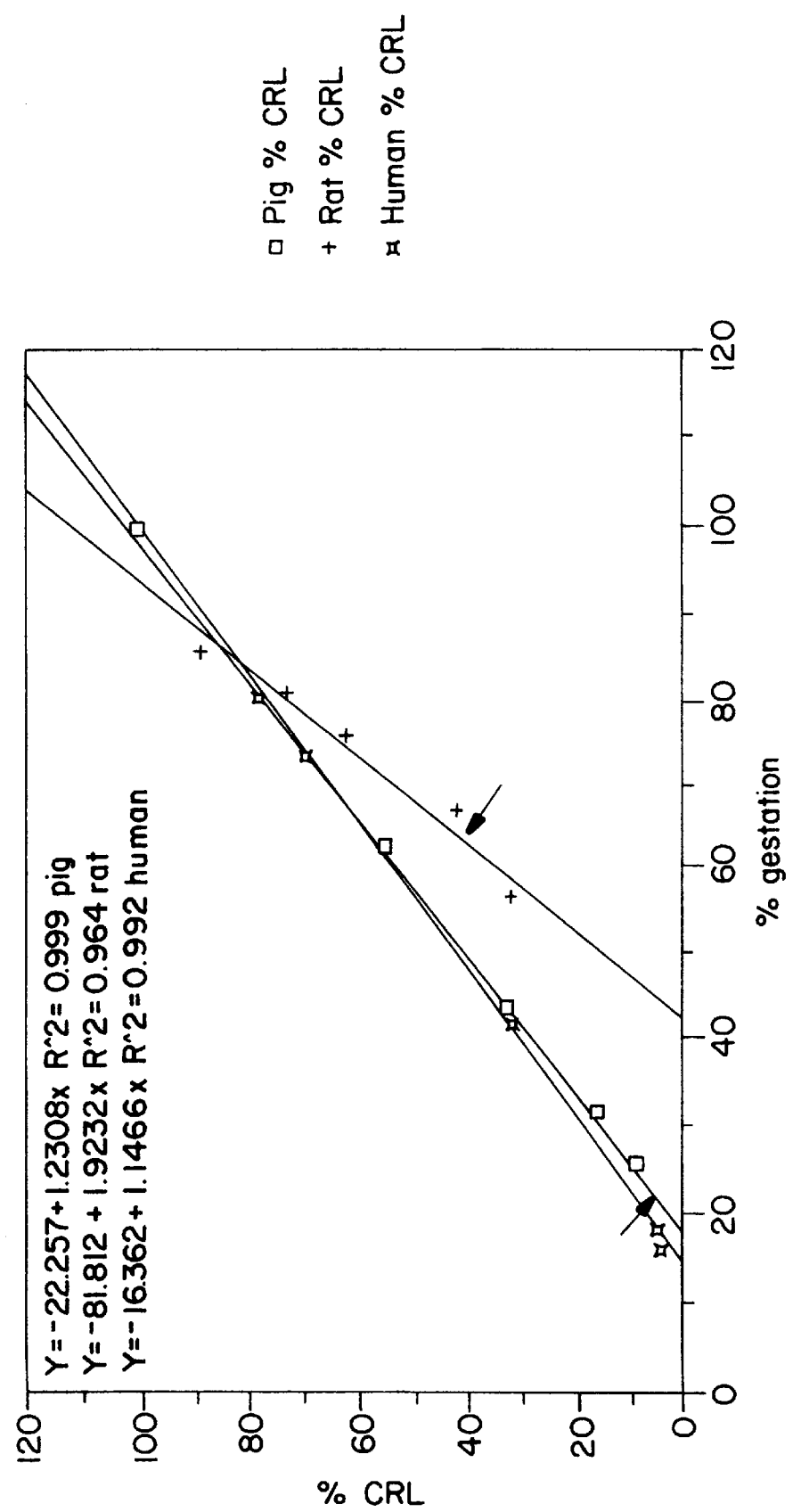
FIG. 3 is a graph depicting a comparison of pig, rat, and human embryonic development. Data for pig, rat, and human crown-to-rump length (CRL) vs. gestational age have been plotted. These have been expressed as % of total CRL at birth and % total gestation so that they can be plotted on the same graph. The gestation time for the pig, rat and human are 115, 21 and 266 days, respectively. The arrows mark the gestational ages in the pig, rat, and human that are optimal for neural cell harvest for Huntington's disease.
Figure 4A:
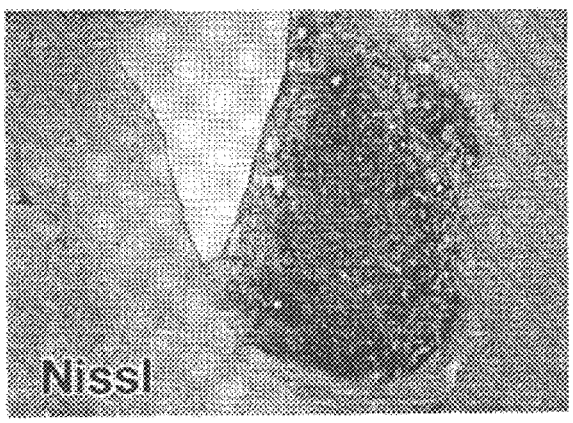
FIGS. 4A–4E depict a representative graft derived from E50 (50 day old) pig fetuses showing few neural components. This is a representative graft derived from 50 day old donor fetuses stained for cell content (Nissl, FIG. 4A), neural elements (AChE, FIG. 4B, and TH, FIG. 4E), and glial elements (GFAP, FIG. 4C, and CD44, FIG. 4D). Nissl stain identifies the boundaries of the graft and one can see by comparison of glial and neural cell staining that the grafts have a reduced amount of neural staining.
Figure 4B:
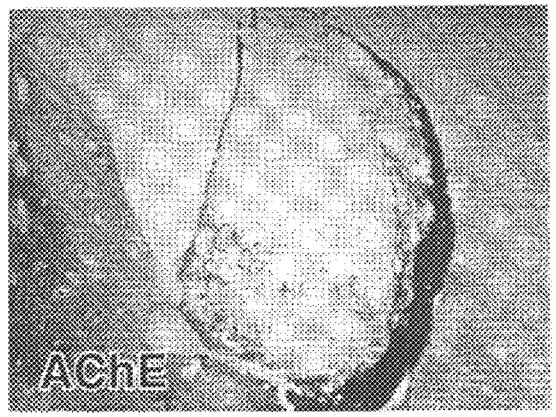
Figure 4C:
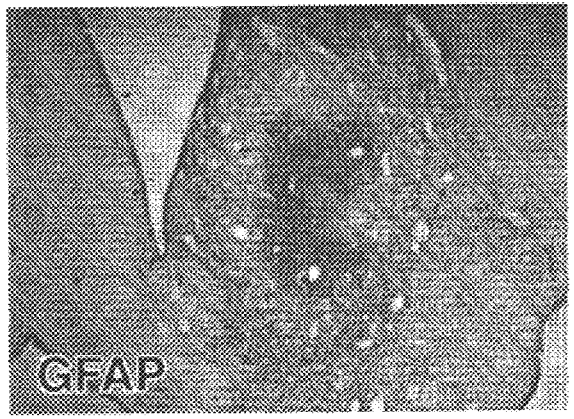
Figure 4D:
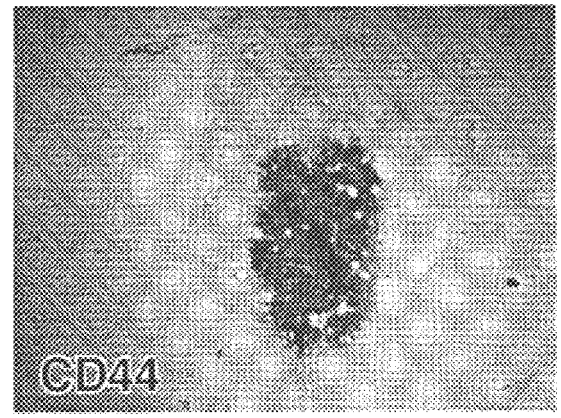
Figure 4E:
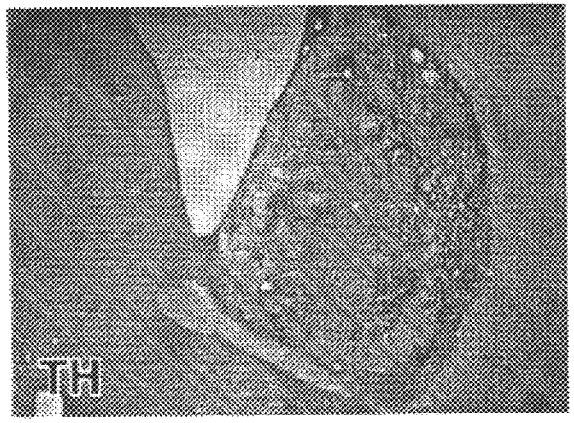
Figure 5A:
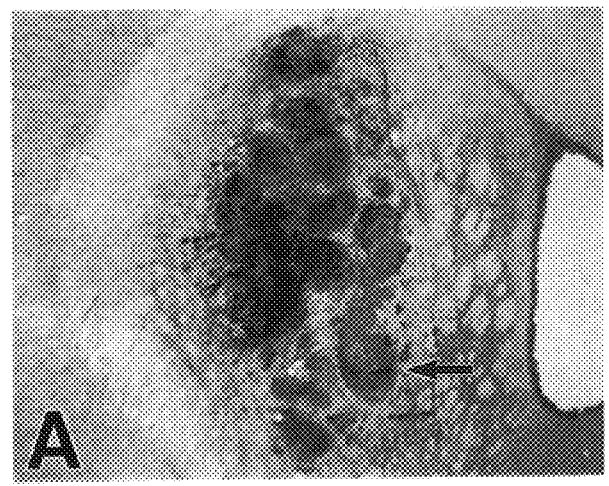
FIGS. 5A–5C depict a representative graft derived from 31 day old pig fetuses. The representative graft is derived from 31 day old pig fetal brain lateral ganglionic eminence (LGE) showing a graft balanced in neural and glial elements.
Figure 5B:
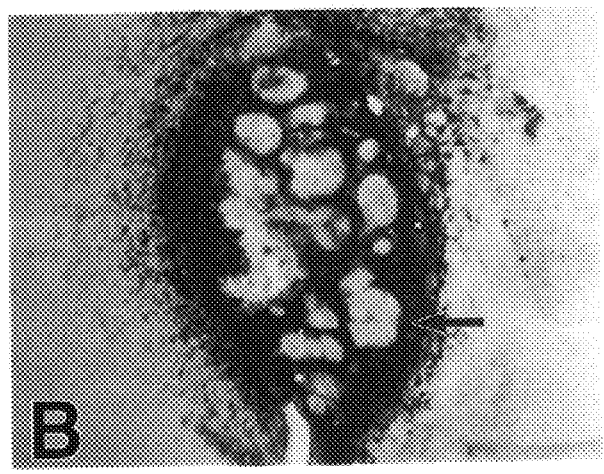
Figure 5C:
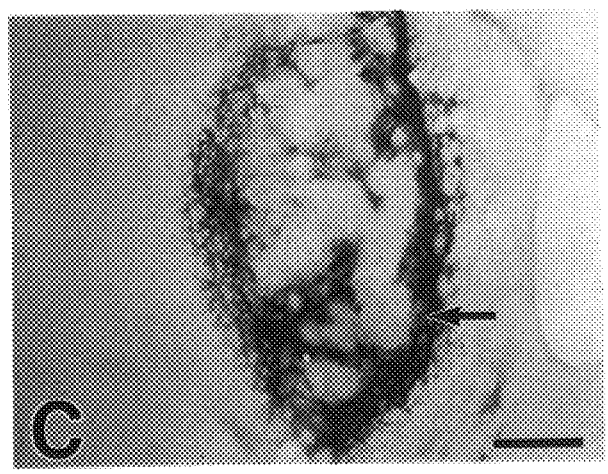

I. Isolated Cells and Cell Populations of the Invention

A. Modified Porcine Neural Cells and an Isolated Population of Modified Porcine Neural Cells This invention features porcine neural cells suitable for introduction into a xenogeneic recipient, particularly a human subject. As used herein the phrase "neural cell" includes both nerve cells (i.e., neurons, e.g., uni-, bi-, or multipolar neurons) and their precursors and glial cells (e.g., macroglia such as oligodendrocytes, Schwann cells, and astrocytes, or microglia) and their precursors. The terms "precursor", "progenitor", and "stem cell" are used interchangeably herein and refer to cells which are pluripotent, i.e., are capable of developing into a many different cell types, including neural cells. Such stem cells can be used as sources of the porcine neural cells of the invention, i.e., the neural cells of the invention can be derived from such stem cells. As used herein, the term "derived" refers to cells which develop or differentiate from or have as ancestors pluripotent stem cells. These pluripotent stem cells are typically obtained and treated as described briefly herein and in detail in PCT publication WO 95/12665, published May 11, 1995, the contents of which are incorporated herein by reference, to generate the cells of the present invention.

For example, porcine fetuses can be removed from a pregnant sow at gestational ages at which the neural cells have not committed to specific cell fates. In one embodiment, the stem cells are obtained from porcine blastocysts or embryos in very early stages of development and cultured under conditions which promote proliferation. Agents, e.g., retinoic acid, nerve growth factor, which promote differentiation of these stem cells into neural cell types, e.g., such as those cell types described herein, can then be added to the culture. The resultant differentiated neural cells can be transplanted into a recipient subject as described herein.

Neural cells of the invention can be obtained from any location in the pig central or peripheral nervous system. In unmodified form, the porcine neural cell has at least one antigen on the cell surface which is capable of stimulating an immune response against the cell in a xenogeneic subject. To inhibit rejection of the cell when introduced into the xenogeneic subject, the antigen on the cell surface is altered prior to transplantation. In an unaltered state, the antigen on the cell surface stimulates an immune response against the cell when the cell is administered to a subject (also referred to herein as recipient or recipient subject). By altering the antigen, the normal immunological recognition of the porcine neural cell by the immune system cells of the recipient is disrupted and additionally, "abnormal" immunological recognition of this altered form of the antigen can lead to porcine neural cell-specific long term unresponsiveness in the recipient. It is likely that alteration of an antigen on the porcine neural cell prior to introducing the cell into a subject interferes with the initial phase of recognition of the porcine neural cell by the cells of the host's immune system subsequent to administration of the cell. Furthermore, alteration of the antigen may induce immunological nonresponsiveness or tolerance, thereby preventing the induction of the effector phases of an immune response (e.g., cytotoxic T cell generation, antibody production etc.) which are ultimately responsible for rejection of foreign cells in a normal immune response. As used herein, the term "altered" encompasses changes that are made to at least one porcine neural cell antigen(s) which reduces the immunogenicity of the antigen to thereby interfere with immunological recognition of the antigen(s) by the recipient's immune system.

Antigens to be altered according to the current invention include antigens on a porcine neural cell which can interact with an immune cell in a xenogeneic (or allogeneic) recipient subject and thereby stimulate a specific immune response against the porcine neural cell in the recipient. The interaction between the antigen and the immune cell may be an indirect interaction (e.g., mediated by soluble factors which induce a response in the immune cell, e.g., humoral mediated) or, preferably, is a direct interaction between the antigen and a molecule present on the surface of the immune cell (i.e., cell—cell mediated). As used herein, the term "immune cell" is intended to include a cell which plays a role in specific immunity (e.g., is involved in an immune response) or plays a role in natural immunity. Examples of immune cells include all distinct classes of lymphocytes (T lymphocytes, such as helper T cells and cytotoxic T cells, B lymphocytes, and natural killer cells), monocytes, macrophages, other antigen presenting cells, dendritic cells, and leukocytes (e.g., neutrophils, eosinophils, and basophils). In a preferred embodiment, the antigen is one which interacts with a T lymphocyte in the recipient (e.g., the antigen normally binds to a receptor on the surface of a T lymphocyte).

In one embodiment, the antigen on the porcine neural cell to be altered is an MHC class I antigen. Alternatively, an adhesion molecule on the cell surface, such as NCAM-1 or ICAM-1, can be altered. An antigen which stimulates a cellular immune response against the cell, such as an MHC class I antigen, can be altered prior to transplantation by contacting the cell with a molecule which binds to the antigen. A preferred molecule for binding to the antigen is an antibody, or fragment thereof (e.g., an anti-MHC class I antibody, or fragment thereof, an anti-ICAM-1 antibody or fragment thereof, an anti-LFA-3 antibody or fragment thereof, or an anti-$\beta_2$ microglobulin antibody or fragment thereof). A preferred antibody fragment is an F(ab')$_2$ fragment. Polyclonal or, more preferably, monoclonal antibodies can be used. Other molecules which can be used to alter an antigen (e.g., an MHC class I antigen) include peptides and small organic molecules which bind to the antigen. Furthermore, two or more different epitopes on the same or different antigens on the cell surface can be altered. A particularly preferred monoclonal antibody for alteration of MHC class I antigens on porcine neural cells is PT85 (commercially available from Veterinary Medicine Research Development, Pullman Wash.). PT85 can be used alone to alter MHC class I antigens or, if each antibody is specific for a different epitope, PT85 can be used in combination with another antibody known to bind MHC class I antigens to alter the antigens on the cell surface. Suitable methods for altering a surface antigen on a cell for transplantation are described in greater detail in Faustman and Coe (1991) *Science* 252:1700–1702 and PCT publication WO 92/04033. Methods for altering multiple epitopes on a surface antigen on a cell for transplantation are described in greater detail in PCT publication WO 95/26741, the contents of which are incorporated herein by reference.

The altered (also referred to herein as "modified") porcine neural cells can comprise a population of cells. The term "population" as used herein refers to a group of two or more cells. The porcine neural cells of the population are typically obtained from a selected area of the brain. The population of porcine neural cells of the present invention need not contain exclusively cells which are uniform in morphology and function. The presence of nonneural cells in addition to neural cells in the population of cells can promote survival and growth of the neural cells upon implantation into a recipient subject. For example, glial cells can provide neurotrophic factors or substrates for neural migration. In addition, glial cells can prolong survival of a neural graft by, for example, insulating the neural tissue from recipient immune cells, thereby inhibiting rejection of the neural graft.

The modified or unmodified cells described herein can be grown as a cell culture, i.e., as a population of cells which grow in vitro, in a medium suitable to support the growth of the cells. Media which can be used to support the growth of porcine neural cells include mammalian cell culture media, such as those produced by Gibco BRL (Gaithersburg, Md.). See 1994 Gibco BRL Catalogue & Reference Guide. The medium can be serum-free or supplemented with animal serum such as fetal calf serum.

For use in transplantation studies and treatment of neurological deficits resulting from neurodegeneration in humans, the altered porcine neural cells of the present invention are isolated at an appropriate stage of development in order to allow for growth, reproduction, and differentiation following transplantation into a xenogeneic subject. Such neurological deficits which result from neurodegeneration or neurodegenerative disorders include, for example, head trauma, stroke, amyotrophic lateral sclerosis (ALS), multiple sclerosis, Alzheimer's disease, Parkinson's disease and Huntington's disease in humans. Preferred porcine neural cells are, therefore, cortical cells, more preferably embryonic cortical cells, for use in treating head trauma, stroke, ALS, multiple sclerosis, Huntington's disease, and Alzheimer's disease; mesencephalic cells, more preferably embryonic mesencephalic cells, for use in treating Parkinson's disease; and striatal cells, more preferably embryonic striatal cells, for use in treating Huntington's disease. To provide for growth, reproduction, and differentiation of porcine neural cells, and in particular, porcine cortical cells, porcine mesencephalic cells and porcine striatal cells, upon transplantation into a recipient subject, an optimal donor is selected. Typically, neural cells of the invention are porcine embryonic cells which are isolated from porcine fetuses which display the desired characteristics for transplantation. For example, in general, neural cells having a fibroblast-like morphology are too immature to harvest and transplant. The preferred morphology of neural cells is the characteristic normal morphology of a neuron including a small rounded cell body which does not adhere to the culture vehicle, e.g., culture dish, as strongly as glial cells, which tend to have a cell body that is relatively flat. Normal neuron morphology also generally includes the presence of neurite processes. Thus, it is preferred that at least about 1%, more preferably at least about 10%, yet more preferably at least about 20%, still more preferably at least about 30%, and most preferably at least about 40% of the neural cells in culture have the characteristic neuron morphology at the time they are harvested for transplantation. The neural cell cultures of the present invention can also include additional cell types, such as glial cells, as described herein. In addition, various methods of increasing the survival of the transplanted cells are described herein.

a. Selecting Mesencephalic Cells of the Appropriate Age for Transplantation

The mesencephalon or midbrain consists of the corpora quadrigemina and the cerebral peduncles. A component of each cerebral peduncle is the substantia nigra. The substantia nigra is one of the primary neurodegenerative areas found in human patients with Parkinson's disease. For treatment of neurodegenerative diseases of, for example, the substantia nigra, porcine mesencephalic cells are isolated from the ventral mesencephalon of an embryonic donor swine (also referred to herein as "pig"). Preferably, mesencephalic cells are isolated from an embryonic pig at a selected gestational age. The selected gestational ages (the total gestation time for pig is 115 days) for isolation of cells were determined based on the following criteria: the viability of the cells upon isolation, the ability of the grafted cells to correct experimentally induced behavior deficits in a xenogeneic subject (e.g., a rat), and the ability to specifically dissect ventral mesencephalon (VM) brain tissue from surrounding connective tissue. It was discovered that the preferred gestational age of embryonic swine from which to obtain mesencephalic cells suitable for transplantation into xenogeneic subjects, particularly humans, is between about days twenty-four (24) to twenty-five (25) and days twenty-nine (29) to thirty (30). This preferred gestational age for mesencephalic cell isolation was determined experimentally as shown in FIG. 1. The results of cell viability tests after isolation of cells from fetuses of varying ages are shown. The results of these studies demonstrate that there is a sharp decline in the viability of isolated VM cells in fetuses older than about twenty-nine (29) to thirty (30) days of development. Additionally, cells with viabilities below 50% generally do not give rise to viable grafts. Therefore, embryonic swine older than twenty-nine (29) to thirty (30) days are not the preferred source of mesencephalic cells for transplantation into humans. In embryonic swine younger than about twenty-four (24) to twenty-five (25) days, the connective tissue is not as easily separated from the desired brain tissue. However, cells obtained from swine younger than twenty-four days can be used for transplantation if desired. Thus, the preferred range for isolation of porcine mesencephalic cells is between about twenty-four (24) to twenty-nine (29) to thirty (30) days of gestation. Another preferred range for isolation of porcine mesencephalic cells is between about twenty-four (24) to twenty-eight (28) days of gestation. A more preferred range for isolation of porcine mesencephalic cells is between about twenty-six (26) and twenty-eight (28) days of gestation. A particularly preferred age of fetal development for isolation of the porcine mesencephalic cells of this invention is day 27. This corresponds to fetal crown-to-rump (CRL) length of between 18 and 25 mm. When grafts (i.e., fetal pig tissue to rat) from such tissue are examined by staining with an antibody to tyrosine hydroxylase, which is the rate limiting enzyme for the synthesis of dopamine and a marker for dopamine neurons, they are shown to contain dopamine neurons (the neurons required to treat Parkinson's disease). Transplantation of such cells has been found to correct behavioral deficits in experimental rats (FIG. 2). The method used to analyze the behavioral deficits in rats is described below under the heading "Method for Treating Neurological Deficits Due to Neurodegeneration in the Brain of a Xenogeneic Subject Using Porcine Neural Cells Obtained from an Essentially Pathogen-Free Swine".

In addition, the porcine mesencephalic cells of the invention can be grown as cell cultures. For example, the present invention includes a cell culture of porcine mesencephalic cells (e.g., ventral mesencephalic cells) wherein at least about 1% to 5% of the porcine mesencephalic cells produce tyrosine hydroxylase. Tyrosine hydroxylase is a well-known enzyme involved in the synthesis of dopamine and can be detected using antibodies. FIG. 22 shows a set of photographs of phase-fluorescence pairs of representative images of fetal ventral mesencephalic cells from several different isolations. Cells were stained for either a polyclonal rabbit antibody to tyrosine hydroxylase (TH) or a monoclonal mouse antibody to neuron-specific enolase (NSE) and then with fluorescein goat anti-rabbit or goat anti-mouse secondary antibodies, respectively. The antibody used for staining is marked in the upper left for each pair. Typically from 1–5% of the cells stain positive for TH and all cells stain for NSE which is a generalized brain cell specific marker. Preferably at least about 10%, more preferably at least about 20%, yet more preferably at least about 30%, still more preferably at least about 40%, most preferably at least about 50% or more of the cells of the cell culture are porcine mesencephalic cells. Another aspect of the invention includes an isolated porcine mesencephalic cell (e.g., ventral mesencephalic cell) which, when transplanted into a xenogeneic subject, produces dopamine. Dopamine production in vivo can be measured, for example, using a microdialyis probe into or near the region where the graft is located. A microdialyis probe has a permeable membrane at one tip. Artificial cerebrospinal fluid (CSF) is circulated through the probe, thus allowing diffusion of dopamine across the membrane and into the artificial CSF in the probe. The resultant artificial CSF can be added to a high performance liquid chromatography column and dopamine can be detected.

b. Selecting Striatal Cells of the Appropriate Age for Transplantation

The striatum or corpus striatum is a structure in the cerebral hemispheres consisting of two basal ganglia (the caudate nucleus and the putamen) and the fibers of the internal capsule that separate them. Although striatal cells from animals other than swine have been used in transplantation studies (See, e.g., Pakzaban, P. et al. (1993) *Exp. Brain Res.* 97:13–22 (rat striatal cells)), the optimal embryonic stage for isolation of porcine striatal cells suitable for transplantation into human subjects was determined experimentally. For example, as shown by a comparison of pig and rat fetal development (FIG. 3), rat embryonic development follows a different course than pig. However, based on the gestational age for isolating rat cells, one would select a gestational age for isolating pig cells which was significantly older than the optimal age as determined experimentally. The optimal donor age in the rat for striatal tissue is between 14 and 15 days of development which corresponds to 67% of the total gestational time. The equivalent stage in the pig would be 70 days (See FIG. 3). However, it was experimentally determined that the optimal age for isolation of striatal cells from embryonic pigs is between about twenty (20) and about fifty (50) days, more preferably about thirty (30) and forty (40) days, yet more preferably about thirty-one (31) and about thirty-eight (38) days, and most preferably about thirty-four (34) and about thirty-six (36) days of gestation. After about fifty (50), more preferably about forty (40), and most preferably about thirty-eight (38) or thirty-nine (39) days, the appropriate target tissue in the striatum cannot be reliably dissected and the quality of grafts post-transplantation is inferior (as shown in FIGS. 4A–4E and 5A–5C). Thus, embryonic porcine striatal cells suitable for transplantation into humans are preferably obtained from embryonic pigs between about twenty (20) and about fifty (50) days, more preferably about thirty (30) and forty (40) days, yet more preferably about thirty-one (31) and about thirty-eight (38) days, and most preferably about thirty-four (34) and about thirty-six (36) days of gestation.

Cell cultures comprising porcine striatal cells (e.g., embryonic porcine striatal cells, e.g., obtained from a lateral ganglionic eminence) wherein preferably at least about 10%, more preferably, at least about 20%, yet more preferably at least about 30%, still more preferably at least about 40%, most preferably at least about 50% or more of the cells of which are porcine striatal cells are also contemplated by the present invention. These cell cultures can also include glial cells, for example, at least about 10%, more preferably, at least about 20%, yet more preferably at least about 30%, still more preferably at least about 40%, most preferably at least about 50% or more glial cells. Another aspect of the invention includes an isolated porcine striatal cell which, upon transplantation into a xenogeneic subject, extends at least one neural process to at least one region of the brain of the subject. As used herein the phrase "neural process" includes any extension of the cell, e.g, an axon or a dendrite in a neuron or a membranous process which forms a myelin sheath around axons in a glial cell, for example, an oligodendrocyte. See Kandel, E. R. and Schwartz, J. H. eds. (1991) Principles of Neural Science, 3rd ed. (Elsevier, New York) pp. 14–19. Preferred target regions of the subject include normal striatal cell efferent target regions of the brain, such as the substantia nigra and globus pallidus.

c. Selecting Cortical Cells of the Appropriate Age for Transplantation

The cerebral cortex is the thin, convoluted surface layer of gray matter of the cerebral hemispheres, consisting principally of cell bodies of neurons arranged in five layers. The cortex has traditionally been divided into four lobes: the frontal, parietal, occipital, and temporal lobes. For treatment of neurological deficits due to neurodegeneration of an area of the cortex, porcine cortical cells are isolated from the cortex, e.g., at a stage of development when areas of the cortex are not yet clearly defined. Cortical cells of the invention, therefore, can be isolated from any location in the cortex. As degeneration of basal forebrain cholinergic neurons and the consequent depletion of acetylcholine (ACh) in the cortex is a particularly salient feature of Alzheimer's disease, a preferred location from which to isolate cortical cells of the invention is from porcine basal forebrain. Basal forebrain cholinergic cells can be isolated from pig fetuses at about day twenty (20) to day thirty (30) of gestation, more preferably from about day twenty-four (24) to day twenty-eight (28) of gestation, and most preferably, at about day twenty-seven (27) of gestation. Such porcine cells can be used to replace the basal forebrain cholinergic cells lost in the Alzheimer subject and reduce associated cognitive deficits. Preferably cortical cells are isolated from an embryonic pig at a selected gestational age. Cortical cells of the appropriate gestational age for transplantation can be selected based on the degree or extent of neural process formation. In general, cortical cells which have the longest distances to grow to reach their targets are the cells that begin process outgrowth earliest in development and the cortical cells that have shorter distances to grow to reach their targets begin process outgrowth later. Neural process outgrowth occurs until late stages of fetal development up until birth and after birth, but long distance neural process outgrowth ceases at an earlier stage, i.e., at about day 30 of fetal development. Cortical cells of the appropriate gestational age for transplantation can, therefore, be selected by identifying cortical cells at a developmental stage such that at least a portion of neural process outgrowth has begun. Preferably, the cells are selected such that both short and long distance neural process outgrowth has begun but before all long distance outgrowth has begun. Examples of parameters which can be employed to select porcine cortical cells at the proper gestational age for transplantation include the following: (1) the cortical cells are preferably recently post-mitotic, e.g., as determined by $^3$H-thymidine incorporation. For example, cells which show the darkest nuclei after a thymidine pulse are those that stopped dividing shortly after the pulse, and are, therefore, recently postmitotic; (2) the cortical cells are preferably migrating cells or have recently reached their final destination; and (3) the cortical cells have preferably not sent out elaborate neural processes which, when severed during, for example, isolation, can result in cell death. It was discovered that the preferred gestational age of embryonic swine from which to obtain cortical cells suitable for transplantation into xenogeneic subjects, particularly humans, is between about days twenty-seven (27) to fifty (50), more preferably twenty-seven (27) to forty (40), yet more preferably tweny-seven (27) to thirty-nine (39), still more preferably twenty-seven (27) to thirty-eight (38), still further preferably twenty-seven (27) to twenty-seven (27), and most preferably thirty-five (31) to thirty-four (34) of gestation.

Cell cultures comprising porcine cortical cells (e.g., embryonic porcine cortical cells) wherein preferably at least about 10%, more preferably at least about 20%, yet more preferably at least about 30%, still more preferably at least about 40%, most preferably at least about 50% or more of the cells of which have at least one neural process are also contemplated by the present invention. A further aspect of the invention includes an isolated porcine cortical cell which, upon transplantation into a xenogeneic subject, extends at least one neural process to at least one subcortical target region in the brain of the subject. Typical cortical cell efferent target regions of the brain include corpus callosum, cingulum bundle, internal capsule, and cerebral peduncle.

B. An Isolated Population of Porcine Striatal Cells, an Isolated Population of Porcine Striatal Cells which Enhance GABA-ergic Transmission when Transplanted into a Subject, and an Isolated Population of Cortical Cells This invention also features an isolated population of cells obtained from porcine striatum. The location and components of the striatum are described above. As used herein, the term "isolated" refers to a cell or population of cells which has been separated from its natural environment. This term includes gross physical separation from its natural environment, e.g., removal from the donor animal, e.g., a pig, and alteration of the cell's relationship with the neighboring cells with which it is in direct contact by, for example, dissociation. The term "isolated" does not refer to a cell or population of cells which is in a tissue section, is cultured as part of a tissue section, or is transplanted in the form of a tissue section. When used to refer to a population of porcine neural cells, the term "isolated" includes populations of cells which result from proliferation of the isolated cells of the invention. The term "population" is intended to include a group of two or more cells. Cells in a population of cells can be obtained from the same or different source(s), e.g., the same swine or several different swine. However, the cells are not necessarily of the same cell type. Cells obtained from porcine striatum, for example, can include a range of different cell types including, but not limited to, neural cells and neural progenitor cells. For example, an isolated population of porcine striatal cells (or other populations of neural cells of the invention) can include neural cells, neural progenitor cells, glial cells, glial progenitor cells, endothelial cells, and hematopoietic cells. Progenitor or precursor cells can be distinguished from committed cells by, for example, differential staining. For example, neural and glial cell precursors express vimentin and can be identified with a vimentin-specific stain while mature neural cells and glial cells do not generally express vimentin. In addition, neural and glial cell precursors can be distinguished from their committed counterparts by staining for neural epithelial stem cell antigen (NESTIN). The neural and glial cell precursors stain positive for NESTIN while their committed counterparts do not. Frederiksen, K. et al. (1988) *J. Neurosci.* 8:1144–1151.

In one embodiment, the isolated population of porcine striatal cells is obtained from embryonic porcine striatum and includes at least neural progenitor cells. The embryonic porcine striatal cells are preferably obtained from embryonic pigs between about twenty (20) and about fifty (50) days, more preferably about thirty (30) and forty (40) days, yet more preferably about thirty-one (31) and about thirty-eight (38) days, and most preferably about thirty-four (34) and about thirty-six (36) days.

The porcine striatal cells of the invention are preferably obtained from a ganglionic eminence (i.e., the lateral and/or medial ganglionic eminence) of the striatum, but are more preferably obtained from a lateral ganglionic eminence of porcine striatum at the preferred gestational age described herein.

In one embodiment, the isolated population of porcine striatal cells includes at least two different cells types. Preferably these cell types are neural progenitor cells and glial cells. Examples of glial cells that can be included in the isolated population of porcine striatal cells are glial cells which express cluster-of-differentiation factor 44 (CD44, also known as H-CAM or Hermes antigen). CD44 is a cell surface glycoprotein of approximately 90 kD which has been implicated in the binding of hyaluronate to the cell surface (Asher, R. and Bignani, A. (1992) *Exp. Cell Res.* 203:80–90) in T cell/endothelial cell interactions in synovium, mucosa, and lymph nodes (Hale, L. P. et al. (1989) *J. Immunol.* 143:3944–3948). CD44 is widely expressed in human CNS white matter by subsets of glial cells, and within the neuropil of several gray matter structures (Vogel, E. et al. (1992) *J. Neurocytol.* 21:363–373). Porcine striatal CD44-immunoreactive glia provide substrates and other influences (e.g., neurotrophic factors) that, when the porcine striatal cells are introduced into a subject, promote striatal axonal growth from a porcine striatal graft into the surrounding tissue.

Another aspect of the invention pertains to an isolated population of porcine striatal cells which, when introduced into a xenogeneic subject, enhance GABA-ergic transmission in and around the area populated by the implanted porcine striatal cells. Typically, the porcine striatal cells which enhance GABA (gamma-aminobutyric acid)-ergic transmission are derived from a lateral ganglionic eminence. In a preferred embodiment, the porcine striatal cells are derived from embryonic porcine striatum. The phrase "enhance GABA-ergic transmission" is intended to include production of gamma-aminobutyric acid in a xenogeneic subject into which porcine striatal cells of the present invention have been introduced which is greater than production of gamma-aminobutyric acid in a xenogeneic subject into which porcine neural cells or porcine neural progenitor cells other than porcine striatal cells have been introduced.

The present invention also features an isolated population of porcine cortical cells, preferably embryonic porcine cortical cells, e.g., at the gestational ages described herein. The terms "isolated" and "population" are also described herein.

C. A Porcine Neural Cell Isolated from an Essentially Pathogen-Free Swine

The invention also features a porcine neural cell isolated from a swine which is essentially free from organisms or substances which are capable of transmitting infection or disease to a xenogeneic recipient, e.g., a human recipient, of the cells. Typically, porcine neural cells are isolated from a swine which is essentially free from human pathogens. For example, the pathogens from which the swine are free include, but are not limited to, one or more of pathogens from the following categories of pathogens: parasites, bacteria, mycoplasma, and viruses. The swine can be free from, for example, parasites such as toxoplasma and eperylherozoon, or mycoplasma, such as M. hyopneumonia. Examples of bacteria from which the swine can be free include brucella, listeria, mycobacterium TB, leptospirillum, and haemophilus suis. Additionally, the swine can be free from viruses such as zoonotic, cross placenta, and neurotropic viruses. Specific examples of viruses from which the swine are free include: a virus which causes (or results in) porcine respiratory reproductive syndrome, a virus in the rabies virus group, a herpes-like virus which causes pseudorabies, parvovirus, encephalomyocarditus virus, a virus which causes swine vesicular disease, porcine poliovirus (techen), a virus which causes hemmaglutinating encephalomyocarditus, cytomegalovirus, suipoxvirus, swine influenza type A, adenovirus, transmissible gastroenteritus virus, a virus which causes bovine viral diarrhea, parainfluenza virus 3, and vesicular stomatitis virus.

In one embodiment, the pigs from which neural cells are isolated are essentially free from one or more and preferably all of the following organisms: Toxoplasma, eperythrozoon, brucella, listeria, mycobacterium TB, leptospirillum, haemophilus suis, M. Hyopneumonia, a virus which causes porcine respiratory reproductive syndrome, a virus which causes rabies, a virus which causes pseudorabies, parvovirus, encephalomyocarditus virus, a virus which causes swine vesicular disease, porcine polio virus (techen), a virus which causes hemagglutinating encephalomyocarditus, suipoxvirus, swine influenza type A, adenovirus, transmissible gastroenteritis virus, a virus which causes bovine viral diarrhea, and vesicular stomatitis virus. The phrase "essentially free organism" (also referred to herein as "essentially pathogen-free") when referring to a swine from which cells are isolated means that the organism is not present in the swine in an amount which is capable of transmitting infection or disease to a xenogeneic recipient, e.g., a human. Example VII provides representative, but not limiting examples of methods for selecting swine which are essentially free from the various organisms. Embryonic or post-natal swine which are determined to be essentially free of such organisms are maintained under suitable conditions until used as a source of neural cells.

Preferred neural cells isolated from the essentially pathogen-free swine include cortical cells, mesencephalic cells and striatal cells. Optimal gestational ages of the swine from which these cells are isolated are described in detail herein. Porcine neural cells isolated from essentially pathogen-free swine can additionally be modified to reduce the immunogenicity of the cells following transplantation into a xenogeneic subject as described herein.

II. Methods of the Invention

A. Method for Isolating Porcine Neural Cells from an Essentially Pathogen-Free Swine Another aspect of the invention pertains to a method for isolating a neural cell from a pig which is essentially free from organisms or substances which are capable of transmitting infection or disease to a xenogeneic recipient of the cells. According to the method, swine are tested for the presence or absence of organisms or substances which are capable of transmitting infection or disease to a xenogeneic recipient, e.g., a human recipient, of the cells. Such organisms include, but are not limited to, one or more of pathogens from the following categories of pathogens: parasites, bacteria, mycoplasma, and viruses. The swine can be free from, for example, parasites such as toxoplasma and eperylherozoon, or mycoplasma, such as M. hyopneumonia. Examples of bacteria from which the swine can be free include brucella, listeria, mycobacterium TB, leptospirillum, and haemophilus suis. Additionally, the swine can be free from viruses such as zoonotic, cross placenta, and neurotrophic viruses. Specific examples of viruses from which the swine are free include: a virus which causes (or results in) porcine respiratory reproductive syndrome, a virus in the rabies virus group, a herpes-like virus which causes pseudorabies, parvovirus, encephalomyocarditus virus, a virus which causes swine vesicular disease, porcine poliovirus (techen), a virus which causes hemmaglutinating encephalomyocarditus, cytomegalovirus, suipoxvirus, swine influenza type A, adenovirus, transmissible gastroenteritus virus, a virus which causes bovine viral diarrhea, parainfluenza virus 3, and vesicular stomatitis virus. Preferably, neural cells are isolated from embryos of swine which are essentially free of these organisms.

Methods for isolating neural cell tissue are known in the art. For example, solid neural tissue samples can be dissected from surrounding brain tissue, e.g., by dissecting the tissue under a microscope. The cells in the neural tissue sample can then be dissociated by mechanical means, e.g., chopping and/or successive pipette trituration, or by chemical means, e.g., enzymes. The swine which are employed in the method of the invention as a source of neural cells include embryonic swine (swine fetuses) and postnatal swine. If an embryonic swine is to be used as a source of neural cells, semen from a boar which has been tested to be essentially free of disease transmitting organisms is employed to artificially inseminate a female swine which is essentially free from such organisms. At a selected gestational age, e.g., the gestational age of a cell type, e.g., a cortical cell, a mesencephalic cell, or a striatal cell, described herein, a hysterectomy is performed under appropriate conditions of sterility and the fetuses are thereafter removed in their individual amniotic sacs. Appropriate neural cells or tissue are thereafter recovered under appropriate conditions of sterility.

The swine which are essentially free from organisms or substances which transmit infection or disease to a recipient subject can be employed as a source of a wide variety of cells, e.g, neural cells. Porcine neural cells which can be isolated according to this method include, for example, cortical cells, mesencephalic cells and striatal cells as described in further detail herein. Porcine neural cells isolated from essentially pathogen-free swine can additionally be modified as described herein.

B. Method for Treating Neurological Deficits Due to Neurodegeneration in the Brain of a Xenogeneic Subject Using Modified Porcine Neural Cells A still further aspect of the invention pertains to methods for treating neurological deficits due to neurodegeneration in the brain of a xenogeneic subject, particularly a human subject, in which porcine neural cells are introduced into an area of neurodegeneration in the brain of the subject. As used herein, the phrase "neurological deficits" includes an impairment or absence of a normal neurological function or presence of an abnormal neurological function. The porcine neural cells, in unmodified form, have at least one antigen on the cell surface which is capable of stimulating an immune response against the cell in a xenogeneic subject. Prior to transplantation, the antigen on the cell surface is altered to inhibit rejection of the cell when introduced into the xenogeneic subject. As used herein, the terms "introducing", "implanting", and "transplanting" are used interchangeably. The porcine neural cells of the invention are introduced into a subject by any appropriate route which results in delivery of the cells to a desired location in the subject. For example, a common method of administration of cells into the brain of a subject is by direct stereotaxic injection of the cells into the area of neurodegeneration of the brain. See e.g., Bj orklund, A. et al. (1983) *Acta Physiol. Scand. Suppl.* 522:1–75. Cells can be administered in a physiologically compatible carrier, such as a buffered saline solution. To treat neurological deficits due to unilateral neurodegeneration in the brain of a human subject, about 12–20 million neural cells of the invention are introduced into the area of neurodegeneration. In humans with areas of brain neurodegeneration which occur bilaterally, about 12–20 million neural cells of the invention are introduced into each area of neurodegeneration, requiring a total of about 24–40 million neural cells. About 2 million neural cells can be harvested from each fetal pig. Thus, about 2 to about 12 fetal pigs (approximately one litter of fetal pigs) are generally used to harvest the appropriate number of cells for introduction into a human subject.

The cells of the invention can be inserted into a delivery device which facilitates introduction by e.g., injection, of the cells into the subjects. Such delivery devices include tubes, e.g., catheters, for injecting cells and fluids into the body of a recipient subject. In a preferred embodiment, the tubes additionally have a needle, e.g., a syringe, through which the cells of the invention can be introduced into the subject at a desired location. The porcine neural cells of the invention can be inserted into such a delivery device, e.g., a syringe, in the form of a solution. Alternatively, the cells can be embedded in a support matrix when contained in such a delivery device. As used herein, the term "solution" includes a pharmaceutically acceptable carrier or diluent in which the cells of the invention remain viable. Pharmaceutically acceptable carriers and diluents include saline, aqueous buffer solutions, solvents and/or dispersion media. The use of such carriers and diluents is well known in the art. The solution is preferably sterile and fluid to the extent that easy syringability exists. Preferably, the solution is stable under the conditions of manufacture and storage and preserved against the contaminating action of microorganisms such as bacteria and fungi through the use of, for example, parabens, chlorobutanol, phenol, ascorbic acid, thimerosal, and the like. Solutions of the invention can be prepared by incorporating porcine neural cells as described herein in a pharmaceutically acceptable carrier or diluent and, as required, other ingredients enumerated above, followed by filtered sterilization.

Support matrices in which the porcine neural cells can be incorporated or embedded include matrices which are recipient-compatible and which degrade into products which are not harmful to the recipient. Natural and/or synthetic biodegradable matrices are examples of such matrices. Natural biodegradable matrices include collagen matrices. Synthetic biodegradable matrices include synthetic polymers such as polyanhydrides, polyorthoesters, and polylactic acid.

The methods of the invention are particularly useful for treating human subjects displaying neurological deficits which result from neurodegeneration in the brain. Such brain neurodegeneration can be the result of disease, injury, and/or aging. As used herein, neurodegeneration includes morphological and/or functional abnormality of a neural cell or a population of neural cells. Non-limiting examples of morphological and functional abnormalities include physical deterioration and/or death of neural cells, abnormal growth patterns of neural cells, abnormalities in the physical connection between neural cells, under- or over production of a substance or substances, e.g., a neurotransmitter, by neural cells, failure of neural cells to produce a substance or substances which it normally produces, production of substances, e.g., neurotransmitters, and/or transmission of electrical impulses in abnormal patterns or at abnormal times. Neurodegeneration can occur in any area of the brain of a subject and is seen with many disorders including, for example, head trauma, stroke, ALS, multiple sclerosis, Huntington's disease, Parkinson's disease, and Alzheimer's disease.

In one embodiment of the invention, porcine striatal cells, preferably obtained from embryonic porcine lateral ganglionic eminence at about days thirty-one (31) to thirty-eight (38) of gestation, are transplanted into the brain of a human subject to treat neurological deficits due to neurodegeneration that occurs in the basal ganglia, for example in one or both nuclei forming the striatum or corpus striatum, the caudate nucleus and putamen. Neurodegeneration in Huntington's disease typically involves degeneration in these areas. Striatal cells obtained from embryonic porcine lateral ganglionic eminence at about days thirty-one (31) to thirty-eight (38) of gestation can also be transplanted into the brain of a human subject to treat neurological deficits due to neurodegeneration that occurs in affected brain regions, e.g., at the epileptic foci, of epileptic subjects. Non-limiting examples of such regions include the CA1 region of the hippocampus, amygdala, claustrum, entorhinal cortex, and substantia nigra.

In another embodiment, the mesencephalic cells, preferably obtained from embryonic porcine ventral mesencephalon at about days twenty-six (26) to twenty-eight (28), preferably at about day twenty-seven (27) of gestation, are transplanted into the brain of a human subject to treat neurological deficits due to neurodegeneration that occurs in a nonstriatal area, for example neurodegeneration that occurs in Parkinson's disease. Parkinson's disease in humans primarily affects subcortical structures, especially the substantia nigra and locus ceruleus. It is characterized by the loss of dopamine neurons in the substantia nigra, which have the basal ganglia as their major target organ.

In yet another embodiment, porcine cortical cells, preferably obtained from embryonic porcine cortex at about days twenty-seven (27) to forty (40) of gestation, are transplanted into the brain of a human subject to treat neurological deficits due to neurodegeneration that occurs in the cortex. Cortical neurodegeneration can result in a variety of disorders depending on the area of the cortex affected. For example, head trauma and stroke can be associated with neurodegeneration in all areas of the cortex and brain stem; ALS can be associated with neurodegeneration in the motor cortex and brain stem; Huntington's disease can be associated with neurodegeneration in the striatum and motor cortex; and Alzheimer's disease can be associated with neurodegeneration in the hippocampus, neocortex, mainly frontal, parietal and anterior temporal lobe, and in the amygdala and olfactory system.

Transplantation of porcine neural cells of the invention into the brain of a human subject at an area(s) of neurodegeneration results in reconstitution of damaged neural circuits, and/or replacement of lost neurons and neurotransmitter systems. The term "subject" is intended to include mammals, particularly humans, susceptible to injury-, age- and/or disease-related neurodegeneration. The term "subject" also includes mammals in which an immune response is elicited against allogeneic or xenogeneic cells. Examples of subjects include primates (e.g., humans, and monkeys). A "xenogeneic subject" as used herein is a subject into which cells of another species are transplanted or are to be transplanted. Porcine neural cells are introduced into a subject in an amount suitable to reconstitute damaged neural circuits, and/or replace lost neurons and neurotransmitter systems such there is an at least partial correction of a neurological deficit caused by neurodegeneration. Preferred porcine neural cells are mesencephalic cells, striatal cells, and cortical cells obtained from embryonic swine and at selected embryonic ages described in detail herein.

Prior to introduction into areas of neurodegeneration in the brain of a subject, the porcine neural cells can be modified to enhance their neuroregenerative capacity and/or inhibit immunological rejection. The porcine neural cells can, as described in detail above, be rendered suitable for introduction into a xenogeneic subject by alteration of at least one immunogenic cell surface antigen (e.g., an MHC class I antigen). To inhibit rejection of transplanted porcine neural cells and to achieve immunological non-responsiveness in an allogeneic or xenogeneic transplant recipient, the method of the invention can include alteration of immunogenic antigens on the surface of the porcine striatal cells prior to introduction into the subject. This step of altering one or more immunogenic antigens on porcine neural cells can be performed alone or in combination with administering to the subject of an agent which inhibits T cell activity in the subject. Alternatively, inhibition of rejection of a porcine neural cell graft can be accomplished by administering to the subject an agent which inhibits T cell activity in the subject in the absence of prior alteration of an immunogenic antigen on the surface of the porcine striatal cell. As used herein, an agent which inhibits T cell activity is defined as an agent which results in removal (e.g., sequestration) or destruction of T cells within a subject or inhibits T cell functions within the subject (i.e., T cells may still be present in the subject but are in a non-functional state, such that they are unable to proliferate or elicit or perform effector functions, e.g. cytokine production, cytotoxicity etc.). The term "T cell" encompasses mature peripheral blood T lymphocytes. The agent which inhibits T cell activity may also inhibit the activity or maturation of immature T cells (e.g., thymocytes).

A preferred agent for use in inhibiting T cell activity in a recipient subject is an immunosuppressive drug. The term "immunosuppressive drug or agent" is intended to include pharmaceutical agents which inhibit or interfere with normal immune function. A preferred immunsuppressive drug is cyclosporin A. Other immunosuppressive drugs which can be used include FK506, and RS-61443. In one embodiment, the immunosuppressive drug is administered in conjunction with at least one other therapeutic agent. Additional therapeutic agents which can be administered include steroids (e.g., glucocorticoids such as prednisone, methyl prednisolone and dexamethasone) and chemotherapeutic agents (e.g., azathioprine and cyclosphosphamide). In another embodiment, an immunosuppressive drug is administered in conjunction with both a steroid and a chemotherapeutic agent. Suitable immunosuppressive drugs are commercially available (e.g., cyclosporin A is available from Sandoz, Corp., East Hanover, N.J.).

An immunsuppressive drug is administered in a formulation which is compatible with the route of administration. Suitable routes of administration include intravenous injection (either as a single infusion, multiple infusions or as an intravenous drip over time), intraperitoneal injection, intramuscular injection and oral administration. For intravenous injection, the drug can be dissolved in a physiologically acceptable carrier or diluent (e.g., a buffered saline solution) which is sterile and allows for syringability. Dispersions of drugs can also be prepared in glycerol, liquid polyethylene glycols, and mixtures thereof and in oils. Convenient routes of administration and carriers for immunsuppressive drugs are known in the art. For example, cyclosporin A can be administered intravenously in a saline solution, or orally, intraperitoneally or intramuscularly in olive oil or other suitable carrier or diluent.

An immunosuppressive drug is administered to a recipient subject at a dosage sufficient to achieve the desired therapeutic effect (e.g., inhibition of rejection of transplanted cells). Dosage ranges for immunosuppressive drugs, and other agents which can be coadministered therewith (e.g., steroids and chemotherapeutic agents), are known in the art (See e.g., Freed et al. *New Engl. J. Med.* (1992) 327:1549: Spencer et al. (1992) *New Engl. J. Med.* 327:1541; Widner et al. (1992) *New Engl. J. Med.* 327:1556; Lindvall et al. (1992) *Ann. Neurol.* 31:155; and Lindvall et al. (1992) *Arch. Neurol.* 46:615). A preferred dosage range for immunosuppressive drugs, suitable for treatment of humans, is about 1–30 mg/kg of body weight per day. A preferred dosage range for cyclosporin A is about 1–10 mg/kg of body weight per day, more preferably about 1–5 mg/kg of body weight per day. Dosages can be adjusted to maintain an optimal level of the immunosuppressive drug in the serum of the recipient subject. For example, dosages can be adjusted to maintain a preferred serum level for cyclosporin A in a human subject of about 100–200 ng/ml. It is to be noted that dosage values may vary according to factors such as the disease state, age, sex, and weight of the individual. Dosage regimens may be adjusted over time to provide the optimum therapeutic response according to the individual need and the professional judgment of the person administering or supervising the administration of the compositions, and that the dosage ranges set forth herein are exemplary only and are not intended to limit the scope or practice of the claimed composition.

In one embodiment of the invention, an immunsuppressive drug is administered to a subject transiently for a sufficient time to induce tolerance to the transplanted cells in the subject. Transient administration of an immunosuppressive drug has been found to induce long-term graft-specific tolerance in a graft recipient (See Brunson et al. (1991) *Transplantation* 52:545; Hutchinson et al. (1981) *Transplantation* 32:210; Green et al. (1979) *Lancet* 2:123; Hall et al. (1985) *J. Exp. Med.* 162:1683). Administration of the drug to the subject can begin prior to transplantation of the cells into the subject. For example, initiation of drug administration can be a few days (e.g., one to three days) before transplantation. Alternatively, drug administration can begin the day of transplantation or a few days (generally not more than three days) after transplantation. Administration of the drug is continued for sufficient time to induce donor cell-specific tolerance in the recipient such that donor cells will continue to be accepted by the recipient when drug administration ceases. For example, the drug can be administered for as short as three days or as long as three months following transplantation. Typically, the drug is administered for at least one week but not more than one month following transplantation. Induction of tolerance to the transplanted cells in a subject is indicated by the continued acceptance of the transplanted cells after administration of the immunosuppressive drug has ceased. Acceptance of transplanted tissue can be determined morphologically (e.g., with skin grafts by examining the transplanted tissue or by biopsy) or by assessment of the functional activity of the graft.

Another type of agent which can be used to inhibit T cell activity in a subject is an antibody, or fragment or derivative thereof, which depletes or sequesters T cells in a recipient. Antibodies which are capable of depleting or sequestering T cells in vivo when administered to a subject are known in the art. Typically, these antibodies bind to an antigen on the surface of a T cell. Polyclonal antisera can be used, for example anti-lymphocyte serum. Alternatively, one or more monoclonal antibodies can be used. Preferred T cell-depleting antibodies include monoclonal antibodies which bind to CD2, CD3, CD4 or CD8 on the surface of T cells. Antibodies which bind to these antigens are known in the art and are commercially available (e.g., from American Type Culture Collection). A preferred monoclonal antibody for binding to CD3 on human T cells is OKT3 (ATCC CRL 8001). The binding of an antibody to surface antigens on a T cell can facilitate sequestration of T cells in a subject and/or destruction of T cells in a subject by endogenous mechanisms. Alternatively, a T cell-depleting antibody which binds to an antigen on a T cell surface can be conjugated to a toxin (e.g., ricin) or other cytotoxic molecule (e.g., a radioactive isotope) to facilitate destruction of T cells upon binding of the antibody to the T cells. See PCT publication WO 95/26740, for further details concerning the generation of antibodies which can be used in the present invention.

Another type of antibody which can be used to inhibit T cell activity in a recipient subject is an antibody which inhibits T cell proliferation. For example, an antibody directed against a T cell growth factor, such as IL-2, or a T cell growth factor receptor, such as the IL-2 receptor, can inhibit proliferation of T cells (See e.g., DeSilva, D. R. et al. (1991) *J. Immunol.* 147:3261–3267). Accordingly, an IL-2 or an IL-2 receptor antibody can be administered to a recipient to inhibit rejection of a transplanted cell (see e.g. Wood et al. (1992) *Neuroscience* 49:410). Additionally, both an IL-2 and an IL-2 receptor antibody can be coadministered to inhibit T cell activity or can be administered with another antibody (e.g., which binds to a surface antigen on T cells).

An antibody which depletes, sequesters or inhibits T cells within a recipient can be administered at a dose and for an appropriate time to inhibit rejection of cells upon transplantation. Antibodies are preferably administered intravenously in a pharmaceutically acceptable carrier or diluent (e.g., a sterile saline solution). Antibody administration can begin prior to transplantation (e.g., one to five days prior to transplantation) and can continue on a daily basis after transplantation to achieve the desired effect (e.g., up to fourteen days after transplantation). A preferred dosage range for administration of an antibody to a human subject is about 0.1–0.3 mg/kg of body weight per day. Alternatively, a single high dose of antibody (e.g., a bolus at a dosage of about 10 mg/kg of body weight) can be administered to a human subject on the day of transplantation. The effectiveness of antibody treatment in depleting T cells from the peripheral blood can be determined by comparing T cell counts in blood samples taken from the subject before and after antibody treatment. Dosage regimes may be adjusted over time to provide the optimum therapeutic response according to the individual need and the professional judgment of the person administering or supervising the administration of the compositions. Dosage ranges set forth herein are exemplary only and are not intended to limit the scope or practice of the claimed composition.

In another embodiment, the porcine neural cells (e.g., neural cells, neural progenitor cells) of the invention are genetically engineered to express and/or secrete a foreign molecule (e.g., a neurotrophic factor, a neurotransmitter, or a neuroprotective agent), e.g., to enhance their neuroregenerative capacity. In addition, unmodified or modified porcine neural cells can be introduced into the brain of a xenogeneic subject together with other types of cells (e.g., other cells derived from porcine striatum, or cells derived from other sources) which have been genetically modified to perform a useful function. For example, in order to promote growth of neurons in an area of neurodegeneration in the brain of a subject, the neural progenitor cells derived from the porcine striatum can be implanted into the area of neurodegeneration together with other cells which have been modified to secrete, for example, a neurotrophic factor. Examples of cells that act as carriers of transgenes to the brain of a subject include fibroblasts (Fisher, L. J. et al. (1991) *Neuron* 6:371–380; Rosenberg, M. B. et al. (1988) *Science* 242:1575–1578), adrenal chromaffin cells (Cunningham, L. A. et al. (1991) *Brain Res.* 561:192–202), astrocytes (Suhr, S. T. and Gage, F. H. (1993) *Arch. Neurol.* 50(11):1252–1268), and myoblasts (Jiao, S. et al. (1993) *Nature* 362:450–453; Jiao, S. et al. (1992) *Brain Res.* 575:143–147; Jiao, S. et al. (1992) *Hum. Gene Ther.* 3:21–33). Such cells, e.g., fibroblasts, glial cells, can also be used to deliver retroviruses containing genes, e.g., herpes simplex thymidine kinase gene, the gene products of which are targets for other therapeutic drugs or agents, e.g., ganciclovir, to target cells, e.g., tumor cells, to inhibit their growth. Culver, K. et al. (1992) *Science* 256:1550–1552; Chen, S-H. et al. (1994) *Proc. Natl. Acad. Sci. USA* 91:3054–3057. Alternatively, the neural progenitor cells derived from porcine striatum which are to be implanted into an area of neurodegeneration can themselves be genetically modified to produce, for example, a neurotrophic factor to enhance the growth and development of the implant.

There are several mechanisms by which neurodegeneration can be treated using the methods of the present invention or in conjunction with the methods of the present invention. For example, a new function can be introduced into a target cell (e.g., a damaged neural cell) in a phenotypically useful way. A new function can be expressed in such defective target cells (e.g., damaged neural cells) by introducing a genetically modified cell (e.g., porcine striatal cells, fibroblasts, myoblasts, etc.) that can establish a tight junction or other contacts with the target cell. Some such contacts are known to permit the efficient diffusion of metabolically important small molecules from one cell to another, leading to phenotypic changes in the recipient cell. Loewenstein, W. R. (1979) *Biochim. Biophys. Acta.* 560:1–66. This process has been called "metabolic co-operation" and is known to occur between fibroblasts and glial cells. Gruber, H. E. et al. (1985) *Proc. Natl. Acad. Sci. USA* 82:6662–6666. This type of co-operativity has been demonstrated with CNS cells, as in the case of NGF-mediated protection of cholinergic neural death following CNS damage. Hefti, F. (1986) *J. Neurosci.* 6:2155; Williams, L. R. et al. (1986) *Proc. Natl. Acad. Sci. USA* 83:9231–9235.

Another mechanism by which neurodegeneration can be treated using the methods of the invention includes the generation of still other genetically modified cells which can express and secrete a diffusible gene product that can be taken up and used by nearby target cells. One strategy that has been pursued in animal models of neurodegenerative disease is to augment neurotransmitter function within the brain through tissue transplantation. For example, fibroblast cell lines have been modified to express choline acetyltransferase. The modified fibroblasts have then been implanted into the hippocampus of rats where they continue to produce and release acetylcholine after grafting. Fisher, L. J. et al. (1993) *Ann. N.Y. Acad. Sci.* 695:278–284. Fibroblasts have also been genetically modified to produce tyrosine hydroxylase (an enzyme that converts tyrosine to L-DOPA) and implanted into the striatum of recipient rats with a prior 6-hydroxydopamine lesion. The implanted fibroblasts continue to convert tyrosine to L-DOPA in the host striatum and to affect the host brain as assessed through behavioral measurements. Fisher, L. J. et al. (1991) *Neuron* 6:371–380.

Another strategy that has been pursued in animal models of neurodegenerative disease is to deliver neurotrophic factors, such as nerve growth factor (NGF), which sustains the growth and development of neurons, prevents damage-induced death, and attracts the growth of developing or regenerating axons, to the area of neurodegeneration. Fibroblasts can be modified to secrete NGF. When these fibroblasts are introduced into striatum of a subject such as a rat, they protect neurons from excitotoxin-induced lesions. Schumacher, J. M. et al. (1991) *Neuroscience* 45(3):561–570. Porcine striatal cells of the invention and other types of cells which are to be transplanted with the porcine striatal cells can additionally be genetically engineered to express glial cell line-derived neurotrophic factor (GDNF) (Leu-Fen, H. et al. (1993) *Science* 260:1130–1132), a potent neurotrophic factor that enhances survival of midbrain dopaminergic neurons.

A cell to be introduced into the subject can be genetically modified in vitro prior to transplantation, or alternatively, the cell can be directly modified in vivo following transplantation. Suhr, S. T. and Gage, F. H. (1993) *Arch. Neurol.* 50(11):1252–1268; Gage, F. H. et al. (1987) *Neuroscience* 23(3):795–807. Various methods are available for genetically modifying donor cells such as porcine neural cells, prior to implantation into a recipient subject. These methods include direct DNA uptake (transfection), and infection with viral vectors such as retrovirus, herpes virus, adenovirus, and adeno-associated virus vectors. Suhr, S. T. et al. (1993) *Arch. Neurol.* 50:1252–1268. Transfection can be effected by endocytosis of precipitated DNA, fusion of liposomes containing DNA or electroporation. Suhr, S. T. et al. (1993) *Arch. Neurol.* 50:1252–1268. Another method of transfecting donor cells is through the use of a "gene gun". In this method, microscopic DNA-coated particles are accelerated at high speeds through a focusing tube and "shot" or injected into cells in vitro (Klein, R. M. et al. (1992) *Biotechnology* 24:384–386; Zelenin, A. V. et al. (1989) *FEBS Lett.* 244:65–67) or in vivo (Zelenin, A. V. et al. (1991) *FEBS Lett.* 280:94–96). The cells close around the wound site and express genes carried into the cell on the particles.

Retroviral vectors typically offer the most efficient and best characterized means of introducing and expressing foreign genes in cells, particularly mammalian cells. These vectors have very broad host and cell type ranges, integrate by reasonably well understood mechanisms into random sites in the host genome, express genes stably and efficiently, and under most conditions do not kill or obviously damage their host cells. The methods of preparation of retroviral vectors have been reviewed extensively in the literature (Suhr, S. T. and Gage, F. H. (1993) *Arch. Neurol.* 50(11):1252–1258; Ray, J. and Gage, F. H. (1992) *Biotechniques* 13(4):598–603; Anderson, W. F. (1984) *Science* 226:401–409; Constantini, F. et al. (1986) *Science* 233:1192–1194; Gilboa, E. et al. (1986) *Biotechniques* 4:504–512; Mann, R. et al. (1983) *Cell* 33:153–159; Miller, A. D. et al. (1985) *Mol. Cell Biol.* 5:431–437; and Readhead, C. et al. (1987) *Cell* 48:703–712) and are now in common use in many laboratories. Other techniques for producing genetically modified cells are described in detail in PCT publication WO 95/27042. The contents of this application are incorporated herein by reference.

C. Method for Treating Neurological Deficits Due to Neurodegeneration in the Brain of a Xenogeneic Subject Using Porcine Striatal Cells One method disclosed herein for treating neurological deficits due to neurodegeneration in the brain of a xenogeneic subject includes introducing porcine striatal cells into an area of neurodegeneration in the brain of the subject. Preferred porcine striatal cells for use in the method of the invention are embryonic porcine striatal cells obtained from a lateral ganglionic eminence of the striatum. An embryonic pig from which the lateral ganglionic eminence cells of the striatum are obtained is of a gestational age at which the lateral and the medial ganglionic eminences can be morphologically distinguished from one another. Typically, these areas are morphologically distinct in an embryonic pig at between about days twenty (20) and about fifty (50), more preferably about days thirty (30) and forty (40), yet more preferably about days thirty-two (32) and about thirty-eight (38), and most preferably about thirty-four (34) and about thirty-six (36) days gestation.

To dissect a lateral ganglionic eminence from the brain of a fetal pig, the fetus is decapitated and the brain is extracted from the skull through a mid-sagittal incision. A parasagittal incision is created along the dorsal aspect of each hemisphere, exposing the medial and lateral ganglionic eminences in the ventrolateral wall of the lateral ventricle. The incision is then circumferentially completed, detaching the ventrolateral wall of the hemisphere (carrying the ganglionic eminences) from the rest of the brain. The external (cortical) surface of the detached wall of the hemisphere is then flattened against a solid support (e.g., the dissecting dish), thereby exposing the ganglionic eminences on the inner surface. The medial eminence is excised. The lateral ganglionic eminence, now isolated on the detached wall of the lateral ventricle, is then resected along its base (e.g., with curved microscissors) and transferred to an appropriate container (e.g., Petri dish) for dissociation.

Once the lateral ganglionic eminence is separated from the medial ganglionic eminence, the lateral ganglionic eminence cells are dissociated under conditions suitable for isolation of fetal porcine striatal cells. Under these conditions, the ingredients of the solution in which the cells are dissociated are adjusted to maintain the highest percentage of viable striatal cells. For example, in a preferred dissociation solution, Hank's balanced salt solution without calcium, magnesium, bicarbonate and phenol red is used, as these ingredients have been found to reduce the percentage of viable cells after dissociation. In addition, precautions are taken to reduce the amount of shear strain placed on the cells during dissociation. These precautions include minimizing the generation of air bubbles during dissociation and gently triturating the cells through pipettes with gradually decreasing pipette bore sizes. Preferably, the fetal pig brain and the dissected fetal pig brain parts are kept at room temperature rather than at 4° C. prior to dissociation.

Modified or unmodified porcine striatal cells, and in particular embryonic porcine striatal cells, can used to treat neurological deficits resulting from neurodegeneration, such as that which occurs in human subjects with Huntington's disease. Models of neurodegenerative diseases in several different animals have been developed in which the porcine striatal cells of the invention can be transplanted to assess their neuroregenerative capacity. For example, rat (Isacson, O. et al. (1985) *Neuroscience* 16:799–817), monkey (Kanazawa, I. et al. (1986) Neurosci. Lett. 71:241–246), and baboon (Hantraye, P. et al. (1992) *Proc. Natl. Acad. Sci. USA* 89:4187–4191; Hantraye, P. et al. (1990) *Exp. Neurol.* 108:91–014; Isacson, O. et al. (1989) *Exp. Brain Res.* 75(1):213–220) models of Huntington's disease have been described in which effective therapies are predictive of therapeutic efficacy in humans.

As an illustrative example, Hantraye et al. have generated a model of Huntington's disease in a baboon which has received ibotenic acid lesions in the caudate-putamen. Hantraye, P. et al. (1992) *Proc. Natl. Acad. Sci. USA* 89:4187–4191. The ibotenic acid-lesioned baboon displays a neuropathology of the caudate-putamen resembling that observed in post-mortem Huntington's disease studies in humans and a variety of drug-induced dyskinesias such as chorea-like movements after dopaminergic pharmacological activation. To assess therapeutic strategies, porcine striatal cells, and in particular embryonic porcine striatal cells obtained from a lateral ganglionic eminence, can be introduced into the lesioned area of the baboon caudate-putamen. Morphological and immunohistochemical studies can then be performed by conventional techniques to determine whether the porcine striatal implant has integrated, both morphologically and functionally, into the surrounding tissue. Behavioral tests can also be performed using standard techniques to confirm functional integration of the implant with the surrounding tissue. See e.g., Ellis, J. E. et al. (1992) *Exp. Neurol.* 115(3):376–387; Hantraye, P. et al. (1992) *Proc. Natl. Acad. Sci. USA* 89:4187–4191. Example III in the present application describes transplantation of striatal cells of the invention into lesioned brain areas of monkeys which resulted in correction of behavioral abnormalities.

In the case of epilepsy, there are both rat and monkey models in which effective therapies are predictive of therapeutic efficacy in humans. For example, rats which exhibit audiogenic seizures are commercially available. Thus, once the epileptic focus of these rats is located, cells of the present invention, preferably the striatal cells described herein, or other cell types, such as glial cells or muscle cells which have been genetically modified to produce GABA, can be transplanted at the epileptic focus. Decrease in seizure occurrence and degree can then be determined. Rat and monkey models of epilepsy can also be generated by kindling. The epileptic focus in these animals can then be located (e.g., the epileptic focus can be in, for example, the hippocampus) and cells of the invention, preferably striatal cells described herein or cells producing sufficient quantities of GABA, can be transplanted at the epileptic focus. Behavioral modifications resulting from such transplantation can then be determined.

D. Method for Treating Neurological Deficits Due to Neurodegeneration in the Brain of a Xenogeneic Subject Using Porcine Neural Cells Obtained from an Essentially Pathogen-Free Swine An other method disclosed herein for treating neurological deficits due to neurodegeneration in the brain of a xenogeneic subject includes introducing neural cells obtained from a pig which is essentially free from organisms or substances which are capable of transmitting infection or disease to the subject into an area of neurodegeneration in the brain of a xenogeneic subject. Swine which are essentially free from organisms or substances which are capable of transmitting infection or disease to a recipient subject are described above under the headings "A Porcine Neural Cell Isolated from an Essentially Pathogen-Free Swine" and "Method for Isolating a Porcine Neural Cell from an Essentially Pathogen-Free Swine". Neurodegeneration and areas of neurodegeneration are described above under the heading "Method for Treating Neurodegeneration in the Brain of a Xenogeneic Subject Using Modified Porcine Neural Cells". Preferred porcine neural cells obtained from swine which are essentially free from organisms or substances which are capable of transmitting infection or disease to a recipient subject include striatal, cortical, and mesencephalic cells described herein. To reconstitute neuron populations in areas of brain neurodegeneration, these cells can additionally be introduced into areas of neurodegeneration in a subject which is different from the area of the brain from which they are derived using standard techniques. See, e.g., Renfranz, P. J. et al. (1991) *Cell* 66(4):713–729.

Porcine striatal cells obtained from pigs which are essentially free from pathogenic organisms can be assessed for their neuroregenerative capacity in the models, such as Huntington's disease and epilepsy models described above under the heading "Method for Treating Neurological Deficits Due to Neurodegeneration in the Brain of a Xenogeneic Subject Using Porcine Striatal Cells". Similarly, porcine mesencephalic cells obtained from pigs which are essentially free from pathogenic organisms can be assessed for their neuroregenerative capacity in various animal models of mesencephalic neurodegeneration. For example, several animal models of Parkinson's disease have been generated in which effective therapies are indicative of therapeutic efficacy in humans. These animal models include three rat models (the rats having lesions in substantia nigral dopaminergic cells caused by treatment with 6-hydroxydopamine, 1-methyl-4-phenyl-1,2,3,6-tetrahydropyridine (MPTP), or surgical transection of the nigral striatal pathway) (See, e.g., Björklund, A. et al. (1982) *Nature* 298:652–654), a rhesus monkey model (the monkeys having lesions in substantia nigral dopaminergic cells caused by treatment with MPTP) (See, e.g., Smith, R. D. et al. (1993) *Neuroscience* 52(1): 7–16; Bakay, R. A. et al. (1985) *Appl. Neurophysiol.* 48:358–361; Zamir, N. et al. (1984) *Brain Res.* 322:356–360), and a sheep model (the sheep having lesions in substantia nigral dopaminergic cells caused by treatment with MPTP) (Baskin, D. S. et al. (1994) *Life Sci.* 54(7): 471–479). Therapeutic efficacy in any one of these models of Parkinson's disease is predictive of therapeutic efficacy in humans.

To assess therapeutic strategies, porcine mesencephalic cells, and in particular embryonic porcine mesencephalic cells obtained from the essentially pathogen-free pigs described above, can be introduced into these animal models. Morphological and immunohistochemical studies can then be performed by conventional techniques to determine whether the porcine mesencephalic implant has integrated, both morphologically and functionally, into the surrounding tissue. Behavioral tests can also be performed to confirm functional integration of the implant with the surrounding tissue. For example, a common behavioral test is a rotational symmetry model. Freed, W. J. et al. (1984) "Transplantation of catecholamine-containing tissues to restore the functional capacity of the damaged nigrostriatal pathway" in Sladek, J. R. et al. (eds.) Neural Transplants: Development and Function (Plenum Press, NY) 373–406. Briefly, animals, e.g., rats, with unilateral 6-hydroxydopamine lesions of the nigrostriatal pathway exhibit rotations in the direction of the lesioned side (ipsilateral) when injected with amphetamine. After successful transplantation, ipsilateral rotations are reduced and rotations in the opposite (contralateral) directed are often observed. Brundin, P. et al. (1987) *Progress in Brain Res.* 71:293–308. Rotational data is then recorded as net ipsilateral rotations, calculated by subtracting contralateral from ipsilateral rotations. Other examples of behavioral tests which can be used for assessment of integration of a mesencephalic implant include a grip strength test (Dunnett, S. B. et al. (1984) *Brain Res.* 215:147) and a water maze test (See e.g., Kopyov, O. V. et al. *Transplantation Proc.* 24(2): 547–548).

To assess therapeutic strategies, porcine cortical cells, and in particular embryonic porcine cortical cells obtained from the essentially pathogen-free pigs described above can be introduced into animal models of cortical dysfunction. Cortical lesions can be induced in experimental animals by a variety of substances including, for example, NMDA (Beal, M. F. et al. (1991) *J. Neuroscience* 11(1):147–158) Morphological and immunohistochemical studies can then be performed by conventional techniques to determine whether the porcine cortical implant has integrated, both morphologically and functionally, into the surrounding tissue. Behavioral tests can also be performed to confirm functional integration of the implant with the surrounding tissue.

E. Methods for Increasing Survival of Porcine Neural Cells Introduced into Areas of Neurodegeneration in the Brain of a Subject The porcine cells of the present invention can be incubated and/or treated at any stage in their preparation for transplantation, e.g., during dissection, trypsinization, dissociation and plating, and/or production of cell suspensions for transplantation, with a number of agents or factors which promote the survival, growth and differentiation of the cells in vitro and/or in vivo, i.e., in the recipient subject. In one embodiment, such agents or factors can be added at the site of transplantation in the recipient subject after the cells of the invention have been transplanted therein. In some instances, these agents can, for example, minimize or counteract detrimental effects on the cells resulting from the procedures used to prepare the cells for transplantation. For example, porcine cells, when isolated from the donor pigs and prepared for transplantation, may experience cellular trauma and/or hypoxia which lead to the production of reactive oxygen species (ROS) such as superoxide radical anion, hydrogen peroxide, and the hydroxyl free radical. Colton, C. A. et al. (1995) *Exp. Neurol.* 132:54–61. ROS are known to adversely affect neural function, most likely by affecting a variety of membrane and intracellular components including ion channels, membrane lipids, transport mechanisms such as the NA/K ATPase and Na+/glutamate exchange transport and cytosolic enzymes such as glutamine synthase. Colton, C. A. et al. (1995) *Exp. Neurol.* 132:54–61. Acute exposure of nerve terminals to ROS results in failure of neurotransmission. Colton, C. A. et al. (1991) *Free Rad. Res. Commun.* 14:385–393; Colton, C. A. et al. (1989) *Free Rad. Biol. Med.* 7:3–8. Long term exposure of nerve terminals to ROS results in retraction of neurites and eventually, neuronal death. Halliwell, B. et al. Free Radicals in Biology and Medicine, 2nd ed. (Clarendon Press, Oxford, England 1989). In addition, it is known that ROS provoke membrane lipid peroxidation, consequently reducing the survival of neural cells in the transplants.

To minimize and/or counteract the adverse effects of these types of oxidative stress during preparation for transplantation, the cells of the present invention can be incubated and/or treated with antioxidants at any stage during the preparation. Examples of such antioxidants include the enzyme antioxidants superoxide dismutase (SOD) and glutathione peroxidase (Colton, C. A. et al. (1995) *Exp. Neurol.* 132:54–61) which are commercially available from Boehringer Mannheim (Indianapolis, Ind.) and Sigma Chemical Company (St. Louis, Mich.), respectively, agents which promote glutathione formation, e.g. N-acetyl cysteine (NAC), also commercially available from Sigma, and other known antioxidants such as lazaroids, e.g., U-74389G and U-83836E, which are available from Upjohn (Nakao, N. et al. (1994) *Proc. Natl. Acad. Sci. USA* 91:12408–12412; Frodl, E. M. et al. (1994) *NeuroReport* 5:2393–2396). Antioxidant enzymes, such as SOD, scavenge ROS and prevent the reaction of superoxide with nitric oxide to form peroxynitrite anion, which has been shown to be toxic to cultured neurons. Nakao, N. et al. (1995) *Nature Medicine* 1(3):226–231. These enzymes can be incubated with the cells of the invention as described above. Another method of introducing these enzymes into the cellular preparations of the present invention is to genetically modify the cells to contain the nucleic acid encoding such enzymes. The genetically modified cells can then produce agents which enhance the survival, growth, and differentiation of the grafted cells in the recipient subject. For example, porcine cells of the invention can be transfected with the human gene for Cu/Zn superoxide dismutase, a pivotal enzyme in the detoxification of oxygen free radicals, (Nakao, N. et al (1995) *Nature Medicine* 1(3):226–231). These transfected cells then express SOD and, consequently, efficiently detoxify ROS generated during tissue preparation and implantation to thereby increase graft survival.

Lazaroids are 21-aminosteroids that lack glucocorticoid activity and are specifically designed to localize within cell membranes and inhibit lipid peroxidation (stabilize membranes by inserting their lipophilic portion into the phospholipid bilayer (Nakao, N. et al. (1994) *Proc. Natl. Acad. Sci. USA* 91:12408–12412; Frodl, E. M. et al. (1994) *NeuroReport* 5:2393–2396). Lazaroids are also known to scavenge free radicals, in particular, hydroxyl radicals. Other examples of antioxidants which can be added to the cell cultures and cell suspensions include TGFβ (Prehn, J. H. M et al. (1994) *Proc. Natl. Acad. Sci. USA* 91:12599– 12603), vitamin E (Nakao, N. et al. (1995) *Nature Medicine* 1(3): 226–231), vitamin C, beta carotene, and other compounds which scavenge ROS, inhibit the production of ROS, and/or inhibit lipid peroxidation.

In addition, the oxidative environment of the cells in vitro can be modified to inhibit cellular oxidative stress. For example, during preparation of the porcine cells for transplantation, the partial pressure of oxygen in the cells' environment can be decreased from the normal oxygen partial pressure, i.e., approximately 150 torr $O_2$, to a decreased oxygen partial pressure, i.e., 38 torr $O_2$ (about 5% $O_2$). This method of decreasing oxidative stress can be combined with treatment of the cells with one or more of the above-described antioxidants. For example, the combination of the partial oxygen pressure of 38 torr (e.g., 5% $O_2$) and treatment with NAC is effective for promoting survival of TH+ neurons. Colton, C. A. et al. (1995) *Exp. Neurol.* 132:54–61.

During the hypoxic conditions associated with the preparation of the cells of the invention for transplantation, the release of excitatory amino acids in the extracellular space stimulates N-methyl-D-aspartate (NMDA) receptors to increase the activity of nitric oxide synthase (NOS) which in turn results in increased biosynthesis of nitric oxide (NO). Nitric oxide is a neurotransmitter which can be toxic under conditions of excessive formation. Dawson, T. et al. (1995) *The Neuroscientist* 1(1):7–17. The toxic effects of NO occur through an interaction with the superoxide anion to form peroxynitrite, a highly reactive molecule which is able to nitrosylate proteins as well as initiate lipid peroxidation. Peroxynitrite also spontaneously decomposes to the hydroxyl and $NO_2$ free radicals, which mediate a variety of toxic effects. Dawson, T. et al. (1995) *The Neuroscientist* 1(1):7–17. Inhibitors of NOS, such as gangliosides, FK506, and cyclosporine A (Dawson, T. et al. (1995) *The Neuroscientist* 1(1):7–17), can be added to the cell preparations to inhibit the production of NO, thereby decreasing the production of peroxynitrite and its derivatives. Superoxide dismutase is another agent which can decrease the adverse effects of overproduction of NO and the toxic effects it mediates. Dawson, T. et al. (1995) *The Neuroscientist* 1(1):7–17.

Trauma and its associated adverse effects, e.g., membrane peroxidation, free radical induced cell damage (González-Garcia, M. et al. (1995) *Proc. Natl. Acad. Sci. USA* 92:4304–4308; Zhong, L-T. et al. (1993) *Proc. Natl. Acad. Sci. USA* 90:4533–4537), induced by preparation of the cells of the invention for implantation can also result in programmed cell death (apoptosis) of the transplanted cells. To reduce the occurrence of apoptosis in the transplanted cells, the porcine cells of the invention can be transfected with nucleic acids encoding antiapoptotic gene products such as the bcl-2 (Talley, A. K. et al. (1995) *Mol. Cell Biol.* 15(5):2359–2366; Merry, D. E. et al. (1994) *Development* 120:301–311; Prehn, J. H. et al. (1994) *Proc. Natl. Acad. Sci. USA* 91:12599–12603; Zhong, L-T. et al. (1993) *Proc. Natl. Acad. Sci. USA* 90:4533–4537), bcl-xL, the bcl-xβ (González-Garcia, M. et al. (1995) *Proc. Natl. Acad. Sci. USA* 92:4304–4308), and/or the crmA (Talley, A. K. et al. (1995) *Mol. Cell Biol.* 15(5):2359–2366) gene product. These gene products have been shown to inhibit programmed neural cell death. In addition, the transfected porcine cells of the invention can be treated with agents which upregulate the expression or function of these gene products, e.g., TGFβ1 and TGFβ3 which upregulate the expression of bcl-2 (González-Garcia, M. et al. (1995) *Proc. Natl. Acad. Sci. USA* 92:4304–4308; Prehn, J. H. et al. (1994) *Proc. Natl. Acad. Sci. USA* 91:12599–12603) to augment the neuroprotective effect of the antiapoptotic gene products produced by the cells. Other factors, such as nerve growth factor (NGF) and platelet-derived growth factor (PDGF) have been found to have antiapoptotic activity (Zhong, L-T. et al. (1993) *Proc. Natl. Acad. Sci. USA* 90:4533–4537). The cells of the invention, therefore, can also be transfected with nucleic acid encoding these factors. Enzyme antioxidants, such as superoxide dismutase and catalase (Bonfoco, E. et al. (1995) *Proc. Natl. Acad. Sci. USA* 92:7162–7166), and other antioxidants, such as NAC (Talley, A. K. et al. (1995) *Mol. Cell Biol.* 15(5):2359–2366) can also be used to prevent cells of the invention from undergoing programmed cell death during preparation for transplantation.

To further promote the survival of the porcine cells of the invention in the recipient subject, the cells can be transplanted in conjunction with an angiogenic agent or transfected with nucleic acid encoding an angiogenic agent. Upon transplantation, the angiogenic agent promotes the ingrowth of blood vessels into the porcine neural graft. As a result of this vessel ingrowth, the cells of the graft obtain sufficient nutrients to proliferate and survive within the recipient subject. Many growth factors exhibit angiogenic activity. For example, vascular endothelial growth factor (VEGF) (Drake, C. J. et al. (1995) *Proc. Natl. Acad. Sci. USA* 92:7657–7661; Sharma, H. S. et al. (1995) *Biochim. Biophys. Acta* 1260:235–238; Millauer, B. et al. (1993) *Cell* 72:835–846), which occurs in four forms due to alternative splicing of its mRNA, is a potent endothelial mitogen. PDGF, acidic and basic fibroblast growth factor (FGF) (Drake, C. J. et al. (1995) *Proc. Natl. Acad. Sci. USA* 92:7657–7661), epidermal growth factor (EGF), and K-FGF (Brüstle, O. et al. (1992) *Oncogene* 7(6):1177–1183) also possess angiogenic activity and can be used in the methods of the invention to encourage blood vessel ingrowth into the transplanted cells of the invention.

Other factors, such as neurotrophic factors, which contribute to neural development, nerve fiber formation, and maintenance of neurons can be added to the cells of the invention in vitro during preparation for transplantation and/or to the cell suspension itself for introduction into the recipient subject along with the cells of the invention. The cells of the invention can also be genetically modified to produce such neurotrophic factors as described herein. The neurotrophic factor which is added to the cells of the present invention can be selected based on the presence of its receptors on the cells which are to be transplanted. For example, mesencephalic cells possess receptors for the following neurotrophic factors: glial cell line-derived neurotrophic factor (GDNF) (Tomac, A. et al. (1995) *Nature* 373:335–339; Beck, K. D. et al. (1995) *Nature* 373:339–341; Poulson, K. T. et al. (1994) *Neuron* 13:1245–1252; Strömberg, I. et al. (1993) *Exp. Neurol.* 124:401–412), which promotes the survival of, morphological differentiation of, and high affinity dopamine uptake in mesencephalic cells; brain-derived neurotrophic factor (BDNF) (Tomac, A. et al. (1995) *Nature* 373:335–339; Hyman, C. et al. (1994) *J. Neurotics.* 14(1):335–347); ciliary neurotrophic factor (CNTF) (Hag, T. et al. (1993) *Proc. Natl. Acad. Sci. USA* 90:6315–6319), which prevents axotomy induced degeneration of mesencephalic cells; midkine (Kikuchi, S. et al. (1993) *Neurosci. Lett.* 160:9–12), which promotes the survival and differentiation of mesencephalic cells; EGF (Casper, D. et al. (1991) *J. Neurosci. Res.* 30:372–381; Knusel, B. et al. (1990) *J. Neurosci.* 10:558–570), which increases survival and maturation of mesencephalic cells; insulin-like growth factor I and II and insulin (Knusel, B. et al. (1990) *J. Neurosci.* 10:558–570); acidic FGF (Engele, J. et al. (1991) *J. Neurosci.* 11:3070–3078); basic FGF (Ferrari, G. et al. (1989) *Devel. Biol.* 133:140–147), which induce a significant increase in the number of neurite-bearing cells as well as in the degree of their fiber network; neurotrophin-3 (NT-3) and neurotrophin 4/5 (NT-4/5) (Hyman, C. et al. (1994) *J. Neurosci.* 14(1):335–347); and transforming growth factor-β2 (TGFβ2) and transforming growth factor-β3 (TGFβ3) (Poulson, K. T. et al. (1994) *Neuron* 13:1245–1252).

Neurotrophic factors which promote the survival of striatal cells can be selected based on the presence of receptors on the striatal cells. Receptors for basic FGF (Ferrari, G. et al. (1989) *Devel. Biol.* 133:140–147), BDNF (Hyman, C. et al. (1994) *J. Neurosci.* 14(1):335–347), NT-3 and NT-4/5 (Hyman, C. et al. (1994) *J. Neurosci.* 14(1):335–347) can be found on striatal cells. Thus, in one embodiment, the striatal cells of the invention can be transfected with the nucleic acids encoding one or more of these factors. In another embodiment, one or more of these factors can be added to the preparation of striatal cells prior to transplantation. These neurotrophic factors enhance the survival of the cells of the invention, specifically the striatal cells of the invention, in the recipient subject. Similarly, neurotrophic factors which exhibit specificity for cortical cells, and consequently, which can be used to promote the survival of such cell upon engraftment into a recipient subject, include nerve growth factor (NGF) (Lindsay, R. M. et al. (1994) *TINS* 17(5):182–190), which prevents, for example, atrophy of axotomized forebrain cholinergic neurons; BDNF, and NT-3 and NT-4/5 (Lindsay, R. M. et al. (1994) *TINS* 17(5): 182–190).

In another embodiment, the neurotrophic factors described herein can be used together or in combination with other compounds, such as neurotransmitters, to augment their neurotrophic effects. For example, the combination of either acidic or basic FGF and a catecholamine, when contacted with the appropriate neural cells, simultaneously or sequentially, can induce tyrosine hydroxylase expression. Du, X. et al. (1995) *J. Neurosci.* 15(7):5420–5427. In addition, it is contemplated that various combinations of neurotrophic factors described herein can act synergistically and, therefore, can be used together to promote survival of the transplanted cells of the invention.

Certain drugs also possess neurotrophic activity. Examples of such drugs include FK506 and cyclosporin A (Lyons, W. E. et al. (1994) *Proc. Natl. Acad. Sci. USA* 91:3191– 3195) which block the neurotoxicity elicited by glutamate acting at N-methyl-D-aspartate (NMDA) receptors by, for example, augmenting phosphorylated levels of NOS. As phosphorylated NOS inhibits its catalytic activity, these drugs effectively reduce NO formation and prevent the neurotoxic effects of NMDA on these cells. Other drugs which possess neurotrophic activity and can be used in the present invention are those small molecules which bind to the same binding proteins as FK506 and/or cyclosporin A and, therefore, mediate similar neuroprotective effects. Lyons, W. E. et al. (1994) *Proc. Natl. Acad. Sci. USA* 91:3191–3195.

It is specifically contemplated herein that combinations of one or more of the above-described agents and factors can be used to promote survival of the cells of the invention prior to or after the cells are transplanted into recipient subjects. For example, cells of the present invention can be contacted with one or more of the agents or factors described herein to promote survival of the cells in vitro and/or in vivo. In another embodiment, the cells of the invention can be transfected with the nucleic acid of one or more of the agents or factors described herein and also contacted with one or more of the agents or factors described herein. Moreover, although many of the neurotrophic factors described herein are specific for a particular cell type, the association of these factors with such a cell type does not exclude the use of that factor with a different cell type. Treatment of the cells of the invention with the agents or factors described herein can occur simultaneously or sequentially.

The present invention is further illustrated by the following examples which in no way should be construed as being further limiting. The contents of all cited references (including literature references, issued patents, published patent applications, and co-pending patent applications) cited throughout this application are hereby expressly incorporated by reference.

EXAMPLES

Examples I

Transplantation of Porcine Striatal Cells into Lesioned Rat Brains and Histological Examination of the Transplanted Cells Experimental Design In a series of experiments seventy-five adult male Sprague-Dawley rats (300–350 gm) received excitotoxic lesions of the neostriatum, followed 7 days later by intrastriatal transplantation of cells from the striatal anlage of fetal pig brains. The transplanted rats were immunosuppressed with cyclosporin-A and their grafts were allowed to mature for 1 to 4 months post-implantation. The rats were then sacrificed for histological analysis.

Fetal Pig Brain Dissection Procedure

Figure 6C:
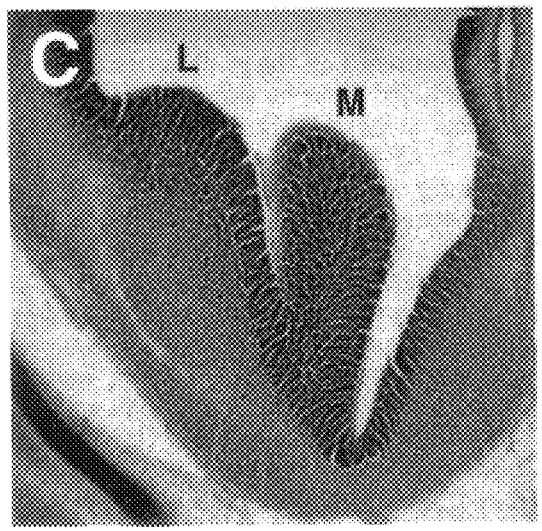
Figure 6D:
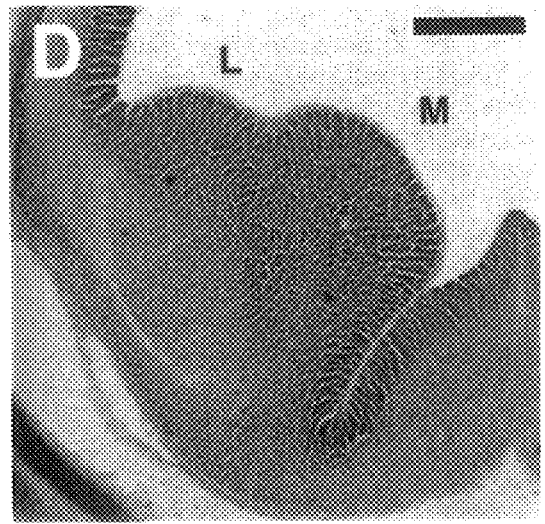

Twenty-two to fifty days after insemination, pregnant Yorkshire pigs (with a normal gestational period of 115 days) were euthanized following standard veterinary procedures at Tufts School of Veterinary Medicine (Grafton, Mass.). Uterine horns were removed and stored on ice for transport to a sterile laboratory facility (Diacrin, Inc., Charlestown, Mass.) where fetuses were delivered from their uterine pouches and transferred to sterile phosphate buffered saline (PBS). Crown-to-rump-length (CRL) was measured to verify comparable gestational ages (FIG. 6A). Under a laminar flow hood, fetuses were decapitated and whole brains were removed through a mid-sagittal incision. Dissection of the fetal brain was performed in PBS under a dissecting microscope to expose the ganglionic eminences in the basal telencephalon (FIG. 6B). Pig fetuses between 30 and 40 days of gestational age (E30–40) exhibited a distinct division between the lateral ganglionic eminence (LGE) and the medial ganglionic eminence (MGE) in the base of the telencephalon. This stage of fetal brain development is morphologically similar to that seen in E15 rats. This allowed selective excision of the LGE, excluding both the MGE and the underlying cortex (following the procedure of Pakzaban et al. (1993) *Exp. Brain Res.* 97(1):13–22). FIG. 6B diagrammatically depicts the location of the lateral ganglionic eminence in the fetal brain. The location and appearance of the LGE and MGE in an E35 fetal pig brain is shown in photomicrographs in FIGS. 6C and 6D. Fetuses younger that E30 were examined but found to be too immature in telencephalic development to distinguish the ganglionic eminences for dissection, whereas, in fetuses older than E40, the morphological distinction between the LGE and MGE was not discernible.

Following dissection, each resected LGE fragment was transferred to a collecting dish containing Hank's balanced salt solution (HBSS; Sigma Chemical Co., St. Louis, Mo.) without calcium, magnesium, bicarbonate, and phenol red and kept at room temperature until the cell are to be dissociated. The presence of bicarbonate has been found to reduce the percentage of viable cells after dissociation. Tissue fragments derived from both hemispheres of all fetal brains of a litter were pooled. The tissue was incubated in 0.5% trypsin-EDTA in HBSS (Sigma) and DNase at 37° C. for 15 minutes, then washed three times with HBSS, then gently triturated through the tips of fire-polished Pasteur pipettes of progressively smaller diameter until a milky suspension was obtained. The use of Pasteur pipettes of progressively smaller diameter reduces the shear strain placed on the cells during dissociation. An example of the gradual change in pipette bore for dissociation is as follows: tissue pieces are first dissociated with a Pasteur pipette that has been fire polished, but that has a normal size opening. The pieces of fetal brain tissue are pipetted carefully up and down avoiding the introduction of air bubbles, until there is no change in the turbidity of the dissociation media (i.e., no additional cells are being released from the pieces of tissue). At this point, a new fire polished Pasteur pipette with a smaller opening is substituted for the pipette with the larger opening. Generally, a total of 4 Pasteur pipettes of progressively smaller pipette tip openings are used to dissociate the cells. It is important to avoid using a pipette with too small of a tip opening. Thus, progression to a pipette with a smaller tip opening should not be attempted until further dissociation is required but is not occurring using the present tip size. Removal of small clumps of tissue during dissociation also minimizes the shear strain placed on the cells. In addition, human recombinant DNaseI, 100 units/ml, is included during the dissociation to prevent unwanted clumping of cells. Cell-concentration and viability were determined using a hemocytometer and acridine orange/ethidium bromide staining under UV epi-illumination on a fluorescence microscope (Brundin et al. (1985) *Brain Res.* 331:251–259).

Lesion, Transplantation and Perfusion Procedures

Rats were anesthetized with pentobarbital (65 mg/kg, i.p.) and placed in a Kopf stereotaxic frame. Through a small incision, a burr hole was created in the skull and a 1 µl injection of quinolinic acid (120 nM) was delivered unilaterally (n=59) or bilaterally (n=16) into the neostriatum (stereotaxic coordinates in relation to bregma: anterior= ±1.0, lateral=±2.5, ventral=−4.5, incisor bar=−2.5) using a 5 µl Hamilton syringe. Seven days later each lesioned rat was reanesthetized according to the same protocol and received a fetal pig cell suspension implant at the same stereotaxic coordinates. Five µl of suspension were injected containing between 10,000 to 200,000 viable cells (depending on the experiment, see Results). The cell suspension was infused in 1 µl increments over 10 minutes through a 5 µl Hamilton syringe fitted with a 22-S gauge needle (ID=0.41 mm), allowing an additional 2 minutes for the final injection pressure to equilibrate before slowly withdrawing the needle.

Starting the day of transplantation, rats were immunosuppressed with cyclosporin-A (10–15 mg/kg, s.c. daily) for the duration of the experiment to prevent graft rejection (Brundin et al. (1985) *Brain Res.* 331:251–259). Survival time post-transplantation varied from 5 weeks to 16 weeks. Under deep pentobarbital anesthesia (130 mg/kg, i.p.), rats were transcardially perfused with 100 ml heparin-saline (0.1% heparin in 0.9% saline) followed by 200 ml 4% paraformaldehyde in 0.1 M phosphate buffered saline, pH 7.4 (PBS).

Histological Preparation, Staining, and Immunohistochemical Procedures

Rat host brains were post-fixed for 6–8 hours in 4% paraformaldehyde in PBS and then immersed for 1–3 days in 30% sucrose in PBS before 40 µm frozen microtome sections were cut. Sections were divided into 6–8 series and stored in PBS at 4° C. Separate series were processed for either Nissl staining (cresyl violet acetate), acetylcholinesterase (AChE) histochemical staining, and ABC immunohistochemistry (Vector Labs, Burlingame, Calif.). Immunohistochemical markers used in this study include antibodies to: dopamine and cyclic AMP regulated phosphoprotein, 32 kD (DARPP-32; kindly provided by Dr. Paul Greengard, Rockefeller University), glial fibrillary acidic protein (GFAP; Boehringer Mannheim Biochemica, Indianapolis, Ind.), microtubule associated protein 1b (MAP1B; kindly provided by Thomas Shea, McLean Hospital, Belmont, Mass.); pig cluster of differentiation antigen 44 (CD44), and bovine-neurofilament, 70 kD (NF70; Biodesign, Inc., Kennebunkport, Me.).

Characterization of Species-specific Cell Markers for CD44 and NF70

Two candidate antibodies deemed likely to bind pig brain antigens were tested for species-specificity: antibodies to CD44 and NF70. In the adult pig forebrain, CD44-immunoreactivity (CD44-IR) is found in all major white matter tracts, including the corpus callosum and fiber bundles of the internal capsule, but it is not found in the gray matter of the cerebral cortex or corpus striatum. Within white matter structures, CD44-IR labels filamentous processes that extend along bundles of myelinated axons. Control tests for nonspecific binding to normal adult rat brains and in rats with excitotoxic striatal lesions alone, show that anti-porcine-CD44 does not cross-react with rat antigens under corresponding experimental conditions.

In the adult pig forebrain, bovine-NF70-immunoreactivity (NF70-IR) is found in both white and gray matter structures. NF70-IR axons form bundles within myelinated fiber tracts and are dense, though lightly stained, within gray matter structures, however, NEF70-IR neural somata are rarely observed. Control tests for nonspecific binding to normal adult rat brains and adult rats with excitotoxic striatal lesions alone, show that anti-bovine-NF70 does not cross-react with rat antigens under corresponding experimental conditions.

Effects of Initial Cell Dosage on Graft Volume

Given the differences in size of adult pig and rat brains and of the corpus striatum within each, the number of fetal rat cells shown to produce allografts of appropriate size for the rat striatum could not be relied upon to produce porcine xenografts of similar size. It was therefore necessary to perform a preliminary study of the relationship between the dosage of donor cells implanted and the size of the resulting graft, to avoid any untoward effects of graft overgrowth and to provide results that would be comparable to rat allograft studies.

Figure 7A:
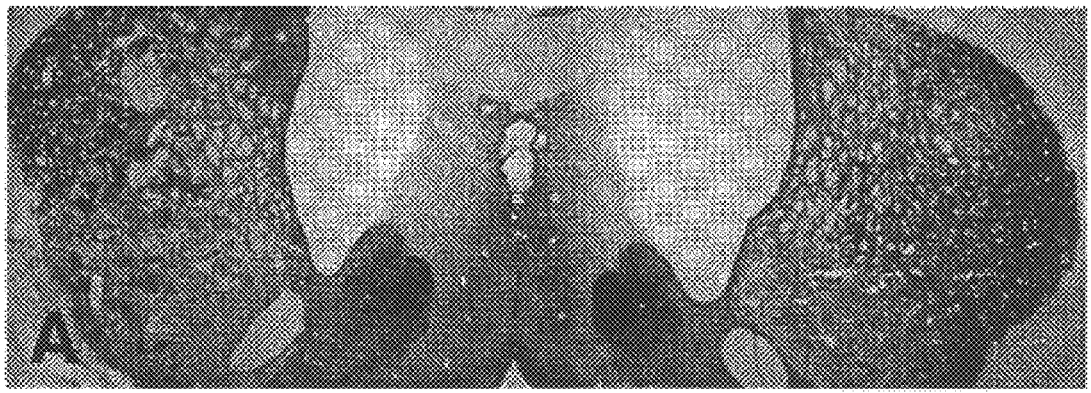
Figure 7B:

Rat hosts were bilaterally implanted with different doses of pig LGE cell suspension. Eight rats received 100K viable cells implanted into the right and 50K viable cells implanted into the left striatum, and 8 rats received 200K viable cells implanted into the right and 10K viable cells implanted into the left striatum. The volumes of resulting grafts were measured after 8 weeks of growth (FIGS. 7A–7C). Volumetric comparisons of pooled samples for each cell dosage reveal an increasing dose-response relationship. The 200K cell grafts had a mean volume of 5.5 mm$^3$ and filled a large fraction of the lesioned portion of the rat striatum but were not hypertrophic (FIG. 7A, left). All other doses produce grafts smaller than the lesioned region of the striatum. Although these grafts were still immature at time of sacrifice, their size was judged to be well within the range of comparable rat allografts. Therefore, in all subsequent experiments cell doses within the range of 100K and 200K cells were used.

Development of Xenograft Morphology at Different Graft Ages

After 4 to 5 weeks of development post-implantation (roughly corresponding to the midpoint of gestation for cells in a normal pig brain), pig xenografts are comparatively homogeneous in cytoarchitecture. They are composed of predominantly small and tightly packed somata that form a column surrounding the needle track, and only small portions of the graft stain for AChE activity. After 8 weeks of development, pig xenografts have expanded into the lesioned striatum and exhibit cytoarchitectonic heterogeneity. Nissl staining shows that the graft is segregated into distinct small versus large-cell regions and these correspond to AChE-rich and AChE-poor regions, respectively, as seen in adjacent AChE-stained sections (described in more detail below). At this stage AChE-rich regions were measured to be from 25% to 40% of the total graft volume. After 16 weeks of development, a larger fraction of the graft is composed of clusters of large neural somata that are also AChE-rich and the graft has expanded into the lesioned portion of the striatum, including cells of different morphologies and densities that are organized into distinct subregions.

Cytoarchitectural and Immunohistochemical Characteristics of Porcine Xenografts

Evidence that the antibody to porcine CD44 selectively binds to pig-derived glial tissue of the graft is provided by comparison of structures stained with antibodies to CD44 and GFAP in adjacent sections through the graft, as well as by the morphological appearance of CD44-IR cells. In the vicinity of 8-week-old porcine xenografts, antibody to GFAP stains both rat host astrocytes surrounding the graft and pig glial cells within the graft. Consequently, the graft-host boundary is ambiguous, though the comparatively higher GFAP-immunoreactive (GFAP-IR) cell density within the graft distinguishes it from the decreasing density of GFAP-IR cells progressively further into the surrounding lesioned striatum. Although GFAP-IR is minimal in the normal adult rat striatum (and is essentially absent in the contralateral normal striatum of the brains of grafted animals), GFAP expression is known to be up-regulated in response to injury (Bignami, A. et al. in Advances in Cellular Neurobiology, Federoff, S. and Hertz, L. eds. (Academic Press, NY 1980), 1:285–310; Bjorklund, A. et al. (1986) *Brain Res.* 371:267–277; Coffey, P. J. et al. (1990) *Neuroscience* 35:121–132; Isacson, O. et al. (1987) *Neuroscience* 20:1043–1056) and likely accounts for the considerable numbers of these cells surrounding the graft. In contrast, CD44-IR is largely confined to the graft at this stage of development. The major region of porcine CD44-IR corresponds closely to the graft volume as identified in adjacent Nissl and AChE stained sections and corresponds to the region of densest GFAP-IR. CD44 stained filaments can be seen extending beyond the perimeter of the graft, but for the most part, the surrounding lesioned and normal regions of the host striatum contain few CD44-IR structures. The few isolated CD44-IR cells that can be found separated from the body of the graft are morphologically quite similar to cells that are immunoreactive for GFAP, exhibiting an astrocytic-like appearance. CD44-IR is also seen outside the striatum in adjacent white matter tracks, mostly in the form of irregularly shaped filaments.

One of the most striking cytoarchitectonic features of these grafts is the grouping of large neurons into clusters, visible in Nissl-stained sections. These clusters range in diameter from approximately 250 to 600 $\mu$m, and are often surrounded by a comparatively cell-free annulus that separates them from a surrounding region of the graft containing smaller and more densely packed cells. Although there are undoubtedly glial cells associated with these neural clusters, as indicated by the presence of small Nissl-stained nuclei, they are minimally stained with either of the two glial markers used in this study, GFAP and CD44. AChE histochemical staining in adjacent sections also exhibits a rather precise correspondence with this cell clustering. Clusters of large neural somata are located in regions that stain most darkly for AChE. There is often a sharp boundary between these regions of dark AChE staining and the AChE-poor surround that corresponds with the cell free annulus enclosing the neural cluster. In contrast, an inverse staining pattern is exhibited in adjacent sections stained for either GFAP or CD44. The same clusters of neurons that are AChE-rich are essentially negative for either GFAP-IR or CD44-IR, in comparison to surrounding regions that stain densely for both. The boundary distinguishing an AChE-rich cluster from the CD44-rich surrounding graft can be quite distinct. These two markers divide the graft into two complementary tissue types that are either neuron-rich or glia-rich tissues.

The large neurons within these clusters are also DARPP-32-immunoreactive (DARPP-32IR); however, at early stages (i.e., 8 weeks), there is also DARPP-32 staining of fibers in the regions surrounding the clusters. At later stages (i.e., 16 weeks), both AChE staining and DARPP-32-IR become more intense and better co-localized. In addition, differences in staining of neural clusters, the surrounding graft, and the lesioned host striatum become greater. By 16 weeks post-implantation both the cells and the neuropil within neural clusters are strongly AChE-positive and DARPP-32-IR.

Axonal Development in Porcine Xenografts

The availability of an antibody that binds an epitope of pig but not rat neurofilament makes it possible to directly trace the development and extension of graft axons. NF70 immunoreactivity of pig axons in the rat is highly specific and allows even single axons to be traced a considerable distance within the plane of section. Few NF70-IR fibers are found within 5 week old grafts, but by 8 weeks a dense plexus of NF70-IR fibers fills most of the volume of the graft. In contrast to the dense distribution of axons within the graft, they are in much lower density just outside of the graft in the adjacent lesioned host striatum. This gives the impression of a graft boundary that is coextensive with the sharp boundary between pig CD44-IR cells and the host striatum. This boundary is not preferentially correlated with either gray or white matter host tissues.

The pattern of NF70 immunoreactivity parallels that of another light neurofilament associated protein, microtubule associated protein 1B (MAP1B), which is expressed at high levels during early neural development but is down-regulated in later stages of axonal development (Fischer, I. and Romano-Clarke, G. (1990) *Mol. Cell Neurosci.* 2:39–51; Fliegner, K. H. and Liem, R. K. H. (1991) *Int. Rev. Cytol.* 131:109–167; Ulola, L. et al. (1993) *J. Neurochem.* 61:961–972. MAP1B-IR fibers were not observed in normal adult rat brains or in regions of grafted brains distant from the graft. Both NF70 and MAP1B antibodies demonstrate dense overlapping axonal labeling within the volume of 8 week old grafts and a few fibers extending into the surrounding host neuropil and adjacent white matter. The highly correlated staining of these two antibodies further corroborates the axonal specificity of NF70. In addition, the comparative density of MAP1B-IR fibers is an indication of the comparative immaturity of porcine grafts at this stage.

Comparison of adjacent Nissl-stained, AChE-stained, and NF70-immunostained sections of the same graft shows that axons preferentially extend into graft regions that are filled with densely packed small cells that do not stain for AChE. This complementarity is clear in 8 week old grafts that contain numerous neural cell clusters interspersed within predominantly glial cell regions. Patterns of AChE-staining and NF70 immunoreactivity in the vicinity of neural cell clusters in two 8 week old grafts are observed. There may be some incursion of NF70-IR fibers into the darkly AChE-stained annulus around the neural somata cluster, but not into the center of the cluster. Lack of NF70-IR fibers in the vicinity of neural somata reflects localized expression of NF70 to more distal portions of the axon that are not proximal to the soma, and it also indicates that growing striatal graft axons tend not to re-enter regions of the graft that contain clusters of comparatively mature striatal-like neurons.

In comparison with the extensive proliferation of NF 70-IR fibers within the body of a graft, extension of fibers beyond the graft into the host brain is sparse. Beyond the interface between donor and host cells there is a marked reduction of axonal density. This also corresponds with a reduction of CD44-IR cells in the surrounding lesioned striatum. However, a few axons can be seen coursing through the adjacent striatal and pallidal regions, extending to distances of up to 500 μm from the graft boundary. The largest numbers of axons projecting out of the graft and into adjacent gray matter structures extend medially into the globus pallidus and ventrally into the ventral pallidum, particularly in the vicinity of the anterior commissure.

In contrast to the sparse extension of axons into the adjacent host striatum and short projections into adjacent pallidal regions, a considerable proportion of the graft axons extending beyond the immediate boundaries of the graft are found in white matter tracts, including internal capsule fiber bundles penetrating the striatum adjacent to the graft, the corpus callosum and the anterior commissure. Donor axons growing into myelinated fiber tracts tend to be oriented parallel to the trajectory of host fibers within those tracts and extend further from the graft than those that extend through gray matter structures.

The majority of the porcine CD44-IR structures are filamentous in form, though a fair number of structures with astrocytic appearance can also be observed. Although there are few porcine CD44-IR cells or cell processes in the region of the host striatum surrounding a graft, there at comparatively large numbers of porcinc CD44-IR fibers in the corpus callosum surrounding the transplanted striatum. The density of CD44-IR structures within the corpus callosum decreases with distance from the graft but some can be observed in the middle of the contralateral corpus callosum. The morphology and orientation of CD44-IR fibers within host white matter tracts is similar to what is observed within white matter tracts in the adult pig brain.

Comparison of adjacent sections through the corpus callosum processed for CD44 and NF70 indicates that there is a close correspondence between regions that contain donor-derived glial and neural fibers. Pioneering glial and axonal fibers grow out from the graft into these same host brain structures with corresponding densities. Both are comparatively sparse in surrounding host gray matter and more densely represented in nearby white matter tracts.

Figure 8:
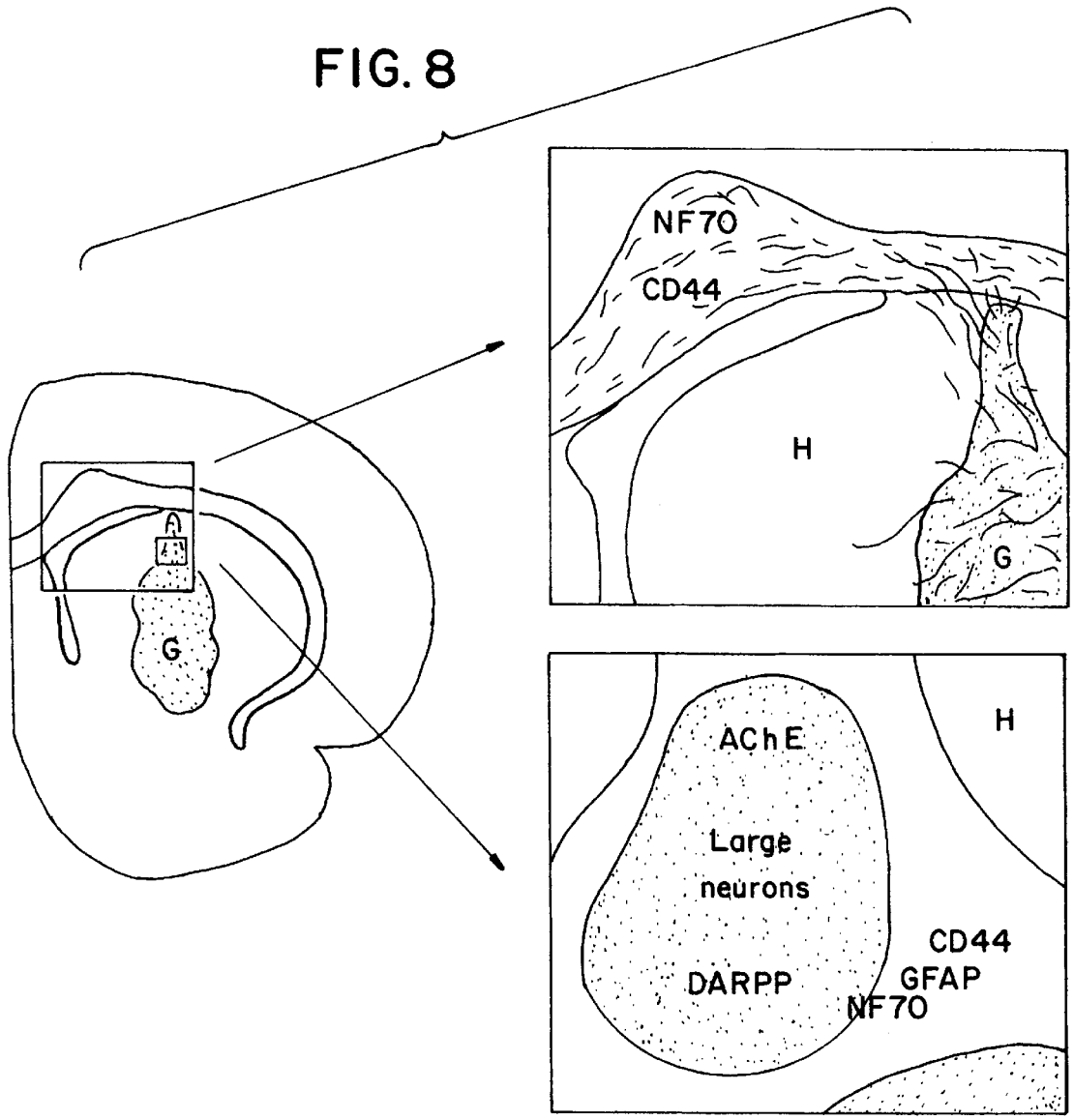
FIG. 8 is a summary diagram schematically depicting the relationships among graft cells and between graft and host cells observed in this study. Observed relationships between graft cells and host brain structures are depicted in the upper right box, including the preferential extension of graft axons and glial fibers into host white matter tracts and the association of graft axons with graft glia outside the graft. Observed relationships between different cell types within the graft are depicted in the lower right box, including the segregation of GFAP- and CD44-IR glia-rich regions from AChE-positive DARPP-positive, neuron-rich zones. Also depicted is the preference of graft axons for the glial regions of the graft.

Use of species-specific antibodies to graft glial and axonal proteins of the xenogeneic donor species enables a number of otherwise ambiguous cellular inter-relationships and donor-host cell interactions to be visualized and studied. After 8 to 16 weeks, porcine striatal grafts have developed regional heterogeneity, characterized by regions that exhibit one of two general patterns of cell architecture and staining: a) regions that are AChE-rich and contain clusters of DARPP-32IR neurons contrasted with b) regions that are AChE-poor and contain densely-packed, small cells that stain strongly for the glial markers GFAP and CD44. NF70-IR axons are found to densely fill the AChE-poor glia-rich portions of the graft. Beyond the graft perimeter, there is a significant reduction of the density of CD44-IR and NF70-IR structures; however, they are both found to extend into adjacent pallidal regions and into the corpus callosum, anterior commissure and internal capsule fiber bundles. These relationships are summarized by the schematic drawing in FIG. 8.

Comparison of Porcine Xenografts to Rat Allografts

As rat allografts develop, there is both a progressive increase in the intensity of AChE histochemical staining and an increase in the proportion of AChE-rich as compared to AChE-poor territories within the graft (Labandeira-Garcia, J. L. et al. (1990) *Neuroscience* 42:407–426. This trend is also observed in the porcine xenografts. In porcine xenografts that are 5 weeks old, there is very little indication of AChE activity, but by 8 weeks there are a number of AChE-rich regions within the graft, though a large fraction of the graft volume remains AChE-poor. By 16 weeks (the longest survival period in this study), the AChE-rich proportion of the graft predominates and some regions stain as darkly for AChE as does adult striatal tissue. DARPP-32-IR also develops progressively, from comparatively light-staining soma and diffuse light-staining neuropil in 8 week old grafts to darkly-staining neural somata and localized dense-staining neuropil in 16 week old grafts.

The time-course of the increase in both AChE staining and DARPP-32-IR in the porcine striatal xenografts is considerably prolonged compared to rat allografts. If the ratio of the gestation periods of the two species (21 versus 115 days) is used as a rough approximation of the difference in developmental time-course then there should be a five- to six-fold difference in developmental rates of the two species. However, this is probably an over-estimation, since rats appear to be more immature at birth than pigs (Dickerson, J. W. T. and Dobbing, J. (1967) *Proc. Roy. Soc. B.* 166:384–395; Sacher, G.A. and Staffeldt, E. F. (1974) *Amer. Natur.* 108:593–616; Snow, M. H. L. and Tam, P. P. L. (1980) *Nature* 286:107. Alternatively, the ages at which fetal brains of these two species exhibit a corresponding ganglionic eminence morphology (15 versus 35 days) are only two- to three-fold greater in the pig than the rat. Though precise biochemical markers for identifying corresponding developmental ages in these species are lacking, on the basis of fetal brain morphology, gestation length, and features of graft development, it can be estimated that porcine graft development is prolonged by a factor of 3 to 4. This is consistent with estimates derived from comparative developmental morphology of a number of other fetal traits (Ullrey, D. E. et al. (1960) *J. Animal Sci.* 24:711–717. Thus, the pig xenografts at 5, 8 and 16 weeks post implantation should be comparable to rat allograft at <1, 1–2, and 3–4 weeks post implantation, respectively. This suggests that even the oldest grafts analyzed in this study are relatively immature.

The mosaic appearance of AChE staining in the porcine striatal xenografts in this study must be considered both in relation to the developmental timing of brain development in this donor species and with respect to differences in the fetal brain structures providing donor cells in this as compared to other studies of striatal grafts.

The maturational state of the graft is important because AChE-poor and DARPP-32-negative neural tissue is characteristic of early phases in the development of the striatum (Foster, G. A. et al. (1987) *J. Neurosci.* 7:1994–2018) and of comparatively immature grafts (Labandeira-Garcia, J. L. et al. (1990) *Neuroscience* 42:407–426). The inclusion of AChE-negative graft regions in these porcine xenografts may thus indicate their comparative immaturity. However, the presence of AChE-negative graft tissue may also result from the inclusion of cells committed to non-striatal fates. Using a rat-to-rat allotransplantation paradigm, it has been previously demonstrated that the lateral ganglionic eminence (LGE) but not the medial ganglionic eminence (MGE) of the developing rat telencephalon harbors the neural progenitors that subsequently form the striatal-like AChE-rich zones in fetal striatal grafts (Pakzaban, P. et al. (1993) *Exp. Brain Res.* 97:13–22). Since the porcine cells used in his study were derived only from the LGE of pig fetuses, the relative abundance of AChE-poor zones in the resulting grafts could be interpreted as evidence for non-homology of this fetal brain structure in the two species. However, the AChE-poor regions in these porcine xenografts are also comparatively neuron-poor and glia-rich. Thus, the mosaic distribution of AChE staining in these LGE grafts reflects segregation of neural versus glial populations, not segregation of striatal versus non-striatal cell populations, as was previously observed in allografts derived from combining cells from both lateral and medial ganglionic eminences (DiFiglia, M. et al. (1988) *J. Neurosci.* 8:1112–1130; Graybiel, A. M. et al. (1989) *J. Neurosci.* 9:3250–3271; Isacson, O. et al. (1987) *Neuroscience* 22 481–497; Labandeira-Garcia, J. L. et al. (1990) *Neuroscience* 42:407–426; Wictorin, K. et al. (1989) *Neuroscience* 30:313–330. Because the AChE-poor regions of these grafts are glia-rich and neuron-poor, they are neither analogous to the AChE-poor zones of LGE+MGE grafts (Isacson, O. et al. (1987) *Neuroscience* 22 481–497; Pakzaban, P. et al. (1993) *Exp. Brain Res.* 97:13–22; Sirinathsinghji, D. J. (1993) *Neuroreport* 4:659–662) nor are they likely precursors to AChE-poor zones of the adult striatum (Graybiel, A. M. (1990) *Trends Neurosci.* 13:244–254; Graybiel, A. M. et al. (1989) *J. Neurosci.* 9:3250–3271).

The localization of DARPP-32-IR somata to AChE-rich neural-rich graft regions (Wictorin et al., (1989) *Neuroscience* 30:313–330), but not to glia-rich AChE-negative regions, provides further evidence that LGE-derived neural precursors are committed to a striatal fate in both rat and pig fetuses (Pakzaban, P. et al. (1993) *Exp. Brain Res.* 97:13–22). Although the presence of non-striatal neural cells or immature striatal neural precursors cannot be ruled out in the AChE-poor regions of these grafts, the dense immunoreactivity for CD44 and GFAP exhibited in these regions suggests that they are predominantly populated with glia. Human-to-rat fetal LGE xenografts also exhibit a similar segregation of donor-derived neural and non-neural populations at early developmental stages (unpublished observations). These considerations suggest that the mosaic staining patterns in the grafts reflect the presence of an immature striatal component that is predominantly composed of glia and possibly also striatal neural progenitor cells. Comparison with porcine graft ages older than 6 months is necessary to determine whether this AChE-poor glia-rich component of LGE xenografts is completely eliminated in subsequent graft development.

Relationships Between Graft Axons and CD44-IR Graft Glia

Axons from graft neurons preferentially extend into graft regions that are predominantly populated with CD44-IR glia but are absent from graft regions that are predominantly neural. Co-localization of CD44-IR graft glia and graft axons is also observed outside the graft in host white matter. Taken together, these findings suggest that CD44-IR graft glia provide substrates or other influences that promote striatal axonal growth from the graft. Such a growth-supportive role for fetal glial cells has been demonstrated both in vitro (Ard, M. D. et al. (1988) *Soc. Neurosci. Abstr.* 14:748; Fallon, J. R. (1985) *J. Cell Biol.* 100:198–207; Fawcett, J. W. et al. (1989) *Dev. Biol.* 135:449–458; Lemmon, V. et al. (1992) *J. Neurosci.* 16:64–72; Noble, M. et al (1984) *J. Neurosci.* 4:1892–1903) and in vivo (Bray, G. M. et al. (1987) *J. Exp. Biol.* 132:5–19; Montgomery, C. T. and Robinson, J. A. (1993) *Exp. Neurol.* 122:107–124; Nieto-Sampedro, M. et al. (1984) *Proc. Natl. Acad. Sci. USA* 81:6250–6254; Kromer, L. F. et al. (1981) *Proc. Natl. Acad. Sci. USA* 82:6330–6334; Silver, J. and Ogawa, M. Y. (1983) *Science* 220:1067–1069).

The vast majority of graft axons appear to remain within the graft, producing a clear graft versus host boundary. A high density of axons within the graft, as compared to outside the graft, is also reported for human striatal xenografts (Wictorin et al. (1990) *Nature* 347:556–558). This may, in part, be a consequence of axon growth-inhibiting effects of activated microglia that accumulate in response to the excitotic lesion of the surrounding striatum (Bovolenta, P. et al. (1993) *Neuroreport* 5:345–348; Coffey, P. J. et al. (1990) *Neurosci.* 35:121–132), but it may also reflect the differential presence or absence of substrates that permit or inhibit axonal growth (Fallon, J. R. (1985) *J. Cell. Biol.* 100:198–207; Pini, A. (1993) *Science* 261:95–98).

The neuron-rich, AChE-rich, DARPP-32-IR neural regions within the graft also tend to be free of NF70-IR graft axons. These nearly axon-free regions of the graft express traits that are homologous to those of the mature striatum and are the preferred graft targets for afferents from a variety of striatal afferent systems (Labandeira-Garcia, J. L. et al. (1991) *Neurosci.* 42:407–426; Pritzel, M. et al. (1986) *Exp. Brain Res.* 65:112–126; Rutherford, A. et al. (1987) *Neurosci. Lett.* 83:275–281; Wictorin, K. et al. (1988) *Prog. Brain Res.* 78:55–60; Wictorin, K. et al. (1989) *Neuroscience* 30:313–330. Minimal penetration of graft axons into these graft regions in this study is therefore likely due to specific substrate differences. Assuming that these regions are homologous to mature striatum, whatever factors or affinities keep graft axons from growing through these graft regions may also contribute to the reduced growth of axons through the host striatum. Since the targets for the axons of the principal striatal efferents reside outside the striatum, it is not surprising that axons from these striatal-like graft neurons should show minimal affinity for striatal-like tissues. If CD44-IR glia provide a substrate that supports striatal axonal growth, axons would tend not to grow into regions lacking these glia, including both the neural clusters of the graft and the striatum of the host. It cannot be determined from these data, however, whether graft axons merely exhibit a greater affinity for graft-derived CD44-IR glia, or if they also respond to additional repulsive influences (Pini, A. (1993) *Science* 261:95–98).

These apparent constraints on axonal growth into the host brain may offer some clues to the source of the differences in axonal extension from human and porcine xenografts as compared to rat allografts. The developmentally extended period for glial and axonal growth in human and porcine grafts, as compared to rat (Labandeira-Garcia, J. L. et al. (1989) *J. L. Neuroscience* 42:407–426) or mouse grafts (Wictorin, K. et al. (1990) *Prog. Brain Res.* 82:391–399), may increase the probability that graft cell processes will be able to locate or create pathways through relatively non-permissive adult host tissues.

Axonal Outgrowth Into the Host Brain

Short-distance axon growth to the globus pallidus provides evidence for target-specific growth. Near the graft site, axons can be seen penetrating adjacent pallidal regions that are typical local striatal efferent targets. More fibers are seen penetrating the globus pallidus from grafts placed comparatively ventral and medial, near its border. Even in 8 week old grafts, axons are observed to extend as much as 200 $\mu$m from the graft to the neighboring globus pallidus, and individual axonal branches are found up to 500 $\mu$m from the graft, penetrating ventral pallidal regions. Proximity of the graft to the target appears to be an important factor affecting the probability that axons will reach their target by this early stage of development.

There is, however, reason to believe that the full extent of axonal growth is underestimated by NF70 labeling, since NF70 immunoreactivity is clearly not expressed over the full length of graft axons. Comparison of axonal staining with 70 kD bovine neurofilament antibody to axonal staining using tyrosine hydroxylase (TH) antibody in the same brain shows that 70 kD neurofilament antibody fails to stain terminal arbors that can be visualized with TH immunohistochemistry (Wictorin, K. and Bjorklund, A. (1992) *Neuroreport* 3:1045–1048). Lacking an independent axonal marker that shows terminal arbors from striatal grafts, it has not been verified whether axonal arborization extends further than that portion of the axon made visible by NF70 immunohistochemistry.

Eight week old grafts show long distance axonal growth, but unlike the long distance axonal growth reported for human striatal xenografts (Wictorin, K. et al. (1990) *Nature* 347:556–558), no NF70-IR graft axons are observed as far caudally as the substantia nigra. However, the longest post-implantation survival in this study was 16 weeks, compared to 25 weeks for human striatal xenografts (Wictorin, K. et al. (1990) *Nature* 347:556–558; Wictorin, K. et al. (1992) *J. Comp. Neurol.* 323:475–494; Wictorin, K. and Bjorklund, A. (1992) *Neuroreport* 3:1045–1048), so differences in the duration of axonal growth may, in part, account for the greater extension of human xenograft axons. Comparable post-implantation development times for porcine xenografts will be required for an unambiguous comparison of axonal growth capabilities of grafts from these two donor species.

The predominant pattern of long distance axon growth from both human and porcine xenografts involves entrainment by fiber bundles of the corpus callosum, internal capsule, and anterior commissure. Within these tracts, both graft axons and CD44-IR glial fibers show a tendency to extend in parallel alignment with the host fibers. In some cases, within the corpus callosum, axonal distance from the graft approaches 1 cm. A tendency for graft efferent fibers to follow host myelinated fiber tracts is also reported for human striatal xenografts (Wictorin, K. et al. (1990) *Nature* 347:556–558), mouse striatal xenografts and for axons from human ventral mesencephalon xenografts placed in the dopamine-cell-depleted midbrain of rats (Wictorin, K. et al. (1992) *J. Comp. Neurol.* 323:475–494)

In addition to the apparently nonspecific graft axon projections into the corpus callosum and anterior commissure, a few NEF70-IR fibers are also seen entering the lower layers of the cerebral cortex. Wictorin, K. et al. ((1990) *Nature* 347:556–558), also show axonal outgrowth from human striatal xenografts for long distances through these same white matter structures and into cerebral cortex. Atypical growth trajectories could indicate the presence of some non-striatal cell types in the grafts; however, the precisely limited dissection of the fetal ganglionic eminence in this study should have minimized such contamination. Such a growth pattern might also suggest that xenograft axon growth is less specific than normal rat axon growth. However, similar growth tendencies in allografts may have gone unnoticed due to a lack of markers specific for donor axons. Nevertheless, extensive nonspecific projections were not reported for mouse-to-rat striatal grafts (Wictorin, K. et al. (1990) *Prog. Brain Res.* 82:391–399. Some degree of nonspecificity of axonal growth is, however, a normal feature of the initial outgrowth of efferents from number of forebrain systems and is followed by a period during which a large fraction of these nonspecific axon collaterals are pruned to produce the adult patterning of connections (See O'Leary, D. D. M. and Koester, S. E. (1993) *Neuron* 10:991–1006). The comparatively more exuberant axonal growth from porcine and human grafts may reflect an exaggeration of these nonspecific growth patterns due to the prolonged development of these donor species' cells as compared to their rat hosts. In addition, the many differences between the growth environments of a normal fetal brain and that of a fetal graft developing within an adult brain further complicate these interpretations. The adult brain may offer growth cues that are not present during normal fetal development, such as myelinated fiber tracts, that may bias graft axon growth trajectories.

The preferential extension of graft axons into host fiber tracts raises other questions about mechanisms of axonal guidance. Despite the demonstration of myelin-associated axon growth-inhibiting substances (Caroni, P. and Schwab, M. E. (1988) *Neuron* 1:85–96; Schwab, M. E. (1990) *Trends Neurosci.* 13:452–455), a number of other regeneration and graft studies have shown a preference for axonal growth along myelinated fiber tracts (Wictorin, K. et al. (1990) *Nature* 347:556–558; Wictorin, K. et al. (1992) *J. Comp. Neurol.* 323:475–494; Wictorin, K. and Bjorklund, A. (1992) *Neuroreport* 3:1045–1048). Parallels can also be found in the ability for ectopically implanted peripheral nerve fiber tracts to enhance or channel CNS axonal growth (Aguayo, A. J. et al. (1984) *Neurosci. Lett.* 45:53–58; Benfey, M. and Aguayo, A. J. (1982) *Nature* 296:150–152; David, S. and Aguayo, A. J. (1981) *Science* 214:931–933; Gage, F. H. et al. (1985) *Exp. Brain Res.* 60:584–589), and for the implantation of CNS tissue (Dunnett, S. B. et al. (1989) *Exp. Brain Res.* 75:523–535; Kromer, L. F. et al. (1981) *Brain Res.* 210:173–200) or cultured Schwann cells to provide bridges through which regenerating axons can grow to distant targets (Kromer, L. F. and Cornbrooks, C. J. (1985) *Proc. Natl. Acad. Sci. USA* 82:6330–6334; Montgomery, C. T. and Robinson, J. A. (1993) *Exp. Neurol.* 122:107–124). The presence of graft glial cells and fibers along with graft axons in host white matter, suggests that the growth of axons into fiber tracts may depend on a supportive growth relationship between these cell types. The presence of such glial support may help axons overcome inhibitory signals within myelinated tissues. Embryonic glial cells can be directly involved in initial axonal guidance (Bastiani, M. J. and Goodman, C. S. (1986) *J. Neurosci.* 6:3542–3551; Jacobs, J. R. and Goodman, C. S. (1989) *J. Neurosci.* 9:2402–2411; Silver, J. et al. (1982) *J. Comp. Neurol.* 210:10–29). Radial glia in the telencephalon (Rakic, P. (1981) *Trends Neurosci.* 4:184–187), Bergman glia in the cerebellum (Rakic, P. (1971) *J. Comp. Neurol.* 141:283–312), and structural glia in the midline of the telencephalon (Silver, J. et al. (1982) *J. Comp. Neurol.* 210:10–29; Smith, G. M. et al. (1986) *J. Comp. Neurol.* 251:23–45) provide essential substrates for normal neural migration and axon growth. Radial glia in the developing basal telencephalon originate from the ventricular zone of the ganglionic eminence and pass latero-caudo-ventrally through the body of the developing striatum (Mission, J. P. et al. (1988) *Dev. Brain Res.* 44:95–108; Halliday, A. L. and Cepko, L. C. (1992) *Neuron* 9:15–26) providing a substrate for both neural migration and neurite extension. The early glial cells and their fibrous extensions observed in the present fetal grafts may be homologues to the developmentally transient radial glial cells of the normal fetal striatal anlage.

Although neural somata are rarely found outside the graft in host tissue (Liu, F. C. et al. (1993) *Neuroscience* 55:363–372), glial migration from fetal neural grafts has been observed in a number of studies (Emmett, C. J. et al. (1991) *J. Comp. Neurol.* 311:330–341; Goldberg, W. J. and Bernstein, J. J. (1988) *J. Neurosci. Res.* 20:38–45; Jacque, C. M. et al. (1986) *Dev. Neurosci.* 8:142–149; Jacque, C. M. et al. (1992) *J. Neurosci.* 12:3098–3106; Suard, I. M. et al.

(1989) *J. Neurosci. Res.* 23:172–179; Zhou, H. F. et al. (1990) *J. Comp. Neurol.* 292:320–330; Zhou, H. F. et al. (1992) *Exp. Neurol.* 122:155–164; Zhou, H. F. and Lund, R. D. (1992) *Brain Res. Dev. Brain Res.* 65:127–131). In vitro studies have demonstrated that astrocytes can be supportive of extensive axonal growth (Ard, M. D. et al. (1988) *Soc. Neurosci. Abstr.* 14:748; Fawcett, J. W. et al. (1989) *Dev. Biol.* 135:449–458; Noble, M. et al. (1984) *J. Neurosci.* 4:1892–1903). It has therefore been suggested that migrating graft glia could play a role in graft axon guidance (Lindsay, R. M. and Raisman, G. (1984) *Neuroscience* 12:513–530; McKeon, R. J. et al. (1989) *Exp. Neurol.* 103:213–221; Smith, G. M. et al. (1986) *J. Comp. Neurol.* 251:23–45). For example, Lindsay and Raisman (1984) suggested that ". . . routes of glial cell migration may determine the pathways along which transplant nerve fibers can penetrate the host." The close spatial associations observed between graft axons and graft glia outside the graft within the host brain lend support to this hypothesis.

To the extent that graft development recapitulates processes involved in axonal extension and elimination during normal development, the glial-axonal relationships observed in these grafts provides clues about axon growth processes in normal development as well as graft development. Structural glia and fetal astrocytes tend to be transient cell types during development (Levitt, P. and Rakic, P. (1980) *J. Comp. Neurol.* 193:815–840; Schmechel, D. E. and Rakic, P. (1979) *Anat. Embryol.* 156:115–152; Silver, J. et al. (1982) *J. Comp. Neurol.* 210:10–29; Smith, G. M. et al. (1986) *J. Comp. Neurol.* 251:23–45). The possibility that the donor-derived CD44-IR cells identified in these grafts are homologous to transient glial cells of the fetal striatum appears to be supported two observations: First, that fetal radial glia are also CD44-IR (Vogel, H. et al. (1992) *J. Neurocytol.* 21:363–373); and second, that there is reduced expression of CD44-IR in adult brains and a decreasing ratio of glial to neural regions during graft development. Like glial guide fibers in developing brains, CD44-IR graft glial fibers may provide an important supportive substrate for the early stages of graft axon extension. This might be particularly important during the initial axonal outgrowth phase, before axons have gained access to target-derived trophic support from established functional synapses (Purves, D. Body and Brain: A Trophic Theory of Neural Connections. (Harvard University Press, Cambridge, Mass. (1988)). The subsequent elimination of such supportive glial fibers, in both normal development and graft development, may be a factor contributing to the pruning of axon collaterals that have failed to recruit appropriate target synapses by that time (O'Leary, D. D. M. and Koester, S. E. (1993) *Neuron* 10:991–1006).

EXAMPLE II

Transplantation of Modified Porcine Striatal Cells into Lesioned Rat Brains and Histological Examination of the Transplanted Cells Experimental Design and Treatment Groups Eighty-two adult male Sprague-Dawley rats (Charles River Laboratories, USA), weighing 300–350 grams, received unilateral stereotaxic injections of quinolinic acid into the right neostriatum one week prior to transplantation. The lesioned rats were transplanted in the striatum with striatal cell suspensions prepared from the lateral ganglionic eminence (LGE) of the porcine fetal telencephalon. The LGE cell suspension derived from each of 5 different porcine litters (E30–E40) was transplanted into the rat hosts in a separate surgical session. The 74 surviving rats were divided into 3 balanced groups according to the method of immunosuppression. In group I (negative control; N=14), animals received no immunosuppression of any kind. In group II (N=29), the transplanted striatal cells were pretreated with $F(ab')_2$ fragments of a monoclonal antibody to porcine MHC-I. In group III (positive control; N=31), animals transplanted with untreated cells were immunosuppressed with daily subcutaneous injections cyclosporine A (CsA; 10 mg/kg; Sandoz Pharmaceuticals, East Hanover, N.J.). All animals were treated with a single subcutaneous dose of the antibiotic cephalothin (Keflin; 10 mg/kg; Lilly Inc., Indianapolis, Ind.) preoperatively and received tetracycline (Panamycin; 20–40 mg/kg/day; Upjohn, Kalamazoo, Mich.) in their drinking water (250 mg/l) thereafter. The CsA-treated animals were weighed weekly, and their CsA dose was adjusted accordingly. To confirm adequate serum levels of CsA, intracardiac blood from CsA-treated animals (obtained at the time of perfusion) was submitted for measurement of CsA levels by radioimmunoassay (Damon Laboratories, Westwood, Mass.). Animals were perfused 3–4 months after transplantation for histological analysis of the xenografts.

Dissection of Porcine Fetal LGE

Thirty to forty days post-insemination, five ultrasound-confirmed pregnant domestic pigs were euthanized following standard veterinary procedures at Tufts School of Veterinary Medicine (Grafton, Mass.). The range of gestational ages appropriate for selective dissection and transplantation of LGE was defined in previous studies. Deacon, T. et al. (1993) *Soc. Neurosci. Abstr.* 19:284.15. The gravid uterus was removed in a sterile fashion and rapidly transported on ice to a sterile laboratory facility where the dead fetuses were removed and transferred to sterile Dulbecco's phosphate-buffered saline (PBS). After measurement of the crown-to-rump lengths (27–35 mm), fetuses were decapitated and the fetal brains were carefully extracted from the skull through a mid-sagittal incision. Dissection of LGE was performed in Dulbecco's PBS under 40-fold magnification as previously described. Pakzaban, P. et al. (1993) *Exp. Brain Res.* 97:13–22. Briefly, a parasagittal incision was created along the dorsal aspect of each hemisphere, exposing the medial and lateral ganglionic eminences in the ventrolateral wall of the lateral ventricle. The incision was then circumferentially completed, detaching the ventrolateral wall of the hemisphere (carrying the ganglionic eminences) from the rest of the brain. The external (cortical) surface of the detached wall of the hemisphere was then flattened against the dissection dish, exposing the ganglionic eminences on the inner surface. The medial eminence was excised and discarded. The lateral eminence, now isolated on the detached wall of the lateral ventricle, was carefully resected along its base with curved microscissors and transferred to a petri dish containing calcium- and magnesium-free Hank's balanced salt solution lacking phenol red (HBSS; Sigma). The LGE tissue fragments from all fetuses in the litter were pooled.

Preparation of Cell Suspension and $F(ab')_2$ Treatment

The LGE tissue fragments were incubated with 1 ml of 0.5% trypsin-EDTA in HBSS (Sigma) at 37° C. for 10 minutes. The fragments were washed four times with fresh HBSS, then gently triturated through the tips of fire-polished Pasteur pipettes of progressively smaller internal diameter until a turbid suspension free of visible tissue fragments was obtained. Cell count and viability were determined by the acridine orange-ethidium bromide method. Brundin, P. et al. (1985) *Brain Res.* 331:251–259. For each transplantation session approximately half of the cell suspension was F(ab')$_2$-treated. F(ab')$_2$ fragments were prepared by enzymatic digestion of a monoclonal antibody to porcine MHC-I (PT85A; Veterinary Medicine Research and Development, Inc., Pullman, Wash.), using the ImmunoPure F(ab')$_2$ preparation kit (Pierce, Rockford, Ill.). LGE cells were incubated with F(ab')$_2$ fragments (1 µg F(ab')$_2$/106 cells) in HBSS at 4° C. for 30 minutes with periodic mixing, sedimented by centrifugation at 500 RPM for 5 minutes, and resuspended in a volume of HBSS calculated to yield a concentration equal to that of untreated cells (groups I and III). The final viable cell count ranged from 30,000 to 80,000 cells/µl in cell suspensions derived from different litters.

Fluorescence-activated Cell Sorting (FACS)

Presence of MHC class I antigens on the cells in the LGE cell suspension was documented by FACS analysis. A Becton-Dickinson FACScan was used. The LGE cell suspension was incubated for 1 hour on ice with a monoclonal antibody to porcine MHC-I (PT85A; not reactive against rat MHC-I, see Immunohistochemistry) at a concentration of 20 µg/ml in incubation buffer. The incubation buffer consisted of calcium- and magnesium-free PBS with 0.5% bovine serum albumin. Cells were then washed three times in the incubation buffer, and incubated for 1 hour with a goat antimouse fluorescein antibody (Cappel, Durham, N.C.) at a concentration of 1 µg/ml in incubation buffer. Fetal rat LGE cells and porcine endothelial cells served as negative and positive controls, respectively, for immunolabeling of porcine MHC-I with PT85A. In each case, specific fluorescent labeling of cells by PT85A was compared to nonspecific labeling of cells when the primary antibody was omitted.

Lesion and Transplantation Surgery

Rats were anesthetized by intraperitoneal injection of pentobarbital (65 mg/kg), and placed in a Kopf stereotaxic frame. A 5 µl Hamilton syringe attached to a 26S gauge needle (ID/OD=0.11 mm/0.46 mm) was used to deliver 120 nmoles (1 µl) of quinolinic acid into the right neostriatum of each animal (coordinates in relation to bregma: anterior=+1.0, lateral=−2.5, ventral=−4.5 mm; incisor bar at −2.5 mm) over one minute. The needle was withdrawn after one additional minute. Seven days later, the quinolate-lesioned animals were anesthetized as before in preparation for transplantation. A 10 µl Hamilton syringe attached to a 22S gauge needle (ID/OD=0.41 mm/0.71 mm) was used to carefully deliver the LGE cell suspension at a rate of 0.5 µl/min to the right neostriatum at the same coordinates as used for the lesion. Rats in groups I–III were cross-classified into 4 groups based on the total viable cell dose implanted: 80,000 cells/rat (N=11), 150,000 cells/rat (N=22), 200,000 cells/rat (N=25), and 240,000 cells/rat (N=16).

Perfusion and Tissue Processing

Three to four months after transplantation, the animals were terminally anesthetized with an overdose of pentobarbital in preparation for perfusion. The animals were perfused through the left ventricle with a heparin-saline solution (1000 units of heparin per liter of 0.9% saline), followed by 300–400 ml of 4% paraformaldehyde in 100 mM phosphate buffer (pH 7.4). The brains were immediately removed and post-fixed for 8 hours in the same 4% paraformaldehyde solution. Following post-fixation, the brains were allowed to equilibrate in 30% sucrose in PBS (pH7.4), then coronally sectioned through the forebrain at a thickness of 40 µm on a freezing microtome and collected in PBS. For examination of an alternative plane of axonal outgrowth from the grafts, selected brains were sagittally sectioned at a thickness of 40 µm.

Every sixth section was mounted onto microscope slides and stained with cresyl violet. Adjacent sections underwent acetylcholinesterase (AChE) histochemistry according to the method of Koelle. Koelle, G. B. (1954) *J. Comp. Neurol.* 100:211–235. Briefly, slide-mounted sections were incubated for 6 hours in the incubation medium containing 30 mM sodium acetate buffer, pH 5.0, 9 mM copper sulphate, 16 mM glycine, 4 mM acetyl thiocholine iodide and 0.1 mM ethopropazine. After the incubation, the slides were washed with distilled water, developed in 10% potassium ferricyanide, and washed again in distilled water prior to exposure to 0.5% sodium sulphide for 30–40 seconds.

Immunohistochemistry

Immunostaining was carried out by the avidin-biotin-peroxidase method (Vector Labs). Free floating sections were pretreated with 50% methanol and 3% hydrogen peroxide in PBS for 20 minutes, washed 3 times in PBS, and incubated in 10% normal horse serum (NHS) in PBS for 60 minutes prior to overnight incubation on a shaking platform with the primary antibody. Primary antibodies and incubation buffers used in this study consisted of a monoclonal antibody to porcine cluster of differentiation antigen 44 (CD44) diluted 1:2000 in PBS, a monoclonal antibody to neurofilament 70 kDa (NF70; Biodesign, Kennebunkport, Me.) diluted 1:40 in 1% bovine serum albumin, 1% NHS, and 0.1% Triton X-100 in PBS, a monoclonal antibody to rat leukocyte common antigen (OX1; Accurate, Westbury, N.Y.) diluted 1:50 in 1% NHS in PBS, a monoclonal antibody to rat complement receptor 3 (OX42; Accurate, Westbury, N.Y.) diluted 1:50 in 1% NHS and 0.1% TX-100 in PBS, and a monoclonal antibody to porcine MHC-I (PT85A; VMRD Inc., Pullman, Wash.) diluted 1:000 in PBS. After a 10-minute rinse in PBS and two 10-minute washes in 5% NHS, sections were incubated in biotinylated horse anti-mouse antibody (rat adsorbed; Vector Labs) at a dilution of 1:200 in 2% NHS in PBS at room temperature for 60–90 min. The sections were then rinsed three times in PBS and incubated in avidin-biotin complex (Vectastain ABC Kit ELITE; Vector Labs) in PBS for 60–90 min at room temperature. Following thorough rinsing with PBS and Tris-buffered saline, sections were developed in 0.04% hydrogen peroxide and 0.05% 3, 3'-diaminobenzidine (Sigma) in Tris-buffered saline. Controls with omission of the primary antibody were performed on selected sections to verify the specificity of staining.

The CD44, NF70, and PT-85A antibodies recognize pig but not rat tissue and were used as donor-specific markers in pig-to-rat xenografts. CD44 and NF70 were used as markers of donor glia and neurons, respectively, as previously described. Deacon, T. W. et al. (1993) *Soc. Neurosci. Abstr.* 19:284.15. OX1 was used to label lymphocytes and activated microglia. Finsen, B. R. et al. (1991) *J. Neuroimmunol.* 32:159–183. OX42 was used to label macrophages, granulocytes, and microglia. Finsen, B. R. et al. (1991) *J. Neuroimmunol.* 32:159–183.

Morphometric Analysis

The quantification of graft volumes was performed with the aid of computer image analysis (Image v.1.44 for Macintosh) as previously described. Pakzaban, P. et al. (1993) *Exp. Brain Res.* 97:13–22. Briefly, microscope images were projected on the computer screen, and the graft boundaries were traced in a calibrated image analysis window superimposed onto the video microscope image. After automated computation of the area enclosed by each tracing, the cross-sectional areas were integrated across the rostrocaudal extent of the graft to yield graft volume.

Expression of MHC-I on Porcine LGE Cells

Expression of MHC-I on porcine LGE cells was confirmed by FACS analysis, using a monoclonal antibody to porcine MHC-I (PT85A). Briefly, fluorescent intensity histograms corresponding to FACS analyses of pig lateral ganglionic eminence cells (LGE), rat LGE cells (negative control) and pig endothelial cells (positive control) were obtained. Black and gray histograms corresponded to FACS analyses performed in presence or absence of the primary antibody. Comparison of the fluorescent signal in presence of PT85A to background fluorescence (in absence of PT85A) revealed a rightward shift of the fluorescent intensity histogram. When the threshold of specific labeling was defined at 95% of the background fluorescent intensity, 20.1% of the cells were found to be specifically labeled by PT85A. No significant shift of the fluorescent intensity histogram was observed when rat LGE cells (negative control) were labeled with PT85A. In contrast, 99.6% of porcine endothelial cells (positive control) were specifically labeled with PT85A.

Effect of MHC-I Masking on Survival and Size of Striatal Xenografts

Figure 9:
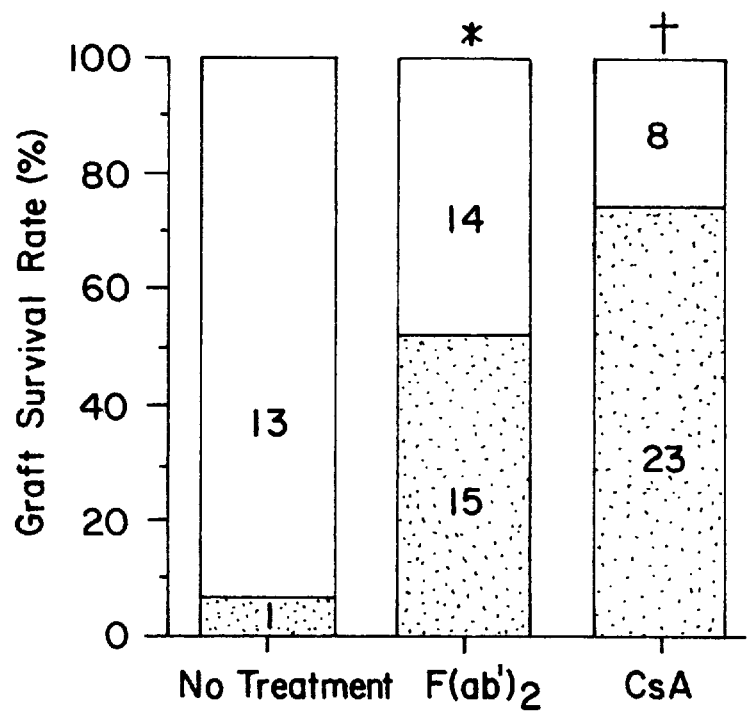
FIG. 9 is a bar graft showing survival rates of porcine striatal xenografts in absence of any treatment, after F(ab')$_2$ treatment, and after cyclosporine A (CsA) treatment. Black and white stacked columns correspond to surviving and non-surviving grafts, respectively. Numbers in each column represent number of grafts in each category. *P<0.005 for F(ab')$_2$ vs. no treatment, and Tp<0.001 for CsA vs. no treatment by Pearson chi-square analysis. The difference between CsA and F(ab')$_2$ was not statistically significant.

Survival of striatal xenografts at 3–4 months post-transplantation was assessed by immunostaining for porcine NF70 and CD44, markers of donor-derived neuronal and glial elements, respectively. Fifteen of the 29 grafts in $F(ab')_2$-treated animals survived, whereas only 1 of 14 grafts survived in non-immunosuppressed animals (FIG. 9). The improvement in graft survival after MHC-I masking was found to be significant by Pearson chi-square analysis ($P<0.005$, $\chi^2=8.03$, df=1). Similarly, graft survival after CsA treatment (23/31) was significantly greater than that in absence of immunosuppression ($P<0.001$, $\chi^2=17.42$, df=1; FIG. 9). The difference in graft survival between $F(ab')_2$ and CsA treatment groups was not statistically significant ($P>0.05$, $\chi^2=3.26$, df=1). Importantly, CsA blood levels in the latter group (832–1309 µg/l; mean 1175±115 µg/l) were uniformly therapeutic 2~31.

Figure 10:
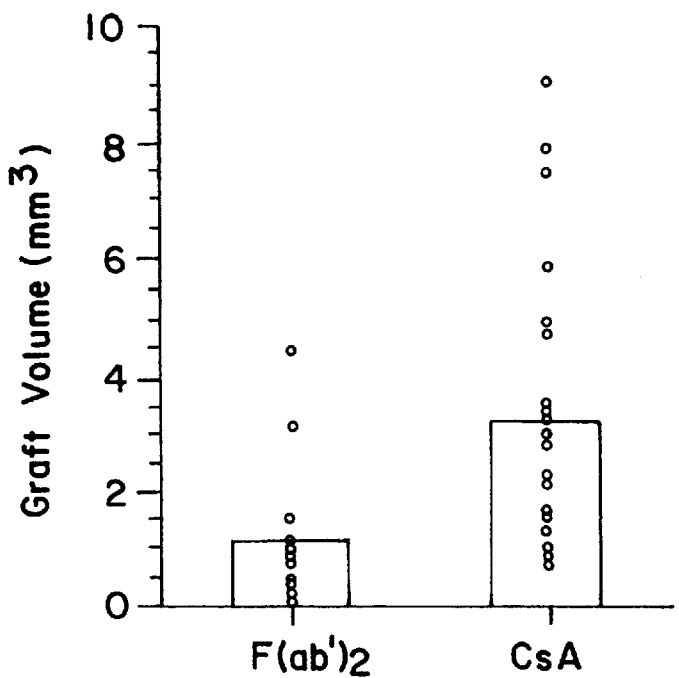
FIG. 10 is a bar graph showing porcine striatal graft volumes after F(ab')$_2$ and cyclosporine A (CsA) treatment. Open circles correspond to individual graft volumes. Columns represent mean values. P<0.05, unpaired t-test.

Quantification of graft volumes permitted a more detailed comparison of $F(ab')_2$ and CsA-treated groups (FIG. 10). Mean graft volume in $F(ab')_2$-treated animals (1.07±0.30 mm$^3$; mean±SEM) was smaller than that in CsA-treated animals (3.14±0.51 mm$^3$; $P<0.005$, t=3.06, df=36; unpaired t-test). To control for the effect of implanted cell dose in each treatment group on graft volume, a two-way analysis of variance was performed. While the difference in graft volumes between $F(ab')_2$- and CsA-treated groups remained significant ($P<0.05$, F-ratio=5.24, df=1), the effect of cell dose on graft volume did not reach statistical significance in the dose range studied ($P>0.05$, F-ratio=0.33, df=3).

Cytoarchitectonic Organization of $F(ab')_2$- and CsA-treated Striatal Xenografts To determine if the internal organization of striatal xenografts was altered by $F(ab')_2$ treatment, the cellular composition of F(ab')2-treated grafts was compared to that of CsA-treated grafts. On Nissl-stained sections, grafts in both groups were composed of multiple clusters of large neuron-like cells surrounded by bands of smaller cells. The neuronal (and striatal) phenotype of the large-cell clusters was confirmed by the close correspondence between these regions and the AChE-positive regions on adjacent sections. Some neuronal clusters exhibited a mixed density of AChE staining, consistent with recent expression of AChE in these maturing porcine grafts. Deacon, T. W. et al. (1993) *Soc. Neurosci.* Abstr. 19:284.15. Comparison of NF70 and CD44 immunostaining on adjacent sections revealed a consistent segregation of the NF70-immunoreactive (NF70-IR) neuronal and CD44-IR glial components of the grafts in both $F(ab')_2$- and CsA- treated animals. In both groups, the NF70-IR regions corresponded to the AChE-positive neuronal clusters, whereas the CD44-IR glia were distributed along the bands that surrounded and separated the neuronal clusters. While the cytoarchitectonic organization of the grafts was similar in both groups, the relative proportion of NF70-IR elements appeared to be greater in CsA-treated grafts.

Immunostaining for porcine MHC-I in selected grafts revealed persistent expression of donor MHC-I in the periphery of the surviving xenografts. Importantly, the pattern of expression of donor MHC-I corresponded to the distribution of donor-derived CD44 IR glia in both treatment groups. The NF70-IR neuronal clusters were devoid of MHC-I expression on adjacent sections. In some brains (in all three groups), necrotic graft remnants were detected on Nissl-stained sections. These regions, which were interspersed amongst intact host striatal white matter tracts, were infiltrated with small cells on Nissl stain. Immunostaining of adjacent sections with OX1 (labeling lymphocytes and activated microglia) and OX42 (labeling phagocytes and microglia) revealed an overlapping pattern of accumulation of host inflammatory cells and/or activated microglia in these regions. The inflammatory infiltrate was fairly localized and spared the striatal white matter tracts and most of the remaining neuron-rich portions of the grafts.

Axonal Outgrowth from $F(ab')_2$- and CsA-treated Striatal Xenografts

The capacity of $F(ab')_2$-treated grafts to extend axons into the host brain was compared to that of CsA-treated grafts by means of porcine NF70 immunostaining in selected sagittally-sectioned brains. Abundant NF70-IR processes originated from the caudal pole of the grafts in the striatum and extended further caudally in the direction of host globus pallidus and mesencephalon in both CsA- and $F(ab')_2$-treated animals. In both groups, target-directed outgrowth predominated over axonal outgrowth in other directions. As in CsA-treated grafts, the axons originating from $F(ab')_2$-treated neurons extended up to 3 nm along the host internal capsule.

These data show that pretreatment of xenogeneic fetal neural cells with $F(ab')_2$ antibody fragments to donor MHC-I significantly enhanced neural xenograft survival compared to non-immunosuppressed controls. $F(ab')_2$-treated xenografts, although smaller than CsA-treated grafts, exhibited the typical striatal xenograft cytoarchitectonic organization and maintained the capacity for long-distance target-directed axonal outgrowth.

EXAMPLE III

Transplantation of Porcine Striatal Cells in Lesioned Monkey Brains and Functional Analysis of the Transplanted Cells Stereotaxic Surgery Five male Rhesus monkeys (*Macaca mulatta*) bred at the New England Regional Primate Research Center (NERPRC, Southborough, Mass., USA), weighing 2.5–3.5 kg, received stereotaxic intrastriatal injections of quinolinic acid (QA) in 8 operative sessions conducted at the surgical facilities of NERPRC. The stereotaxic coordinates for each monkey were determined on the basis of a pre-operative MRI study (see below). Prior to each surgery, the animal was sedated and pre-medicated with ketamine (10 mg/kg, i.m.), xylazine (1 mg/kg, i.m.), atropine (0.05 mg/kg, i.m.) and keflin (10 mg/kg, i.m.). After induction of general endotracheal anesthesia with 1.0% isoflurane, the animal was positioned prone in a Kopf stereotaxic frame. Ear bars and orbital bars were adjusted such that a plane extending from the inferior orbital rim to the external auditory meatus (the orbito-meatal plane)

was oriented parallel to the horizon and orthogonal to the axis of the injection assembly. Symmetric placement of the cranium in the frame was confirmed by x-rays in 3 planes. Importantly, the MRI images obtained preoperatively were also oriented perpendicular to the orbito-meatal plane, thus facilitating the translation of the MRI coordinates of the striatal target to the coordinates of the stereotaxic frame.

The surgical field overlying the scalp entry site was prepared with an antiseptic solution and isolated with sterile drapes. The injection assembly, consisting of a 20 μl Hamilton syringe attached to a modified 22 gauge needle (length 3", O.D. 0.028", I.D. 0.016", bevel 45°) was filled with quinolinic acid and mounted onto the frame. QA was prepared at a concentration of 200 mM in phosphate buffer (pH7.4), stored as 50 μl aliquots at −20° C., and kept on ice during surgery. The skull was exposed through a 5 cm sagittal scalp incision and a 2×2 cm craniectomy was created at the prospective needle entry site. The underlying dura was divided to expose the pial surface. The injection assembly was lowered to the stereotaxic target position calculated on the basis of the preoperative MRI, using external auditory meatus, the sagittal sinus, and the pial surface as the MRI reference points in the 3 dimensions. QA was injected at a rate of 1 μl per 2 minutes, followed by a 2 minute wait before withdrawal of the needle. A total of 10 μl (2 μmoles) of QA was deposited along 2 injection tracts at each target site. The initial target sites consisted of the right caudate nucleus in M12 and M14, the right rostral putamen in M15, and the right caudal putamen in M16. Approximately 2 months after the first set of lesions, M12 received an additional lesion in the right rostral putamen, and M14 and M15 received additional lesions in the right caudal putamen. M17 was bilaterally lesioned in the caudal putamen in a single session. The stereotaxic coordinates for the caudate target in the 5 monkeys were distributed over the following range: anterior 18–22 mm, with respect to ear bar; lateral 4–6 mm, with respect to sagittal suture; and ventral 13–15 mm, with respect to pial surface. Similarly, the range of coordinates for the rostral and caudal putamen targets were A: 17–22, L: 10–12, V: 16–17, and A: 11–16, L: 12–14, V: 17–19, respectively. Upon completion of the injection series, the scalp was sutured closed, and the animal was awakened and returned to its cage.

Magnetic Resonance Imaging

Each monkey underwent $T_1$ and $T_2$-weighted MR imaging prior to the first surgery, and 1–2 months after each lesion surgery. MRI studies were performed on sedated animals (ketamine/xylazine, 15/1.5 mg/kg, i. m.), using a GE Signa 1.5 Tesla imaging system. The animals were positioned prone, with their heads securely positioned in a wrist coil. The orbito-meatal plane (see above) was first outlined on sagittal scout $T_1$-weighted images. Pseudo-coronal $T_1$- weighted images were then acquired at a slice thickness of 3.0 mm, repetition time (TR) of 300 msec, and echo time (TE) of 20 msec, with the slice orientation perpendicular to the Frankfurt plane. T2-weighted double spin echo images were acquired in the same orientation with TR=3000 msec, and TE=40 and 80 msec for the first and second echoes, respectively.

Positron Emission Tomography

The ligand $^{11}$C-SCH was synthesized by direct $^{11}$C-methyl iodide methylation of benzonaphtazepine (Schering compound 39166). Briefly, $^{11}$C-methyl iodide was reacted with a 100 μg aliquot of the N-demethylated precursor (nor-SCH) in 0.1 ml CH3CN:DMF (9:1) and the activity dissolved in Ringer's lactate buffer after solvent evaporation (>600 Ci/mmol). Purification and analysis were performed using high performance liquid chromatography (HPLC). PET measurements were performed using a high resolution PET scanning system (PCR-I) equipped with one ring of 360 BGO detectors (FWHM resolution: 4.5 mm; sensitivity: 46,000 Hz/μCi/ml). Emission data were acquired from the time of tracer injection until the end of the experiment (90 min). The sedated monkey (ketamine/xylazine, 15/1.5 mg/kg, i.m.) was positioned prone with the head secured in a head holder. Seven tomographic planes (five levels through the caudate and putamen and two levels through the cerebellum) were sequentially studied by moving the subject bed at predetermined positions located 10, 15, 20, 25 and 30 mm anterior and 5 and 10 mm posterior to the frontal plane containing the earbars. Data were quantified according to Farde et al. (1986) Science 231:258–261 and Sedvall, G. et al. (1991) Ann. Neurol. 32:358–364.

Behavioral Analysis

At the onset of the study, all animals were allowed to habituate to a 1.5 m×1.5 m×1.5 m plexiglass filming cage for a total of 6 hours in divided sessions. Animals were then video recorded in this cage at 3 week intervals both before and after the QA lesion surgeries. In each session, the animal was first allowed to habituate to the filming cage for 20 minutes, then filmed for 10 minutes unstimulated (no drug condition), and finally given apomorphine (0.5 mg/kg i.m.) and filmed for another 30 minutes. This allowed assessment of both spontaneous motor behavior and behavior following dopaminergic stimulation designed to evoke dyskinesias. No observer was present during the actual video-recording so as to minimize external influences on the behavior of the animal. The video tapes were later viewed by two independent observers who were instructed to record the number and duration of all episodes of abnormal involuntary movement (dyskinesia), including dystonic postures, extremity jerks, ballistic movements, choreoform and athetoid movements, head and neck torsion, twisting of trunk, and rolling of pelvis. The recording was facilitated with the aid of a Macintosh Hypercard-based program (Hypermonkey 2.0) written by PP. The total time period (in seconds) that the monkey spent in apomorphine-induced dyskinetic states in the 30-minute filming session was defined as the monkey's dyskinesia score for that session. The duration of dyskinesia was then correlated with the location of the excitotoxic lesion in the animal's striatum based on PET and MRI studies.

Anatomical Localization of QA Lesions

The location and extent of the QA lesions in the striatum of each monkey were assessed by MR imaging and quantitative PET analysis, using the diminution in D1 receptor binding as an index of striatal dopaminoceptive neuronal loss. Brownell, A. -L. et al. (1994) Exp. Neurol. 125:41–51. The MR signal in the region of the excitotoxic lesion evolved from hypo- to hyper-intense on $T_1$-weighted images in the first post-lesion month but was hyper-intense on all $T_2$-weighted images, consistent with previous reports. Hantraye, P. et al. (1992) Proc. Natl. Acad. Sci. USA 89:4187–4191. In all cases, there was excellent correspondence between the intended position of the lesion, the location of the MR signal on $T_1$ and $T_2$-weighted images, and regional depletion of D1 receptor binding by PET. All lesions were found to be focal in extent, limited to one of three zones: the head of the caudate (e.g. M12), the anterior half of the putamen (e.g. M15), or the posterior half of the putamen (e.g. M16). Quantification of PET data in the 3 representative cases revealed similar depletions in D1 receptor binding in their respective zones, compared to the intact contralateral side. The lesion in the head of the caudate showed a D1 receptor binding depletion of 18% in the 5-mm slice shown. Following a lesion to the anterior putamen, a 26% loss of putaminal D1 receptor binding was observed in the anterior slice. Finally, a lesion to the posterior putamen produced a putaminal depletion in D1 receptor binding of 27% in this posterior 5-mm slice. This quantification confirmed that the selective lesions were roughly equivalent in size.

Animals that did not display prominent spontaneous or apomorphine-induced dyskinesias received a second lesion in a different striatal zone about two months after the first lesion. Specifically, the two animals with lesions in the head of the caudate (M12 and M14) received a second lesion in the anterior putamen (M12') or posterior putamen (M14'), and one animal with an initial lesion in the anterior putamen (M15) received a second lesion in the posterior putamen (M15'). One dyskinetic animal with an initial lesion in posterior putamen did not receive a second lesion (M16). Based on behavioral data corresponding to these 7 sets of lesions (see below), the effect of bilateral selective QA lesions in the posterior putamenon motor behavior was investigated in one animal (M17).

Effects of Selective Unilateral Striatal Lesions on Motor Behavior

All unilaterally-leisoned animals were able to feed and groom without difficulty immediately after lesion surgery, and none exhibited signs of hemiparesis or hypalgesia. In absence of apomorphine, the animals variably exhibited mild transient dyskinetic jerking or dystonic posturing of the contralateral arm or leg in the first week after the lesion, but all such spontaneous movements subsided by the second week. Some animals (M12, M14, and M16) developed a spontaneous rotational preference to one side, but the direction of rotation was different in different animals and could change with time in a single animal. For instance, M14 exhibited 125–180 full turns to the left (contralateral to the lesion side) in daily 10 min. observation periods in the first 14 days after a right caudate lesion. In contrast, M12 exhibited 71 contralateral turns (per 10 min.) at 2 days, 10 ipsilateral turns at 4 days, 243 ipsilateral turns at 10 days (peak), and 142 ipsilateral turns at 14 days after a right caudate lesion.

Although spontaneous dyskinetic movements disappeared after the first week, a temporary dyskinetic state could always be induced by apomorphine administration. In intact animals, apomorphine-induced dyskinesias were either absent or brief. The cumulative duration of such dyskinesias in intact animals did not exceed 84 seconds in the 1800-second test interval. Of the 2 animals with caudate lesions, M12 exhibited no apomorphine-induced dyskinesia, while M14 demonstrated brief dystonic posturing of the left leg. Addition of an anterior putamen lesion to the caudate lesion did not produce dyskinesia (M12'), while addition of a posterior putamen lesion in an animal with a caudate lesion (M14') produced marked, sustained apomorphine-induced dyskinesia, characterized by prominent jerking and prolonged dystonia of all limbs, episodic twisting of the trunk, torsion of the neck, and irregular head movements. Similarly, in absence of an initial caudate lesion, an isolated anterior putamen lesion did not produce dyskinesia (M15), while a selective posterior putamen lesion produced marked irregular jerking of all extremities and dystonia of the tail (M16). Interestingly, although the presence of a lesion in the posterior putamen correlated with occurrence of apomorphine-induced dyskinesia, addition of a posterior putamen lesion to an animal with a prior anterior putamen lesion failed to produce a dyskinetic syndrome (M15').

Selective Bilateral Posterior Putamen Lesions

In contrast to the unilaterally-lesioned animals, the bilaterally-lesioned animal (M17) displayed marked spontaneous Huntington-like movements in the first 48 hours after lesioning. While the animal appeared to have normal strength in all limbs and well-preserved fine motor coordination (assessed by reaching for food pellets), it exhibited poor coordination of proximal limb movements, periodic flinging of the arms, irregular writhing of the forearm and wrist, dystonia, rolling of the pelvis, torsion of the trunk, orofacial dyskinesias, and the inability to coordinate chewing movements, necessitating a soft diet. Of all the abnormal motor behaviors observed in this study, the constellation of abnormal spontaneous movements in this bilaterally-lesioned animal most closely resembled the choreo-dystonic movements characteristic of Huntington's disease. This spontaneous motor syndrome resolved by the third day after the lesion, and the animal regained the ability to chew food pellets and groom. The apomorphine-induced motoric syndrome, however, persisted and was characterized by rapid dyskinetic movements and brief choreic episodes.

Transplantation of Striatal Cells into the Lesioned Areas of the Monkey Brains

In conjunction with pharmacologic immunosuppression (either modification of the porcine striatal cells using $F(ab')_2$ fragments or cyclosporin administration), 30-day-post-conception, fetal porcine cell-suspensions containing about one million neural cells obtained from the lateral ganglionic eminence were transplanted into the lesioned sites of monkeys M15, M16, and M18. Monkeys M15 and M18 were transplanted with $F(ab')_2$-treated striatal cells. Monkey M16 was transplanted with non-$F(ab')_2$ treated striatal cells but was treated with cyclosporin beginning one day prior to transplantation.

Figure 11:
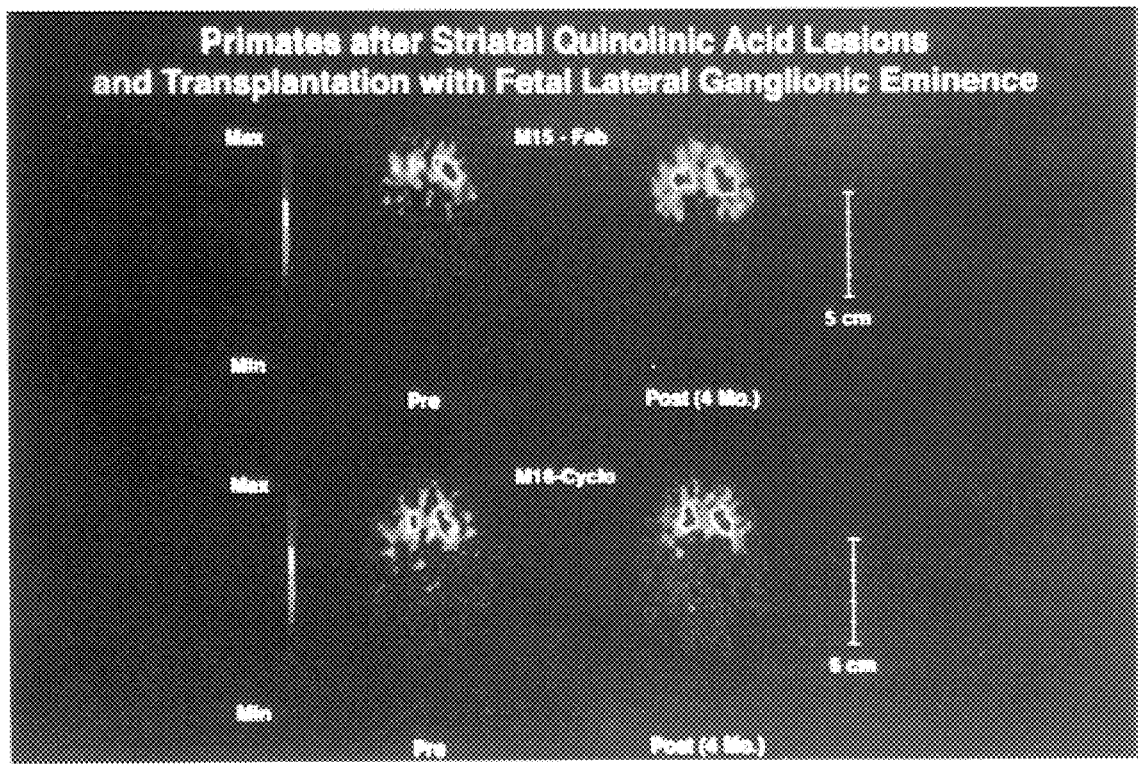
FIG. 11 represents PET scans from two different monkeys. The PET scans were generated before and after the monkeys received transplants of F(ab')$_2$ or non-F(ab')$_2$-treated embryonic day 30 porcine lateral ganglionic eminence cells.

PET images for monkeys M15 and M16 prior to transplantation and four months post transplantation were generated as described above and are shown in FIG. 11. As shown in FIG. 11, there is an increase in the PET signal on the lesioned side of both animals after transplantation.

Figure 12:
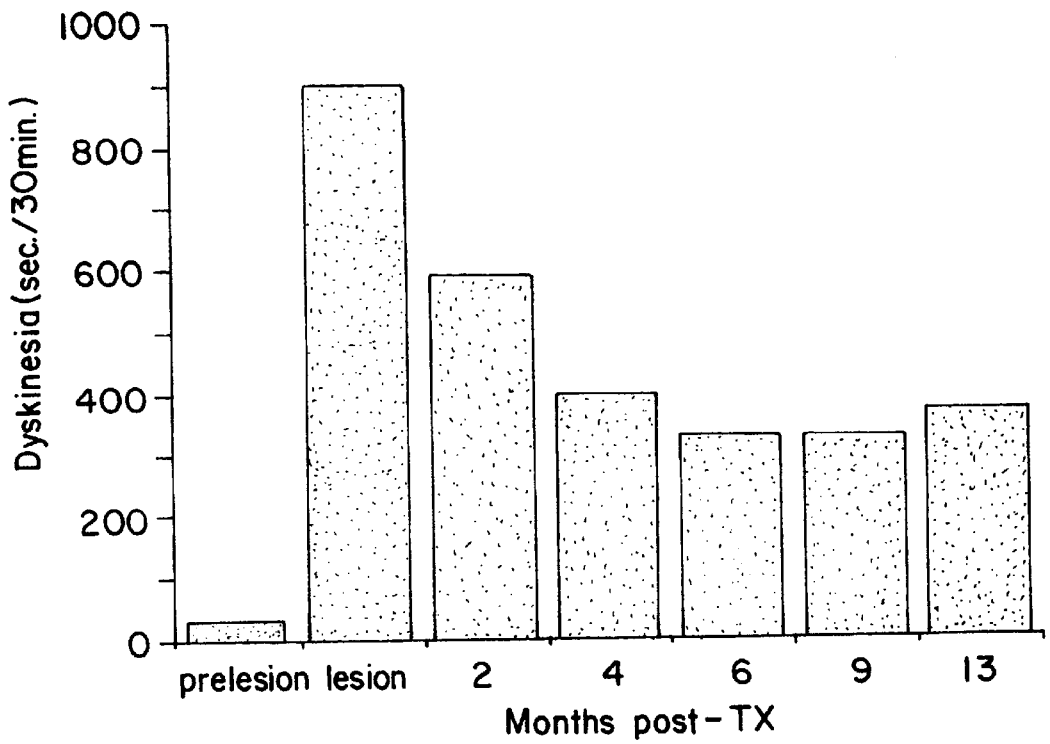
FIG. 12 is a bar graph showing apomorphine-induced dyskenisia in monkeys after transplant of non-F(ab')$_2$-treated embryonic day 30 porcine lateral ganglionic eminence cells.
Figure 13:
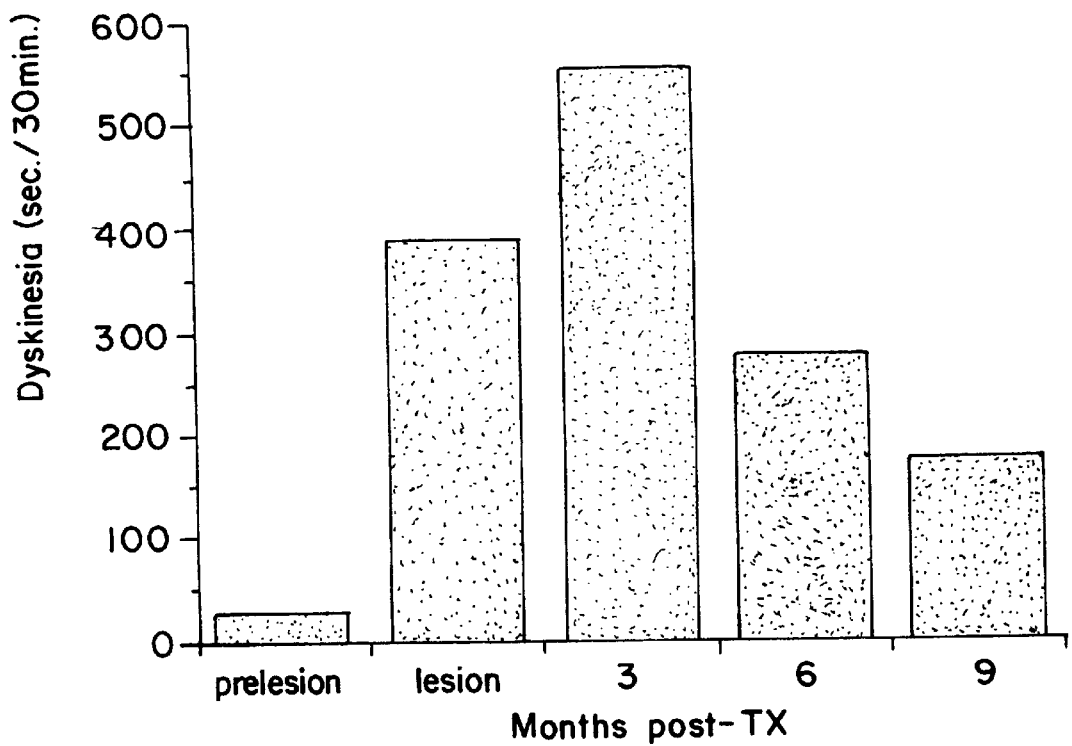
FIG. 13 is a bar graph showing apomorphine-induced dyskenisia in monkeys after transplant of F(ab')$_2$-treated embryonic day 30 porcine lateral ganglionic eminence cells.

Monkeys M16 and M18 were then tested for behavioral deficit as measured by apomorphine induced dyskinesias as described above. Measurements of dyskenisia were made both pre- and post-transplantation. The results of these tests are shown in graph form in FIGS. 12 and 13. As shown in FIG. 12, recovery in monkey M16 was observed at two months post-transplant and has continued at 4, 6, 9, and 13 months post-transplant. As shown in FIG. 13, recovery in monkey M18 was observed at 6 months post-transplant and has continued 9 months post-transplant.

EXAMPLE IV

Transplantation of Porcine Ventral Mesencephalic Cells into Lesioned Rat Brains and Histological and Functional Analysis of the Transplanted Cells Lesion Surgery, Behavioral Testing and Experimental Groups Adult female Sprague-Dawley rats received a unilateral dopamine (DA)-depleting lesion by stereotaxic injection of 6-OHDA (3.6 µg/µl 0.02% ascorbic acid in saline) at two sites (2.5 µl/site) in the medial forebrain bundle using a 10 µl Hamilton syringe (coordinates relative to bregma: AP=−4.0, L=−0.8, V=−8.0, incisor bar=+3.4; AP=−4.4, L =−1.2, V=−7.8, incisor bar=−2.4). 6-OHDA was infused at a rate of 1 µl/min, and the needle was left in place for an additional 2 minutes prior to withdrawal. All surgeries were conducted under sodium pentobarbital (65 mg/kg, ip) anesthesia in a Kopf stereotaxic frame. Three weeks post-lesion, rats were tested for amphetamine-induced (5 mg/kg, ip) rotational asymmetry using automated rotometers (San Diego Instruments). Ungerstedt, U. et al. (1970) *Brain Res.* 24:485–493.

Twenty-four rats with a net ipsilateral rotation (ipsilateral rotations minus contralateral rotations) greater than 800 rotations per 90 minutes, reflecting an approximate 97% DA depletion (Schmidt, R. H. et al. (1982) *J. Neurochem.* 38:737–748), were divided into two experimental xenotransplantation groups balanced with respect to pre-transplant rotation scores. In group A (n=12), rats received daily injections of Cyclosporine A (CyA) (Sandimmune; 10 mg/kg, diluted in olive oil, sc; Sandoz, East Hanover, N.J.) commencing one day prior to transplantation. In group B (n=12), rats received no CyA. CyA-treated rats received tetracycline (Panamycin; approximately 20–40 mg/kg/d; Upjohn, Kalamazoo, Mich.) via their drinking water (250 mg/l) beginning 30 days after transplantation. Rotational asymmetry was monitored at 4–6 week intervals following transplantation to assess the graft-associated functional recovery. One rat from Group A died during transplantation surgery and one rat from Group B died following amphetamine rotation.

Preparation and Transplantation of Porcine Fetal Ventral Mesencephalon

Fetuses were obtained from two ultrasound-confirmed pregnant Yorkshire pigs 27 days post-insemination according to the standard procedures of Tufts University School of Veterinary Medicine (Grafton, Mass.). Fetuses (crown-to-rump length, CRL=21 mm) were removed to a dish with cold sterile calcium- and magnesium- free Dulbecco's phosphate buffered saline (PBS), and the ventral mesencephalon (VM) was dissected from the surrounding tissue and collected in a petri dish containing Dulbecco's PBS. The VM fragments were incubated at 37° C. for 10 minutes in 1.5 ml of pre-warmed 0.05% Trypsin-0.53 mM EDTA (Sigma) in calcium- and magnesium-free Hanks Balanced Salt Solution (HBSS). The tissue was then washed four times with HBSS with 50 μg/ml Pulmozyme (human recombinant DNase, Genentech), and then gently triturated through a series of fire-polished Pasteur pipettes of decreasing diameter until a cell suspension containing single cells and small clumps of cells was obtained. Cell number and viability were determined under fluorescence microscopy using acridine orange-ethidium bromide as previously described. Brundin, P. et al. (1985) *Exp. Brain Res.* 60:204–208.

Rats were anesthetized as described in the previous section and were grafted in the denervated striatum with a suspension of approximately 200,000 VM cells. Using a 10 μl Hamilton syringe, 2 μl of the VM cell suspension was injected at each of 2 striatal sites at a rate of 1 μl/min followed by a 2 minute pause prior to withdrawal of the needle (coordinates relative to bregma: AP=+1.5, L=−2.8, V=−5.0 to −4.5; AP=+0.5, L=−3.0, V=−5.0 to −4.5, incisor bar=−3.3). All rats received preoperative doses of cephalothin (Keflin; 10 mg/kg, sc; Lilly, Inc., Indianapolis, Ind.) and methylprednisolone (Depo-Medrol; 5 mg/kg, im; Upjohn, Kalamazoo, Mich.).

Perfusion and Histological Processing

Nineteen weeks post-transplantation, animals were terminally anesthetized with sodium pentobarbital and perfused through the left ventricle with 250 ml cold heparinized saline (1000 units heparin/liter 0.9% saline) followed by 250 ml cold 4% paraformaldehyde in 100 mM PBS (pH7.4). Brains were removed and post-fixed for 8 hours in this same paraformaldehyde solution before being transferred to 30% sucrose in PBS (pH7.4). Following equilibration, a series of 40 μm coronal sections were cut using a freezing microtome and collected in PBS.

Every sixth section was stained with cresyl violet in order to evaluate graft survival. To assess neuronal survival and graft morphology, adjacent sections were immunostained by the avidin-biotin peroxidase method (Vector Labs, Burlingame, Calif.) for tyrosine hydroxylase (TH), neurofilament, or donor-derived glia. Free-floating sections were pretreated with 50% methanol and 0.3% hydrogen peroxide in PBS for 20 minutes, rinsed three times in PBS, and then pre-incubated for 1 hour in 10% normal blocking serum (NBS; normal goat serum for TH and NF70; normal horse serum for CD44) in PBS prior to overnight incubation with primary antibody. TH antibody (Pel-Freez, Rogers, Ak.) was diluted 1:250 in PBS containing 1% normal goat serum, 1% bovine serum albumin, and 0.1% Triton-X. A monoclonal antibody to neurofilament 70,000 mol. wt. (rat adsorbed, NF70; Biodesign, Kennebunkport, Me.) was diluted 1:1000 in PBS. To immunostain donor glia, a monoclonal antibody against porcine cluster of differentiation antigen 44 (CD44; Diacrin, Inc., Charlestown, Mass.) was diluted 1:2000 in PBS. Sections were then washed in PBS and incubated with goat anti-rabbit (TH; Vector Labs), goat anti-mouse (NF70; Sigma), or horse anti-mouse (CD44; Vector Labs) biotinylated secondary antibody diluted 1:200 (TH, CD44) or 1:1000 (NF70) in 2% NBS in PBS for 90 minutes. After three PBS rinses, the sections were incubated with avidin-biotin complex (Vectastain ABC Kit ELITE, Vector Labs) for 90 min, rinsed once in PBS and twice in 0.05 M tris-buffered saline (TBS), then developed with 0.04% hydrogen peroxide and 0.05% 3,3'diaminobenzidine (Sigma) in TBS for 5–15 min.

In selected sections, donor-derived cells were identified via in situ hybridization with a digoxigenin-labelled porcine repeat element (PRE) DNA probe which reacts specifically with porcine nuclei as described previously, (Oettinger, H. F. et al. (1995) *Cell Transplant.* 4:253–256), with the following modifications for brain sections. Briefly, following TH immunohistochemical staining, sections were placed onto slides, allowed to dry, covered with pepsin, and incubated for 15 minutes at 50° C. Following two 5 minute rinses in 2× sodium chloride-sodium citrate (SSC), sections were allowed to dry and were covered with a hybridization mixture containing a 234 bp PCR product digoxigenin-labelled PRE probe (25 ng/ml) diluted in Hybrisol VIII (1:700; Oncor, Inc., Gaithersburg, Md.). The PRE probe was generated by PCR using primers flanking the repeat sequence and labelled with digoxigenin (Digoxigenin DNA Label Kit, Boehringer Mannheim, Indianapolis, Ind.). Sections were covered with a glass coverslip and denatured at 100° C. for 10 minutes. Following overnight hybridization at 37° C., slides were soaked in 2× SSC to remove the coverslips, and sections were rinsed for 10 minutes in a solution of 65% formamide in 2× SSC two times at 37° C. and once at 42° C. Sections were then rinsed twice in PBS and incubated at room temperature for 2 hours with an alkaline phosphatase-conjugated anti-digoxigenin antibody (1:200 in PBS; Boehringer Mannheim, Indianapolis, Ind.). Sections were then developed with 5-bromo-4-chloro-3-indolyl-phosphate/4-nitro-blue tetrazolium chloride (BCIP/NBT) substrate (Zymed, San Francisco, Calif.) and counterstained with nuclear fast red.

Morphometric and Statistical Analyses

Rotational data were analyzed by repeated measures analysis of variance (general linear model) with SAS 6.08 (SAS Institute, Cary, N.C.) followed by CONTRAST and Bonferonni adjustment for multiple comparisons. Non-linear regression was performed with DeltaGraph Professional 3.5 (Delta Point, Monterey, Calif.) using the Marquardt-Levenberg algorithm. TH-positive neurons were counted in every sixth section of each graft and expressed as total number of TH neurons per graft using the Abercrombie formula, (Abercrombie (1946) *Ana Rec.* 94:239–247), and total graft volume was quantified by measuring CD44-positive graft areas with the aid of a computer image analysis system (Image v. 1.52 for Macintosh) and integrating the cross-sectional areas across the graft. TH-positive neuron survival and graft volume were compared between groups by unpaired t-test. A value of p<0.05 was considered statistically significant.

Effects of Porcine Ventral Mesencephalic Grafts on Rotational Asymmetry

Figure 14A:
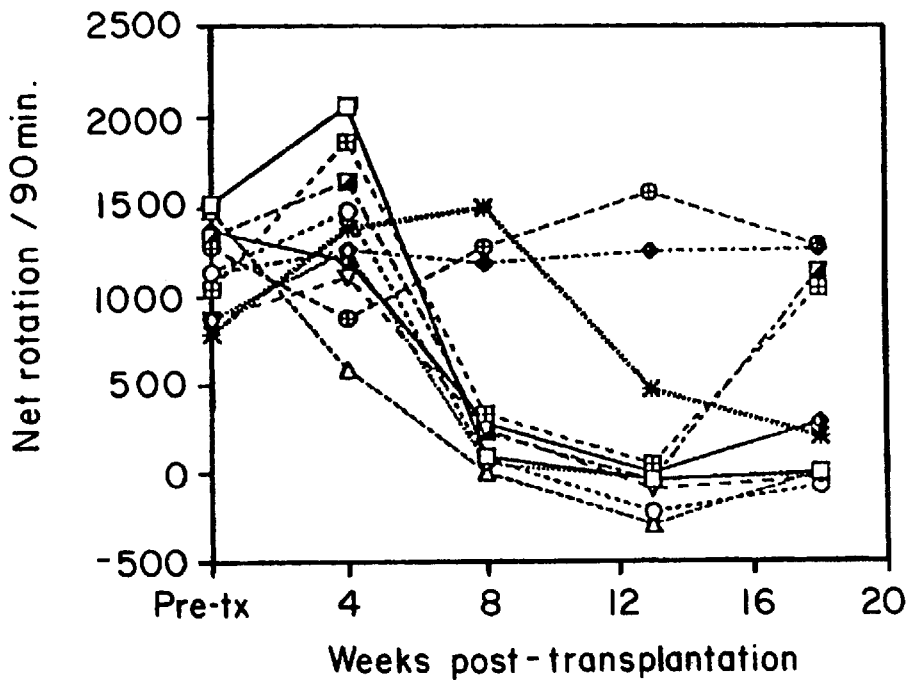
FIGS. 14A–14B are graphs depicting amphetamine-induced net rotation asymmetry scores (turns ipsilateral to lesion minus turns contralateral to lesion during 90 minute period) plotted for individual rats pre-transplantation and at 4–6 week intervals post-transplantation with porcine mesencephalic cells.
Figure 14B:
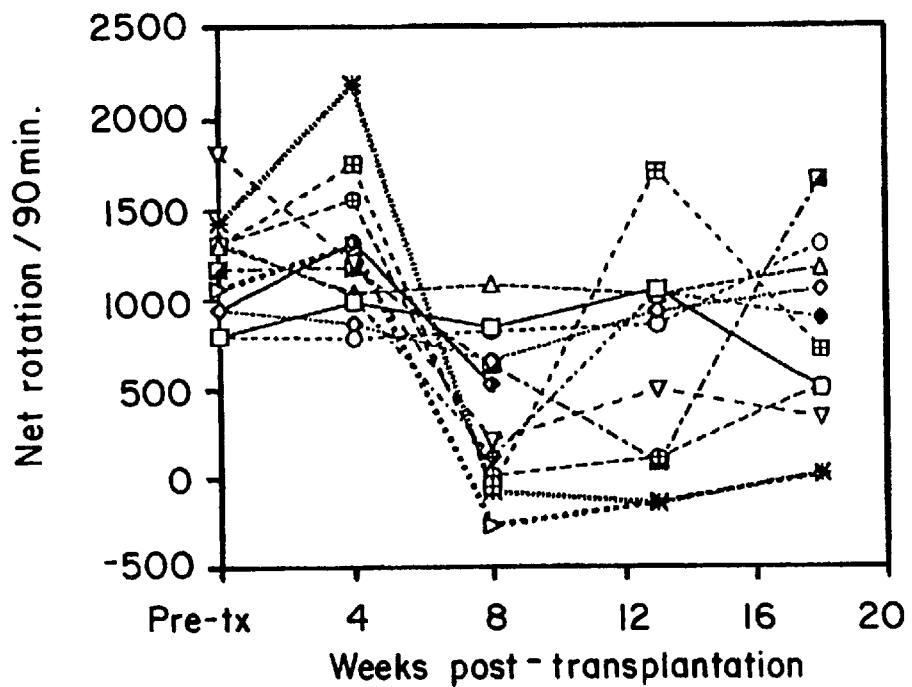

Amphetamine-induced rotational asymmetry was evaluated at 4–6 week intervals following transplantation of porcine fetal VM cells into the DA-depleted rat striatum. Individual net rotation scores for CyA and non-CyA treated rats are summarized in FIGS. 14A–14B. In the CyA treated group, 8 rats showed a greater than 50% decline in rotation at 8 weeks post-grafting relative to pre-transplant, and a ninth rat showed a reduction in rotation by 13 weeks. Two rats with behavioral evidence of functional grafts at 13 weeks returned to near pre-transplant baseline rotation levels by 18 weeks post-transplantation. Two additional CyA-treated rats did not show any evidence of behavioral recovery during the course of the study.

A similar time-course of recovery was apparent in the non-CyA rats with 6 out of 11 rats showing a greater than 50% reduction in rotational asymmetry at 8 weeks post-transplantation. An additional rat showed functional graft effects at 13 weeks post-transplantation. However, at the end-point of the study, only 4 non-CyA rats maintained this reduction. Four of the rats in this group exhibited no evidence of functional recovery.

There was no significant difference in pre-transplantation net rotation scores between groups (unpaired t-test). There was a significant effect of time on rotational behavior across groups (p=0.0001), yet there was not a significant group x time interaction. Further, group analyses demonstrated that at 8 weeks following transplantation, both the CyA and non-CyA groups showed a significant decrease in rotational symmetry as compared to their respective pretransplant values (CyA: pre=1170.0±76.9, mean±SEM, wk 8=483.9±167.8, p=0.023; No CyA: pre=1205.4±89.5, wk 8=357.0±138.6, p=0.004). For the CyA-treated group, this attenuation of rotational deficit was maintained for the course of the study as indicated by the finding that the final rotation value at 19 weeks post-transplant (465±178.17) did not significantly differ from that achieved at 8 weeks and remained significantly lower than the pre-transplant value (p=0.01). In contrast, while the non-CyA group did show a significant decline in rotation at 8 weeks after grafting, this correction was not maintained at 19 weeks post-transplantation at which time the net rotation score (734.4±160.1) was significantly greater than that observed at the 8 week recovery point (p=0.029). Furthermore, at the endpoint of the study, the CyA-treated group did not significantly differ from the pretransplant baseline score.

Survival and Size of Porcine Ventral Mesencephalic Grafts

Figure 15A:
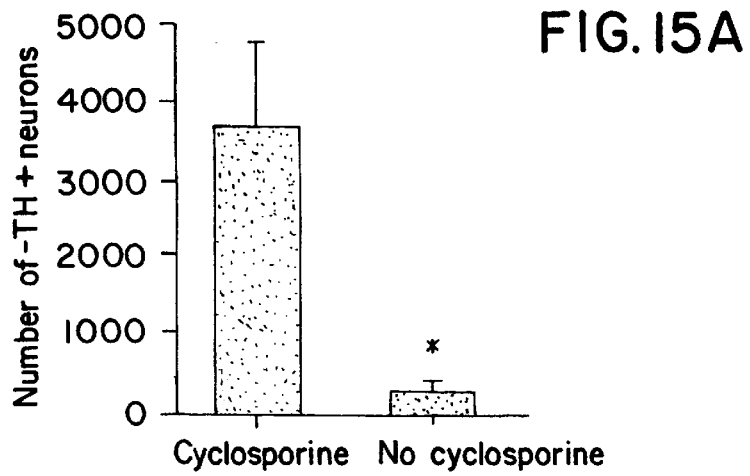
FIGS. 15A–15B are bar graphs which provide a comparison of the number of surviving TH+ neurons in CyA treated and non-CyA treated porcine mesencephalic cells at 19 weeks after transplantation into rats (FIG. 15A) and a comparison of the porcine mesencephalic graph volume in CyA treated and non-CyA treated rats (FIG. 15B). Columns represent mean values. Bars represent SEM. *p<0.05, unpaired t-test.
Figure 15B:
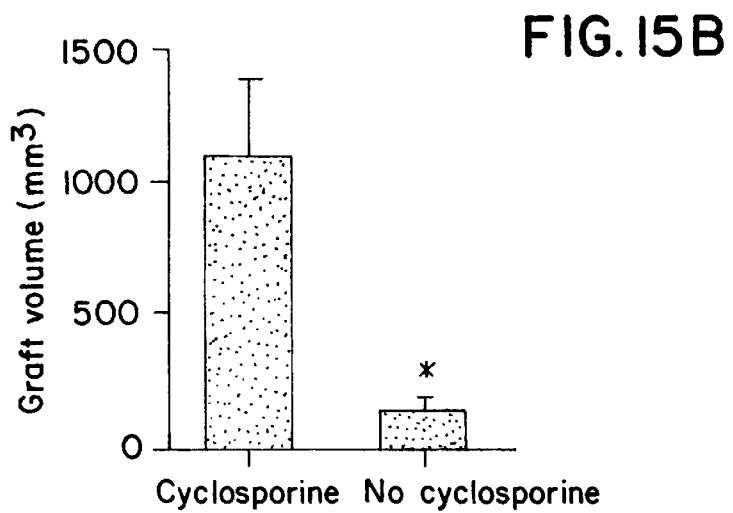

Neural xenograft survival was assessed 19 weeks post-transplantation by TH immunohistochemistry and Nissl staining. The average number of surviving TH+ cell bodies in the grafts of the CyA-treated rats (n=6; 3690±1023, mean±SEM) was signficantly greater than that in the non-CyA animals (n=6; 257±164; p=0.0078, FIG. 15A). A similar survival effect was evident upon measuring the graft volume of sections immunostained for the donor-specific glial marker CD44 (FIG. 15B). Mean graft volume in the CyA-treated group (1.10 mm$^3$±0.29) was significantly greater than that of the non-CyA-treated group (0.14 mm$^3$±0.06, p=0.0084).

Correlation Between TH+ Neuron Survival and Functional Recovery

Figure 16:
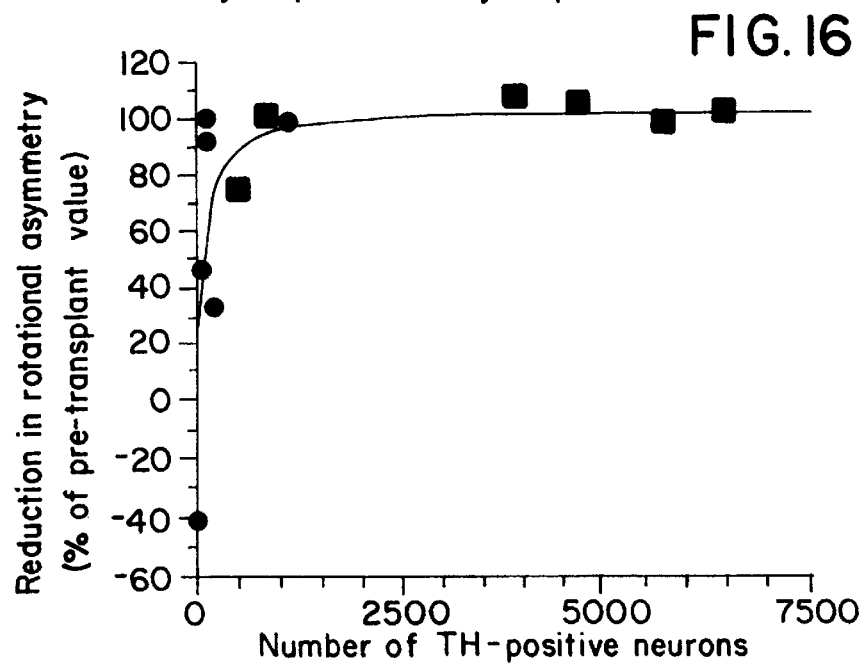
FIG. 16 is a graph depicting the relationship between TH+ neuron survival and extent of functional recovery in a group of rats transplanted with porcine mesencephalic cells and treated with CyA (squares represent individual rats from the CyA treated group) and a group of rats transplanted with porcine mesencephalic cells and not treated with CyA (circles represent rats from the non-CyA treated group). Non-linear regression analysis revealed a saturatable relationship fit to the equation RR=RR$_{max}$*N/N$_{50}$+N where RR=rotational reduction; RR$_{max}$=maximum rotational reduction; N=number of TH+ neurons; N$_{50}$=number of TH+ neurons necessary to achieve a 50% reduction in rotation (RR=104*N/[77+N]; r$^2$=0.642).

Non-linear regression analysis of TH+ neuron survival and extent of functional recovery, as measured by the change in net rotation, revealed a saturable relationship (y=104x/[77+x]; r$^2$=0.642) indicating that survival of approximately 80–100 TH+ neurons is necessary to achieve a 50% reduction in net rotational asymmetry (FIG. 16). At a survival of approximately 850–1000 TH+ neurons, behavioral recovery plateaued with additional neuronal survival providing no further effect on rotation. In each group, there was one rat which showed evidence of behavioral recovery yet, which upon histological analysis, revealed no surviving grafts using available histologic techniques. These animals were not included in this correlation analysis.

Morphology and Organization of Fetal Porcine Ventral Mesencephalic Grafts

The neuronal and glial organization of ventral mesencephalic xenografts in the CyA treated and non-CyA treated groups was assessed by Nissl staining and TH, NF70, and CD44 immunostaining. Nissl stained sections of CyA-treated rats showed large, neuron rich grafts which were well-integrated with the host tissue (FIG. 17A). The transplants contained large numbers of TH+ cell bodies with the characteristic morphology of SN DA neurons (FIG. 17B). The porcine VM xenografts exhibited organotypic features of the SN, with large clusters of TH+ neurons at the graft perimeter and a dense network of TH+ and non-dopaminergic, NF70+ neuronal fibers within the transplant and extending from the graft to innervate the surrounding host striatum (FIGS. 17B–17C). CD44 immunostaining of donor-derived glia revealed a distinct glial compartmentalization within the graft and glial fibers extending from the transplant into the host striatum (FIG. 17D). Nissl staining of the two CyA treated rats which showed loss of behavioral recovery revealed a small-cell infiltrate and a limited area of necrosis at the graft site suggestive of ongoing immune rejection. In addition, there was no evidence of neuronal graft survival in the two CyA treated rats which showed no behavioral compensation. A slight scar (approximately 50–100 μm in length) was present along the needle tract in these two animals.

In contrast to the CyA-treated rats, grafts from non-CyA rats were characteristically small and condensed with few surviving neurons (FIGS. 17E–17G). All surviving grafts from this group contained varying degrees of small-cell infiltration suggesting ongoing rejection processes. Interestingly, the glial compartmentalization evident in the CyA treated rats was lacking in grafts apparently undergoing rejection, and fiber outgrowth was limited (FIG. 17H). However, in the non-CyA rats, greater survival of the glial components of the graft were apparent relative to the neuronal components. No significant host tissue damage was apparent beyond the transplant site in rats that had apparently rejected their grafts.

In situ hybridization of PRE DNA detected donor cells not only within the confines of the grafted striatum, but also cells within host white matter tracts which had migrated to the contralateral hemisphere. The graft-derived fibers reinnervated the entire the extent of the striatum. TH+ neuron staining was absent in SN ipsilateral to the 6-OHDA lesion, indicating that the dense striatal innervation was donor-derived.

The present results demonstrate that ED 27 porcine neuroblasts transplanted into the DA-depleted rat striatum are able to reinnervate the host and mediate functional recovery as measured by amphetamine-induced rotational asymmetry. The extent of behavioral recovery was found to be highly correlated with the number of surviving TH+ neurons.

Behavioral evidence of functional grafts was present in the non-CyA treated group and suggests a relatively prolonged period of xenograft survival in this group. This may be due to the a single dose of the immunosuppressive steroid methylprednisolone which was administered preoperatively in the present study. While steroids are used in some clinical neurotransplantation protocols (Widner, H. et al. (1992) *N. Engl. J. Med.* 327:1556–1563; Lindvall, O. et al. (1994) *Ann. Neurol.* 35:172–180), their precise therapeutic benefit for neural grafting remains unknown. A recent study has demonstrated that 30 mg/kg/d of methylprednisolone enhances graft survival whereas a lower dose of 15 mg/kg/d results in the majority of the grafts being rejected. It is thus possible that the single dose of methylprednisolone employed in this study had relatively potent immunosuppressive activity at the time of grafting which resulted in short-term graft survival and delayed rejection. Alternatively, it has been reported that corticosteroid treatment may reduce graft survival. Patino, P. et al. (1992) *Soc. Neurosci. Abstr.* 18(1-2):59.

Nevertheless, while there was a significant decrease in amphetamine-induced rotation in both the CyA and non-CyA groups 8 weeks after grafting, this effect was not sustained in the non-CyA rats. At the endpoint of the study, the non-CyA group had returned to pre-transplant baseline rotation values. Conversely, at 19 weeks post-transplantation, rotation in the CyA group remained significantly lower than pretransplant values and did not differ from scores seen at 8 weeks post-transplantation. These results demonstrate that under CyA immunosuppression, porcine grafts are able to survive long-term in the adult host brain and mediate sustained functional recovery on amphetamine-induced rotational testing.

Evaluation of TH+ neuron survival as well as graft volume reflect the immunoprotective effects of CyA on neuronal survival. Grafts in the CyA group had significantly greater TH+ neuron survival and greater volume as compared to the non-CyA group.

There was a high degree of correlation between the number of surviving grafted TH+ neurons and the extent of behavioral recovery. Regression analysis revealed a threshold number of approximately 80–100 neurons necessary to obtain at least a 50% reduction in amphetamine-induced rotation. It has been determined that only 3% restoration of striatal dopamine is necessary for recovery on amphetamine-induced rotation (Schmidt, R. H. et al. (1982) *J. Neurochem.* 38:737–748; Schmidt, R. H. et al. (1983) *Acta. Physiol. Scand. Suppl.* 522:19–28).

The histological analysis of surviving grafts in the CyA treated group showed neuron-rich grafts with TH+ cell bodies were located primarily at the graft-host interface, and fibers within the graft and extending throughout the entire grafted striatum. The complete loss of TH+ neurons in the SN associated with the 6-OHDA lesion indicates that these fibers are donor-derived. Similarly, NF70 immunostaining revealed a dense network of fibers and the vast reinnervation capacity of the transplanted porcine neurons. CD44 immunostaining demonstrated glial organization within white matter tracts and fiber extension into the host. In contrast, the majority of grafts in the non-CyA treated rats were small and contained a sparse distribution of neurons. Using a pig-specific DNA marker, the relative extent of donor-derived cells was shown to be dense throughout the graft with some migration of cells into the surrounding striatum as well as the contralateral hemisphere.

EXAMPLE V

Transplantation of Porcine Ventral Mesencephalic and Porcine Striatal Cells into Lesioned Rat Brains and Histological Demonstration of Transplanted Cell Axon Target Specificity Preparation of Cell Suspension for Transplantation and Cell Cultures For striatal tissue cultures, the lateral ganglionic eminence (LGE) (Pakzaban, P. et al. (1993) *Exp. Brain Res.* 97:13–22) from porcine embryos (E35) was dissected, or for substantia nigra cultures, the ventral mesencephalon (E25) was dissected and they were transferred to a Petri dish containing calcium- and magnesium-free Hank's balanced salt solution lacking phenol red (HBSS; Sigma). For preparations of cell suspension for striatal and substantia nigra cultures, LGE and VM tissue fragments, respectively, were pooled from each porcine litter. The tissue fragments were incubated with 1 ml of 0.5% trypsin-0.53 mM EDTA in HBSS (Sigma) at 37° C. for 10 min. The fragments were washed four times with fresh HBSS, then gently triturated through the tips of fire-polished Pasteur pipettes of progressively smaller internal diameter until a milky cell suspension free of visible tissue fragments was obtained. Cell counts and viability were determined by the acridine orange-ethidium bromide method.

For preparations of striatal cultures, dissociated cells were plated on glass coverslips treated with poly-D-lysine (100 $\mu$g ml$^{-1}$) for 30 min in Neuro-C media. The Neuro-C media (a modification of media developed by Coon, H. G. et al. ((1989) *Proc. Natl. Acad. Sci. USA* 86:1703–1707) is formulated with Kaighn's modified Ham's F12 as the basal media with the following supplements added: 15 $\mu$g ml$^{-1}$ ascorbic acid; 0.25% calf serum; 6.25 $\mu$g ml$^{-1}$ insulin; 6.25 $\mu$g ml$^{-1}$ transferrin; 6.25 ng ml$^{-1}$ selenous acid; 1.25 mg ml$^{-1}$ bovine serum albumin (BSA); 5.35 $\mu$g ml-1 linoleic acid; 30 pg ml-1 thyroxine (T3); 3.7 ng ml$^{-1}$ hydrocortisone; 10 ng ml$^{-1}$ somatostatin; 10 ng ml$^{-1}$ Gly-His-Lys (liver cell growth factor); 0.1 $\mu$g ml$^{-1}$ epidermal growth factor (EGF); 50 $\mu$g ml$^{-1}$ bovine pituitary extract (BPE). BPE was prepared according to published methods with frozen bovine pituitary purchased from Neiffenegger (Woodland, Calif.), and all other media additives were purchased from Sigma Chemical Co.

Cells were cultured for several weeks before processing for immunohistochemistry or immunofluorescence. For staining, cells were fixed in 4% paraformaldehyde in calcium- and magnesium-free Dulbecco's PBS (D-PBS) at 37° C. for 15 min. CD-44 antibody clone BAT31A with broad species recognition was purchased from VMRD, Inc. (Pullman, Wash.) and a monoclonal porcine specific antibody to CD44 was also used (clone 10–14, Diacrin, Inc., Charlestown, Mass.). A rabbit anti-GFAP was purchased from Sigma. A monoclonal anti-galactocerebroside antibody (GalC) was purchased from Boehringer Mannheim. A monoclonal antibody directed against bovine 70-kD neurofilament (NF70) was purchased from Biodesign (Kennenbunkport, Me.). Fluorescein-conjugated goat anti-rabbit and rhodamine-conjugated goat anti-mouse antibodies were from Cappel (Durham, N.C.) and a Vectastain Elite ABC peroxidase kit (Vector Laboratories, Burlingame, Calif.) were used fro immunohistochemical staining.

In vivo Transplantation Experimental Design and Treatment Groups

For in vivo reconstruction of the dopaminergic innervation of the striatum in rats with previous selective unilateral lesions of the substantial nigra dopamine neurons porcine ventral mesencephalon (E25) was dissociated into cell suspensions using the same parameters as described for the lateral ganglionic eminence (above). The assess effects of heterotopic and homotopic placements in intact or lesioned areas on glial and axonal growth, embryonic ventral mesencephalic cells were either transplanted into striatal (n=21) or mesencephalic (n=9) sites in rat hosts.

For the in vivo model of striatal neuronal circuitry reconstruction with fetal striatal neural cells, adult male Sprague-Dawley rats (Charles River Laboratories), weighing 300–350 g, received unilateral sterotaxic injections of quinolinic acid into the right neostriatum one week before transplantation. Pakzaban, P. et al. (1993) *Exp. Brain Res.* 97:13–22. The lesioned rats (n=50) were unilaterally transplanted into the striatum with striatal cell suspensions (cell concentration, $50-75 \times 10^3$ cells per microliter) prepared from the LGE as previously described (Pakzaban, P. et al. (1993) *Exp. Brain Res.* 97:13–22; Deacon, T. W. et al. (1994) *Brain Res.* 668:211–219) of the porcine fetal telencephalon. The LGE cell suspension derived from several porcine litters (E35) was transplanted into the rat host striatum (2–3 µl; total cell dose of $150 \times 10^3$ in all animals) in one surgical session.

Immunosuppression

The 80 transplanted rats received systemic immunosuppression by daily subcutaneous injections of cyclosporine A (CsA, 10 mg $kg^{-1}$; Lilly Inc., Indianapolis, Ind.) preoperatively and received tetracycline (Panamycin, 20–40 mg $kg^{-1}$; Sandoz Pharmaceuticals, East Hanover, N.J.). All animals were treated with a single subcutaneous dose of the antibiotic cephalothin (Keflin, 10 mg $kg^{-1}$; Lilly Inc., Indianapolis, Ind.) preoperatively and received tetracycline (Panamycin, 20–40 mg $kg^{-1}$ per day, Upjohn, Kalamazoo, Mich.) in their drinking water (250 mg $l^{-1}$) thereafter. To confirm adequate serum levels of CsA, intracardiac blood from CsA-treated animals (obtained at the time or perfusion) was submitted for measurement of CsA levels by radioimmunoassay (Damon Laboratories, Westwood, Mass.). All animals were perfused with 4% paraformaldehyde 1 to 15 months after transplantation for morphological analysis of the xenotransplants and host brains.

Immunohistochemistry and Microscopy of Neural Transplants

For immunostaining the avidin-biotin-peroxidase method (Vector Laboratories) was applied. Free-floating sections were pretreated with 50% methanol and 3% hydrogen peroxide in PBS for 20 min, rinsed three time in PBS, and incubated in 10% normal horse serum (NHS) in PBS for 60 min before overnight incubation on a moving platform with primary antibody. Primary antibodies and incubation buffers used in this study consisted of a monoclonal antibody to detect porcine CD44 (clone 10–14) diluted 1:2,000 in PBS, a monoclonal antibody to detect the 70-kD neurofilament (NF70) diluted 1:40 in 1% BSA, 1% NHS, and 0.1% Triton X-100 in PBS tyrosine hydroxylase (TH, Pel-Freez, Rogers, Ark.) diluted 1:250. After a 10-min rinse in PBS and two 10-min washes in 5% NHS, sections were incubated in appropriate biotinylated secondary antibody (rat adsorbed, Vector Laboratories) at a dilution of 1:200 in 2% NHS in PBS at room temperature for 60–90 min. The sections were then washed three times in PBS and incubated in avidin-biotin complex (Vectastain ABS Kit ELITE, Vector Laboratories) in PBS for 60–90 min at room temperature. After thorough rinsing with PBS and Tris-buffered saline, sections were developed in 0.04% hydrogen peroxide and 0.05% 3,3'-diaminobenzidine (DAB, Sigma) in Tris-buffered saline.

Controls with omission of the primary antibody were performed on selected sections to verify the specificity of staining. The CD44 and NF70 antibodies bind to pig but not rat tissue and were used as donor-specific markers in pig-to-rat transplants. CD44 and NF70 were used as markers of donor glia and neurons, respectively, as previously described. Pakzaban, P. et al. (1993) *Exp. Brain Res.* 97:13–22; Asher, R. et al. (1992) *Exp. Cell Res.* 203:80–90; Girgrah, N et al. (1991) *J. Neuropath. exp. Neurol.* 50:779–792) Using microscope (Zeiss Axioplan), camera (Panasonic WV-CD) and imaging systems (Adobe Photoshop 2.5 software and Macintosh systems) all sections were evaluated for presence of transplanted embryonic porcine cells. Using species-specific markers, transplant placement was determined by defining transplant boundaries on calibrated image-analysis windows followed by anatomical mapping. Neuronal and glial fibres were traced and mapped using dark-field microscopy. For double-labeling of glial fibers and axons, the sections were first incubated with the anti-CD44 antibody processed with Vector VIP substrate kit (#SK4600), resulting in a violet reaction product. After reincubating the same section with anti-NF70, processing continued with the standard Vectastain (Kit ELITE, Vector Laboratories) with DAB substrate resulting in a brown reaction product. Under light microscopy, the two reaction products were clearly distinct by color.

Growth of Transplanted Porcine Glial and Axonal Fibres

In a series of xenotransplant experiments using neuroblasts from porcine LGE implanted into the rat striatum, cell maturation and fiber growth were analyzed at different time points (1–15 months). At one month postimplantation, $NF70^+$ axons and $CD44^+$ glial fibers were growing into host tissues. By two to four months, extensive $CD44^+$ glial fibre growth was observed in all host white matter tracts near the transplant, and $NF70^+$ growth was also observed in some host white and gray matter structures near the grafts, but axons were not as extensive as glial fibers nor did they extend as far within these tracts. By six months, and at all later time points, $CD44^+$ astroglial somata could be observed in most white matter tracts near the graft site and $CD44^+$ fibres were observed up to 8 mm from the graft. At this stage, $NF70^+$ axons were also observed in host white matter tracts and gray matter target structures that were appropriate to the graft cell types. Later time pinots do not indicate continued axonal growth. Over this time course, transplant cytoarchitecture and immunohistochemical staining also changed to reflect maturational changes that are typical for the normal maturation of pig striatum (or VM). In summary, $CD44^+$ glial fibers show an exuberant nonspecific growth into white matter, whereas axonal growth is more specific and also penetrates into gray matter. Transplant growth is more prolonged than in recent donor grafts but not atypical for pig maturation.

To determine glial and axonal growth patterns of neural transplants in neural circuit reconstruction, an animal model of Parkinson's disease which shows dopamine cell and axon depletion produced by unilateral lesions of the substantia nigra pars compact region was used. Aguayo, A. J. et al. (1984) *Neurosci. Lett.* 45:53–58; Brundin, P. et al. (1985) *Brain Res.* 331:251–259. One to six months after transplantation, on post-mortem analysis, donor embryonic cells derived from pig VM (embryonic day 25 (E25)) were found to grow within the host adult rat striatum under immunosuppression. Fibrous processes from CD44⁺ glial cells from VM grafts were found penetrating myelinated fibre bundles of host striatum. Such CD44⁺ glial cells and fibres always extended into myelinated fibre bundles of the internal capsule from which they also reached a number of host fiber tracts with fibre-lengths of up to several millimeters. Using NF70 staining of VM grafts, projections of non-dopaminergic cells to host target regions located outside striatum were investigated. Axons were seen in great abundance growing inside myelinated fiber tracts of the adult host internal capsule. Some of these non-dopaminergic axons from fetal VM transplants projected selectively to the gray matter of ventral anterior and mediodorsal thalamus. These regions are normally innervated by neurons, located in such VM regions as the substantia nigra pars reticulata and deep mesencephalic nuclei, respectively. The trajectories used by these NF70⁺ porcine axons to reach thalamus were confined to myelinated tracts, such as the internal capsule.

Grafts derived from VM contained a small proportion (approx. 5–10%) of neurons that were dopaminergic, as determined by immunohistochemical staining against tyrosine hydroxylase (TH⁺). From the neuronal core of VM grafts, TH⁺ axons branched for several millimeters directly into the host striatal gray matter between internal capsule myelinated fiber bundles. TH⁺ axons branched profusely in this gray matter target region but only rarely penetrated or crossed white matter tracts. Dopaminergic axons from transplants placed in the rat mesencephalon (either ectopic, dorsal or homotopic ventral nigral placements) were found inside myelinated fiber bundles en route to the striatum where the dopaminergic fibres then branched extensively into host gray matter. As in the case of VM transplants placed in the mesencephalon were also found as distinct fibres or branched morphology growing inside host white matter myelinated fiber bundles, but unlike donor axons, these glial fibers did not penetrate into any gray matter zone.

Double-labelling of Donor Axons and Glial Fibres

In order to unambiguously determine the morphology of donor glia and donor axons, double-labelling with specific antibodies was performed on individual brain sections. Double-labelling showed that glial fibers and axon morphology were very different even when they were growing side by side in the same white matter region. NF70⁺ axons were always distinguishable from CD44⁺ fibres by double-labelling (brown versus purple) and by their distinct morphology. Glial fibers grew nonspecifically into host white matter, but not host gray matter.

CD44⁺ glial fibers always had highly branched processes with characteristic thick and irregular surfaces. In contrast, NF70⁺ axons were always unbranched within white matter, with small caliber processes running separately from CD44⁺ fibers and in parallel with host-myelinated tracts. In gray matter, only NF70⁺ axons were seen. Such axons were sometimes branched. In summary, only donor axons were seen to penetrate into distant gray matter targets, whereas CD44⁺ glial fibres were found in all white tracts extending out from the transplant site, and never in host gray matte outside the transplant itself.

Specific Axonal Penetration into Gray Matter Host Target Zones

Systematic comparison of glial fiber and axonal growth in different host brain regions demonstrates their distinct tropic characteristics. For example, axons from 4-month LGE grafts were found growing inside myelinated internal capsule fiber bundles, where some axons turned directly into the host globus pallidus. These NF70⁺ fibers arborized extensively inside this normal gray matter target zone of the striatum. In comparison, CD44⁺ glial fibers did not grow into this gray matter target zone. Instead, the glial fibers remained within the myelinated fiber tract of the internal capsule projecting in a caudal direction. The same pattern was observed in the entopeduncular nucleus and ventral globus pallidus regions (in the vicinity of medial amygdala). NF70⁺ axonal fibers were seen growing in the internal capsule along with CD44⁺ glial fibers. However, only the NF70⁺ axons were seen penetrating and branching into the rat entopeduncular nucleus and passing into the gray matter of the amygdala whereas the glial processes were confined to white matter tracts in the same plane of section. At the distant striatal target site of the substantia nigra, directed target specific axonal growth into gray matter that was distinct from donor glial processes was also observed. Striatal donor axons penetrated into the gray matter zone of substantia nigra pars reticulata. Although CD44⁺ glial fibers also extended in the cortico-spinal tract along with the NF70⁺ fibers, they did not grow into this midbrain gray matter striatal target zone.

EXAMPLE VI

Transplantation of Rat and Porcine Cortical Cells into Lesioned Rat Brains and Histological Examination of the Transplanted Cells Experimental Animals Thirty-two female Sprague Dawley rats (Charles River Laboratories, Wilmington, Mass.), weighing 200–250 g. at the beginning of the experiment were used in this study. They were housed in groups of 2 to 3 per cage in a colony room under a 12 hour light-dark cycle. These animals were divided into three groups as follows: 12 rats with excitotoxic cortical lesions, 11 rats with lesions plus fetal rat grafts, and 9 rats with lesions plus fetal porcine grafts.

Preparation of Cell Suspensions for Transplantation

Fourteen rat fetuses (crown-to-rump length (CRL) 12–14 mm, estimated 13–14 days gestational age; supplied by Charles River Laboratories) were removed from a timed-mated pregnant Sprague-Dawley rat under terminal pentobarbital anesthesia. Cortical neural tissue was bilaterally dissected from each fetus under 40-fold magnification in sterile phosphate buffered saline (PBS). Eight pig fetuses (CRL 37 mm, estimated 38–39 days gestational age) were removed from a timed-mated pregnant Yorkshire pig following euthanasia according to standard veterinary procedures at Tufts School of Veterinary Medicine (Grafton, Mass.). The uterine horns were transported on ice to a sterile laboratory facility (Diacrin, Inc., Charlestown, Mass.). Uterine pouches were then opened and the fetuses transferred to sterile PBS. Their brains were then removed and the cortical anlage dissected, taking care to remove only presumptive motor/somatosensory cortex and not limbic cortex.

Rat and pig tissues were collected separately in sterile Hank's balanced salts solution (HBSS; Sigma Chemical Co., St. Louis, Mo.). Rat tissue was incubated at 37° C. in 0.1% trypsin for 20 minutes. Pig tissue was incubated at 37° C. in 0.5% trypsin and DNase (80 Kunitz units/ml) for 30 minutes. Both tissues were then washed three times with HBSS, and carefully triturated with a fire-polished Pasteur pipette until homogenous suspensions were obtained. Rat cell viability and concentration was 97% and 30,000 cells/$\mu$l, respectively; and porcine cell viability and concentration was 96% and 18,000 cells/$\mu$l, respectively, as determined by the acridine orange/ethidium bromide exclusion method (Brundin, P. et al. (1985) *Brain Res.* 331:251–259).

Lesion and Transplantation Surgery

All thirty two rats were subjected to quinolinic acid lesions of the right dorsolateral cortex. Following a pretreatment of keflin (10 mg/kg) and atropine (0.1 mg/kg), and under pentobarbital anesthesia (65 mg/kg), each rat was mounted on a Kopf rat stereotactic frame (IB: −3.3) and a midline incision was made through the scalp and periosteum. A burr hole was drilled at coordinates measured from interaural zero as AP +0.5, L −2.4. Injections were made through the burr hole in a rostral direction at an angle of 10° from the horizontal. Using a 5 μl Hamilton syringe, the cortex was horizontally penetrated for 10 mm (measured from the dura), and a total of 5 μl of a 100 mM solution (500 nmoles) of quinolinic acid (Schwartz, R. et al. (1983) Science 219:316–319) in phosphate buffered saline, pH 7.4 (PBS), was infused. The injections were equally distributed among 5 different sites spaced 2 mm apart along the needle tract (see FIG. 18A). At each site, 1 μl of quinolinate was infused over 2 minutes followed by a 1 minute pause. Following needle withdrawal, the retracted skin edges were carefully apposed and sutured.

Figure 18A:
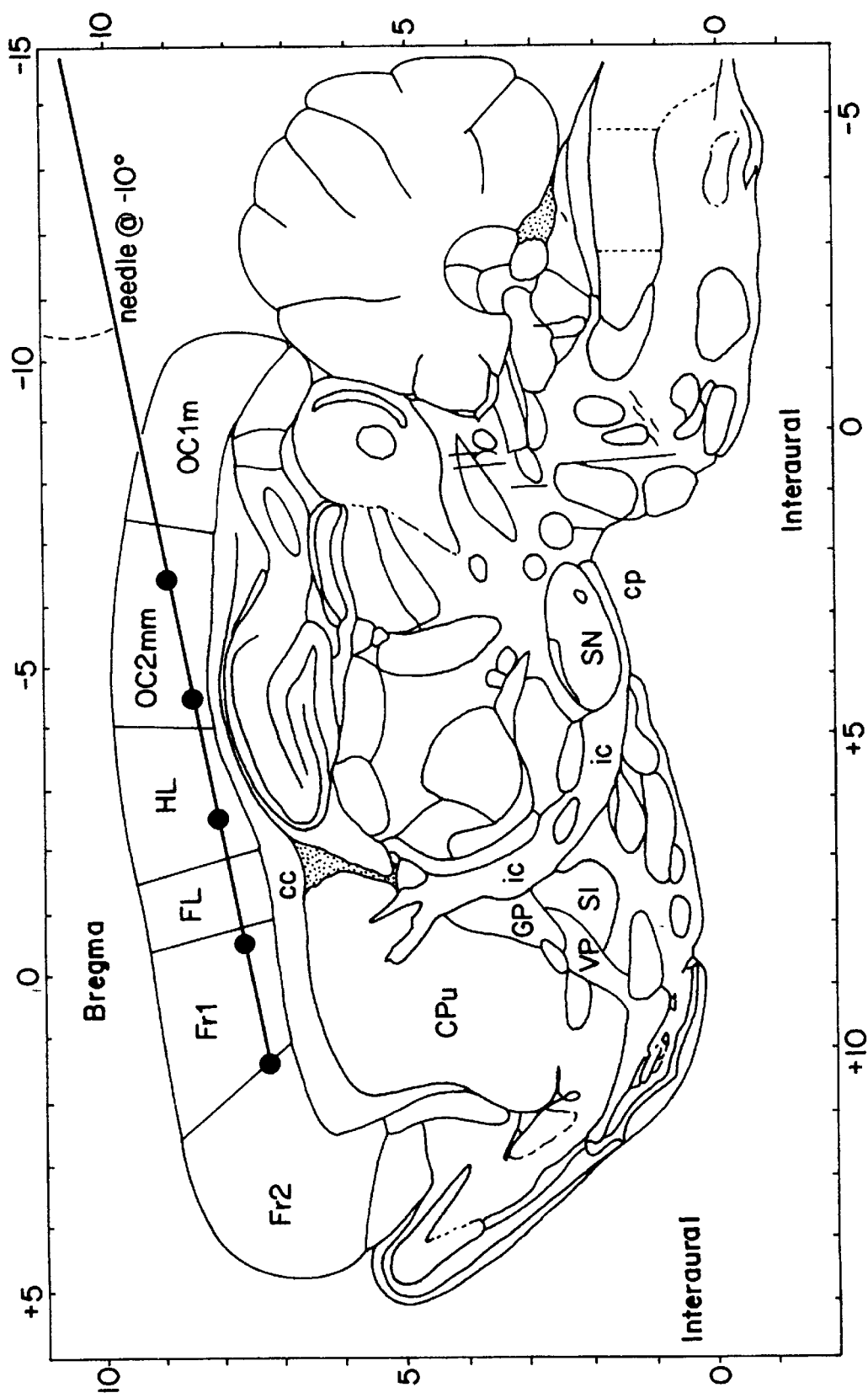
FIGS. 18A–18C are photographs (and a schematic) showing cortical lesions and implantation sites and characteristic cytoarchitecture of lesions and grafts.
Figure 18B:
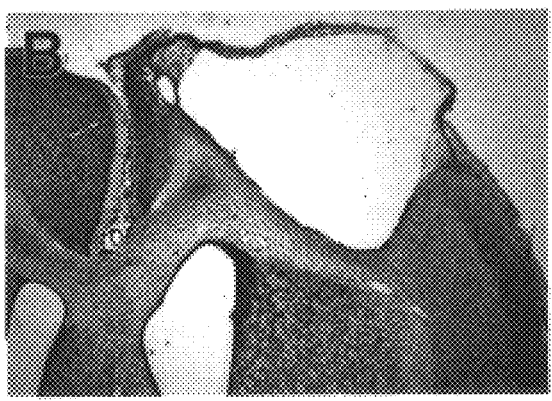
Figure 18C:
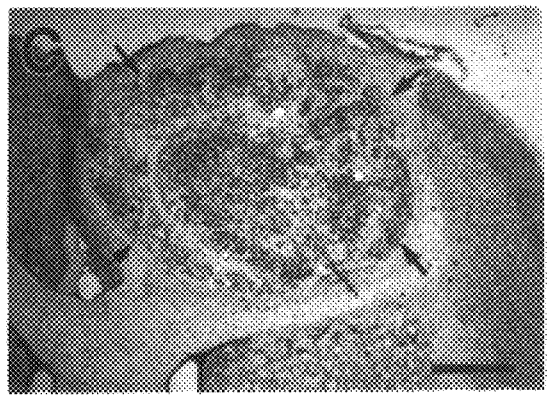

FIGS. 18A–18C show cortical lesion and implantation sites and characteristic cytoarchitecture of lesions and grafts. FIG. 18A depicts a schematic drawing of stereotaxic coordinates and trajectory of lesion and graft site on a redrawn section from the atlas of Paxinos and Watson ((1986) The Rat Brain in Stereotaxic Coordinates. San Diego. Academic Press). Orientation of the needle track is shown by a line with dots to indicate injection sites. FIG. 18B shows a coronal section through a typical cortical lesion showing sparing of pial surface, reduction in the volume of the underlying striatum and ventricular enlargement (8 months after lesion). FIG. 18C shows a coronal section through a typical cortical graft (8 months after lesion and implantation) showing complete filling of the lesion space and the concentric organization of cells within the graft. FIGS. 18B and 18C are enlarged to the same scale and the scale bar in FIG. 18C indicates 500 μm.

The same oblique stereotactic approach was used for transplant surgery as was used for delivery of the excitotoxin. Three days after lesion surgery, eleven rats received a 3.5 μl fetal rat cortical suspension (approximately 100,000 cells) along the lesioned trajectory. Four days post-lesion, nine rats likewise received a 4 μl fetal porcine graft (approximately 90,000 cells). These nine rats were immunosuppressed with daily injections of Cyclosporine A (CsA: 10 mg/kg s.c.; Sandoz Pharmaceuticals, East Hanover, N.J.) beginning on the day prior to transplantation and throughout the duration of the experiment.

Perfusion and Tissue Processing Procedures

Survival time for the allograft and xenograft groups were 31 and 34 weeks respectively. Of the lesion-only group, seven were sacrificed at 31 weeks and 5 were sacrificed at 34 weeks. Under deep pentobarbital anesthesia, each animal underwent intracardiac perfusion with 250 ml of cold heparinized saline (0.1% heparin in 0.9% saline) followed by 200 ml of 4% paraformaldehyde (PFA) in PBS. Brains were removed from all animals and postfixed overnight at 4° C. in 4% PFA in PBS after which they were cryoprotected by equilibration in 30% sucrose in PBS. Brains were then cut either coronally or sagitally on a freezing microtome at a thickness of 40 μm and sections were serially placed in PBS in 6 series.

Nissl Staining and Acetylcholinesterase Histochemistry

For general morphological analyses, one series (every sixth section) from each brain was stained with cresyl violet (Nissl stain) according to the acetate-alcohol method.

To analyze the extent of fiber integration within the graft and between the graft and host cortex, one series from each brain underwent acetylcholinesterase (AChE) histochemistry according to the method of Geneser-Jensen, F. A. and Blackstad, T. W. (1971) Z. Zellforsch 114:460–481. Briefly, sections were slide mounted, dried, and then incubated for 6 h in the incubation solution containing 30 mM sodium acetate buffer, pH 5.0, 0.1 mM ethopropazine, 4 mM acetylthiocholine iodide, 16 mM glycine, and 9 mM copper sulphate. The slides were then rinsed in distilled water, developed in 10% potassium ferricyanide for 90 s, and washed again in distilled water prior to exposure to 0.5% sodium sulfide for 30–40 s.

Immunohistochemistry

To analyze afferent innervation to the grafts, every sixth section from transplanted brains was immunostained for tyrosine hydroxylase (TH), a marker for dopaminergic and noradrenergic fibers from the substantia nigra and locus ceruleus, respectively. In addition, to investigate axon and glial fiber extension from porcine grafts into the rat host, these brains were immunostained with antibodies to proteins expressed in pig but not rat brains. These donor specific proteins are pig cluster of differentiation antigen (CD44), a membrane protein found on porcine astrocytic glial fibers; and bovine neurofilament 70 kD (NF70), a marker for pig axons.

Immunohistochemistry was performed using the avidin-biotin-peroxidase method (Vectastain ABC Kit ELITE; Vector Labs, Burlingame, Calif.). Free floating sections were pretreated with 50% methanol and 3% hydrogen peroxide in PBS for 20 minutes, rinsed 3 times in PBS, and incubated in 10% normal blocking serum (NBS; normal horse serum was used for CD44 and NF70 staining and normal goat serum was used for TH staining) in PBS for 60 minutes prior to overnight incubation on a moving platform with the primary antibody. Primary antibodies and incubation buffers used in this study consisted of a monoclonal antibody raised in mouse to porcine CD44 (clone 10–14; Diacrin, Charlestown, Mass.) diluted 1:2000 in PBS, a monoclonal antibody raised in mouse to detect NF70 (Biodesign, Kennebunkport, Me.) diluted 1:40 in 1% bovine serum albumin, 1% NBS, and 0.1% Triton X-100 in PBS, and a polyclonal antibody raised in rabbit to detect TH (Pel-Freeze Biologicals, Rogers, Ark.) diluted 1:500 in 2% bovine serum albumin, 1% NBS, and 0.1% Triton X-100 in PBS. After a 10 minute rinse in PBS and two 10 minute washes in 5% NBS, sections were incubated in biotinylated horse anti-mouse antibody (for sections stained for CD44 and NF70) or biotinylated goat anti-rabbit antibody (for sections stained for TH) at a dilution of 1:200 in 2% NBS at room temperature for 60 min. The sections were then washed three times in PBS and incubated in avidin-biotin complex in PBS for 90 min at room temperature. Following thorough rinsing in PBS and Tris-buffered saline (TBS), sections were developed in 0.04% hydrogen peroxide and 0.05% 3,3'-diaminobenzidine (DAB; Sigma, St. Louis, Mo.) in TBS.

Tracer Injections

To examine fiber outgrowth from allografts, fluorescent retrograde dyes were injected into subcortical areas which may have been potentially innervated by the cortical allografts. Specifically, 7 days before sacrifice, animals in the allograft protocol (n=11) were anaesthetized and received stereotactically 0.5 μl injections of Fast Blue (3% solution; Sigma, St. Louis, Mo.) and Fluoro-Gold (2.5% solution; Fluorochrome, Englewood, Calif.) into the striatum and cerebral peduncle, respectively, ipsilateral to the grafted cortex. The injections were made at angles through the contralateral hemisphere and into the target sites in order to avoid false labeling from leakage of the dyes into the ipsilateral cortex. Injection coordinates and angles are as follows. Injections of Fast Blue into the striatum were made at coordinates calculated from bregma as L: +5.0 mm, AP: 0, V: −9.0 mm at a lateral injection angle of 65° from the normal. Fluoro-Gold injections into the cerebral peduncle were made at coordinates measured from bregma as L: +3.0 mm, AP: −6.0 mm, V: −9.5 mm at an angle of 30° from the normal.

Morphological Analysis of Cortical Lesions

Examination of cases with cortical lesions alone revealed neuronal loss in a caudo-rostral columnar cavity in the dorsolateral cortex—an area which includes frontal and sensorimotor cortex—while leaving the dura and underlying corpus callosum largely intact (see FIG. 18B). In many cases, striatal shinkage and ventricular expansion ipsilateral to the lesion was also evident. This may have been caused by leakage of quinolinic acid through the corpus callosum and/or by subsequent retrograde degeneration in the striatum caused by the destruction of striatal projection areas in the lesioned cortex.

Histological Analyses of Allografts

All eleven animals in this protocol were found to have surviving grafts, which were clearly demarcated against host tissue. In all but three cases, these grafts filled the entire lesion cavity to an extent roughly equivalent to that of normal cortex (see FIG. 19C).

Figure 19A:
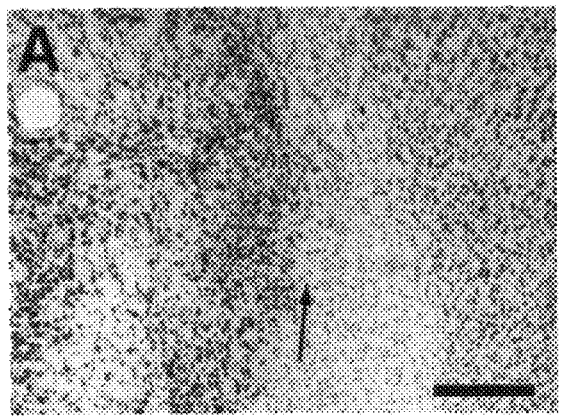
FIGS. 19A–19D are photographs showing the connectivity of graft and host at the graft-host boundary in rat cortical allografts (the graft is to the left of the arrow in each case).
Figure 19B:
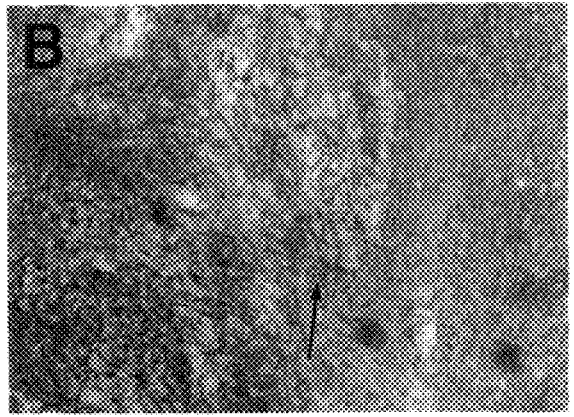
Figure 19C:
Figure 19D:
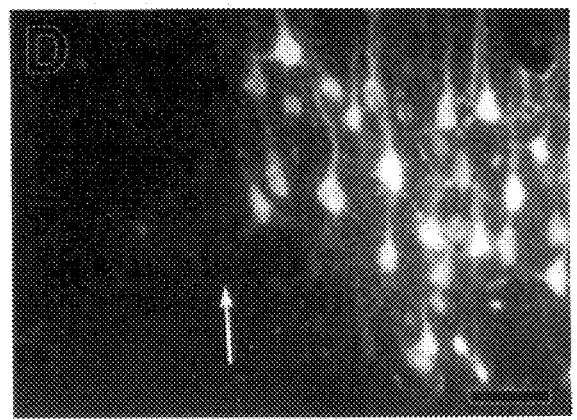

FIGS. 19A–19D show cytoarchitecture and connectivity of graft and host at the graft-host boundary in rat cortical allografts (the graft is to the left of the arrow in each case). FIG. 19A shows Nissl staining of somata showing a cell poor interface and non-laminar arrangement of cells within the graft. FIG. 19B shows acetylcholinesterase histochemical staining showing extensive penetration of AChE-positive fibers into the graft. FIG. 19C shows tyrosine hydroxylase immunohistochemical staining of fibers showing similar density of afferent fibers in graft and host. FIG. 19D shows retrograde labeling of pyramidal cell somata in the host cortex adjacent to the graft but not within the graft after deposition of fluorescent retrograde tracer dyes into the ipsilateral striatum and cerebral peduncle. FIGS. 19A–19C are enlarged to the same scale and the scale bar in A indicates 250 μm. FIG. 19D is enlarged to a higher magnification and the scale bar indicates 50 μm.

In three cases, the graft was thicker than host cortex and displaced the underlying corpus callosum and striatum. Nissl stained sections revealed that the laminar organization characteristic of normal cortex was absent within these grafts. Instead, graft morphology was characterized by neuron-rich regions separated from each other by regions made up largely of white matter (see FIGS. 18C and 19A). These clusters consisted of large pyramidal-like neurons, with small interneurons scattered throughout the graft.

AChE fiber density was slightly lower in the graft than in surrounding host cortex and, again, lacked the normal laminar patterns. However, numerous AChE-positive fibers were observed within the grafts and formed a network which was continuous with the host cortex (see FIG. 19B). A number of TH-positive fibers were found in the grafts which were comparable to those found in intact contralateral cortex. Fluorescent retrograde labeling of neurons from Fast Blue injected into the striatum and Fluoro-Gold injected into the cerebral peduncles was not present within the allografts, although extensive labeling was observed in adjacent host cortex.

Histological Analyses of Xenografts

Of the nine animals in the xenograft protocol, five were found to have surviving grafts. Of these five, two had grafts which completely filled the lesion cavity. Macroscopically, their appearance was very similar to the allografts. The transplants were clearly demarcated from host tissue and also displayed clusters of neurons. AChE and TH fiber distributions were also very similar to those of the allograft group in surviving porcine grafts.

However, with regard to donor efferent outgrowth there were marked differences between allo- and xenografts. FIGS. 20A–20F show axonal and glial fiber outgrowth from porcine cortical xenografts. FIG. 20A shows a parasaggital view of a Nissl-stained rat host brain showing the location and cytoarchitecture of the graft (encircled by arrowheads) and the approximate anatomical locations of the representative photographs (FIG. 20B) that show selected regions that have been differentially immunoreacted for porcine axons using 70 kD neurofilament (NF70); FIGS. 20B–20D) and porcine astro-glial fibers using an antibody to CD44 surface antigen (FIGS. 20E–20F). FIG. 20B shows NF70-positive porcine graft axons (arrows) penetrating the corpus callosum (cc) below the graft site. FIG. 20C show NF70-positive graft axons (arrows) in the gray matter of the host striatum ipsilateral to the graft. FIG. 20D shows NF70-positive graft axons (arrows) growing in a caudo-ventral orientation within the medial forebrain bundle after passing around the genu of the corpus callosum. FIG. 20E shows CD44-positive porcine astro-glial fibers growing within the ipsilateral cerebral peduncle at the level of the substantia nigra. Graft axons were not seen at this level. FIG. 20F shows CD44-positive astro-glial fibers within the internal capsule at the level of the globus pallidus. Images are not to the same scale. Scale bars in FIGS. 20B, 20D, and 20F indicate 50 μm. Scale bars in FIGS. 20C and 20E indicate 100 μm.

Based on NF-70 immunoreactivity, grafts were densely filled with donor derived axons (see FIG. 20A). A significant number of axons crossed the intact corpus callosum to innervate the host dorsal striatum up to 5 mm from the graft (FIG. 20B), but most axons took tangential paths along the dorsal corpus callosum and projected to cortical structures instead of passing into the white matter. Comparatively few axons entered the internal capsule fiber bundles and none were seen more caudal than the striatum (FIG. 20C). One major exception to these short-distance projections was a sizeable projection via the cingulum bundle into the medial forebrain bundle in the basal forebrain (FIG. 20D). These axons followed a circuitous route around the genu of the corpus callosum that is estimated to be at least 10 mm. Donor axonal outgrowth into host cortex and into the contralateral hemisphere via collosal projections were more extensive than previously observed in allograft experiments (Isacson, O. and Sofroneiw, M. V. (1992) *Exp. Neurol.* 117:151–175).

Figures 21A, 21B:
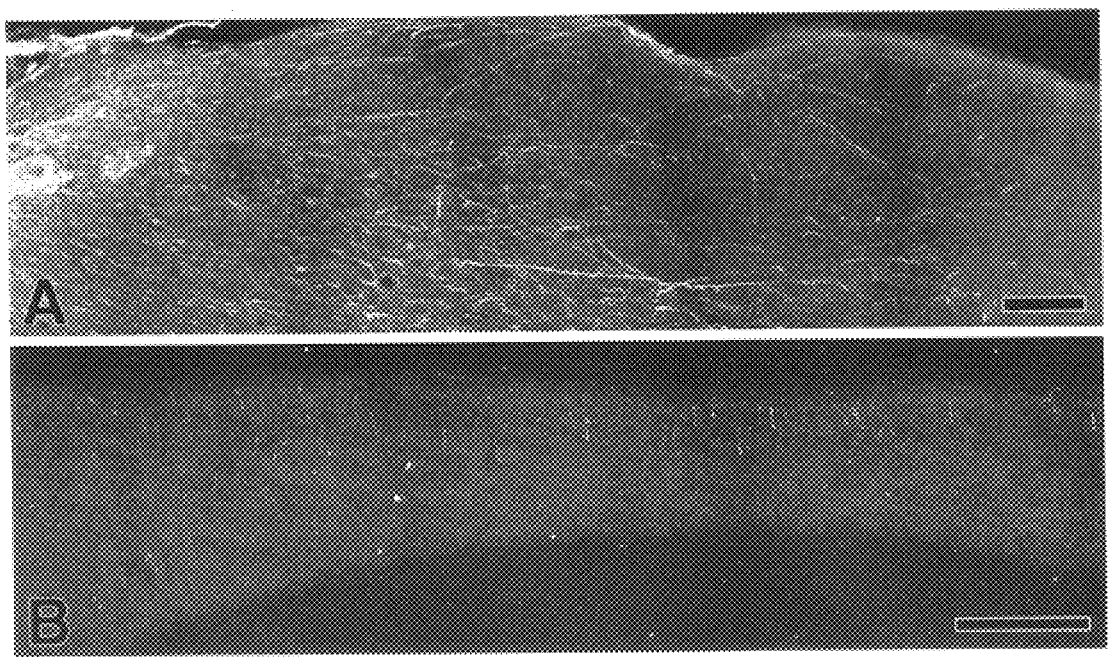
FIGS. 21A–21B are photographs showing NF70-positive porcine graft axons projecting from a cortical graft into the ipsilateral cerebral cortex.
Figure 22A:
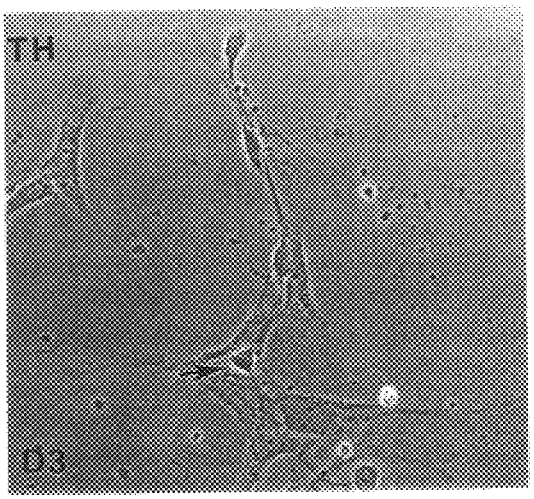
FIG. 22 depicts a set of photographs of phase-fluorescence pairs of representative images of fetal ventral mesencephalic cells from several different isolations. Cells were stained for either a polyclonal rabbit antibody to tyrosine hydroxylase (TH) or a monoclonal mouse antibody to neuron-specific enolase (NSE) and then with fluorescein goat anti-rabbit or goat anti-mouse secondary antibodies, respectively. The antibody used for staining is marked in the upper left for each pair. Typically from 1–5% of the cells stain positive for TH and all cells stain for NSE which is a generalized brain cell specific marker.
Figure 22B:
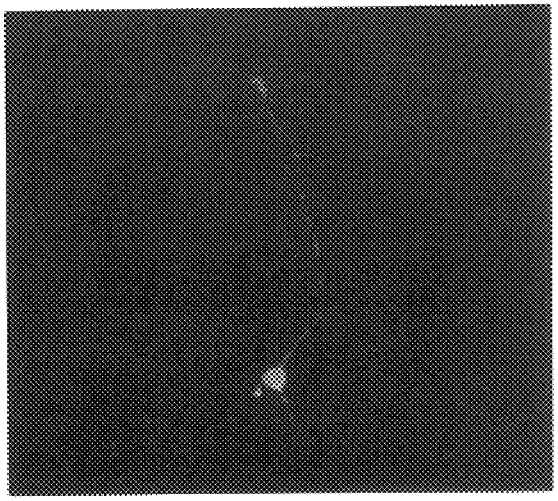
Figure 22C:
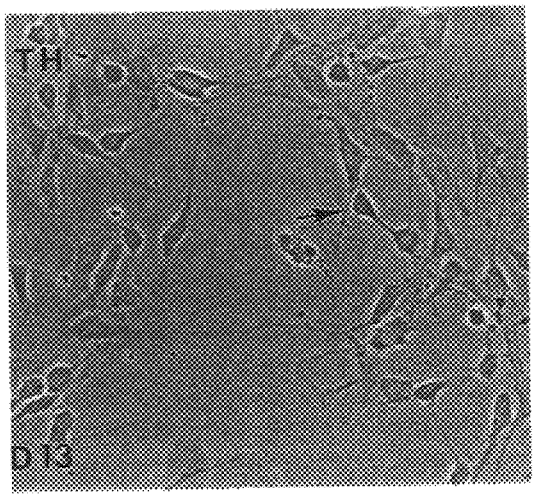
Figure 22D:
Figure 22E:
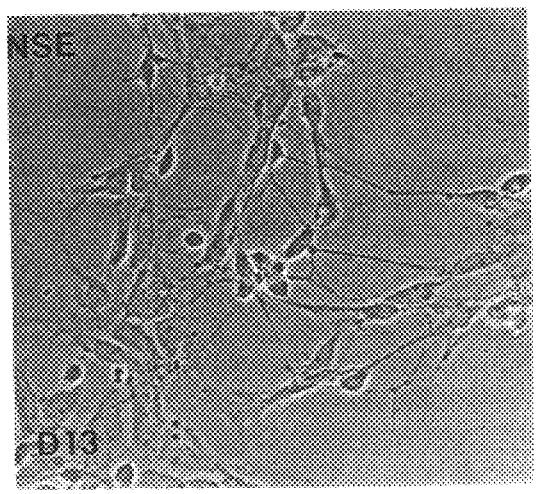
Figure 22F:
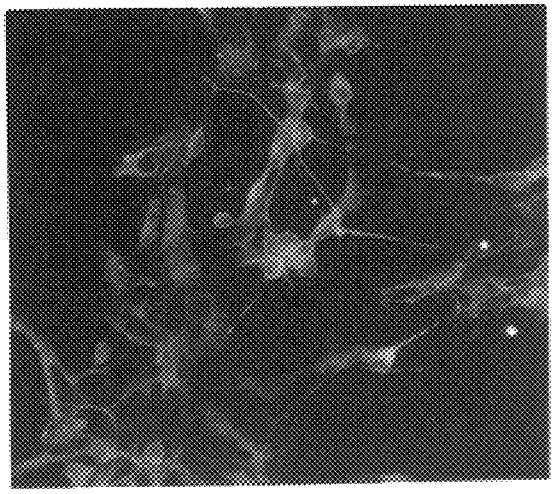

FIGS. 21A–21B show parasaggital sections of NF70-positive porcine graft axons projecting from a cortical graft into the ipsilateral cerebral cortex (FIG. 21A) and the contralateral corpus callosum (FIG. 21B) of the rat host. Specifically, FIG. 21A shows extensive long distance porcine axonal projections from cortical grafts to host cerebral cortex posterior to the graft (the graft is located just beyond the left edge of the photograph). Scale bar indicates 250 μm. FIG. 21B shows graft axons (vertically oriented small white fibers) projecting toward contralateral cortex in the corpus callosum contralateral to the graft. The corpus callosum is visible as a light band oriented left (rostral) to right (caudal). Scale bar indicates 100 µm.

Using a species-specific porcine cell surface astroglial marker (CD-44), long-distance fiber-like extensions in the host brain were also observed. Such donor-derived glial processes were present in many forebrain host white matter tracts. These included the corpus callosum, the cerebral peduncles, the internal capsule, and the cingulum bundle. The donor glial cells and their processes were found oriented in parallel to fiber tracts within host white matter structures such as the internal capsule at the level of the striatum and thalamus (FIG. 20F) and projected as far as the cerebral peduncle (FIG. 20E).

Comparisons Between Allografts & Xenografts: Morphology and Graft-Host Innervation The overall appearance of our cortical allotransplants in the adult rat was consistent with previous studies on cortical neural transplantation (Das, G. D. (1985) "Development of Neocortical Transplants" in "Neural Grafting in the Mammalian CNS (Bjorklund, A. Stenevi, U., eds., Amsterdam, Elsevier) pp. 101–123; Gonzalez, M. F. et al. (1988) *Exp. Neurol.* 99:154–165; Soares, H. and McIntosh, T. K. (1991) *J. Neural. Transplant. & Plast.* 2:207–220, Grabowski, M. et al. (1992) *Exp. Neurol.* 116:105–121; Isacson, O. and Sofroniew, M. V. (1992) *Exp. Neurol.* 117:151–175). While the cortical allografts were able to maintain afferent and intrinsic fiber systems, as evidenced by AChE staining and TH immunohistochemistry, the fluorescent tract tracing results show no evidence of reinnervation of extracortical structures by cortical allografts. These results are consistent with previous studies (Gonzalez, M. F. et al. (1988) *Exp. Neurol.* 99:154–165; Isacson, O. and Sofroniew, M. V. (1992) *Exp. Neurol.* 117:151–175).

In contrast, while the porcine cortical xenografts displayed a similar cytoarchitecture to the allografts they also demonstrated a remarkable ability to extend processes into the adult host. These processes grew across the corpus callosum to the underlying striatum as well as around the genu of the corpus callosum via the cingulum bundle to the medial forebrain bundle in the basal forebrain. Graft-derived glial fibers were able to reach even more distant regions as evidenced by CD-44 immunoreactivity in the internal capsule and cerebral peduncle. This is the first evidence that homotopic fetal cortical grafts in adult brains can extend significant numbers of axons for long distances, innervating noncortical tissues, extending across white matter tracts, and growing within host fiber tracts to subcortical regions. In addition, graft innervation into host cortex, both ipsilaterally and contralaterally, is enhanced by xenografts in comparison to what has previously been reported of allografts (Isacson, O. and Sofroniew, M. V. (1992) *Exp. Neurol.* 117:151–175).

A surprising finding was the long distance projection of glial fibers into the internal capsule and the cerebral peduncle. It is possible that these graft derived glial fibers correspond to radial-like glial fibers within fetal brains. The role of structural glia and radial guide fibers in neuronal migration and axon guidance in developing brains is well documented (Dodd, J. and Jessell, T. M. (1988) *Science* 242:692–699; Silver, J. et al. (1993) *J. Comp. Neurol.* 328:415–436; Steindler, D. A. et al. (1993) *Ann. Rev. Neurosci.* 16:445–456). Since both glioblasts and neuroblasts are included in fetal cortical cell suspensions, it is possible that the growth of graft glial fibers into these tracts offers graft axons a growth promoting substrate that facilitates entry into and growth within an otherwise non-permissive substrate.

EXAMPLE VII

Methods of Detecting Pathogens in Swine

A. Collecting, Processing, and Analyzing Pig Fecal Samples for Signs of Pathogens Feces are extracted from the pig's rectum manually and placed in a sterile container. About a 1.5 cm diameter portion of the specimen was mixed thoroughly in 10 ml of 0.85% saline. The mixture is then strained slowly through a wire mesh strainer into a 15 ml conical centrifuge tube and centrifuged at 650×g for 2 minutes to sediment the remaining fecal material. The supernatant is decanted carefully so as not to dislodge the sediment and 10% buffered formalin was added to the 9 ml mark, followed by thorough mixing. The mixture is allowed to stand for 5 minutes. 4 ml of ethyl acetate is added to the mixture and the mixture is capped and mixed vigorously in an inverted position for 30 seconds. The cap is then removed to allow for ventilation and then replaced. The mixture is centrifuged at 500×g for 1 minute (four layers should result: ethyl acetate, debris plug, formalin and sediment). The debris plug is rimmed using an applicator stick. The top three layers are carefully discarded by pouring them off into a solvent container. The debris attached to the sides of the tube is removed using a cotton applicator swab. The sediment is mixed in either a drop of formalin or the small amount of formalin which remains in the tube after decanting. Two separate drops are placed on a slide to which a drop of Lugol's iodine is added. Both drops are coverslipped and carefully examined for signs of pathogens, e.g., protozoan cysts of trophozoites, helminth eggs and larvae. Protozoan cyst identification is confirmed, when required, by trichrome staining.

B. Co-cultivation Assay for Detecting the Presence of Human and Animal Viruses in Pig Cells Materials Cell Lines African green monkey kidney, (VERO), cell line American Type Culture Collection, (ATCC CCL81), human embryonic lung fibroblasts, (MRC-5) cell line American Type Culture Collection, (ATCC CCL 171), porcine kidney, (PK-15), cell line American Type Culture Collection, (ATCC CRL 33), porcine fetal testis, (ST), cell line American Type Culture Collection, (ATCC CRL 1746)

Medium, Antibiotics, and Other Cells, and Equipment

Fetal calf serum, DMEM, Penicillin 10,000 units/ml, Streptomycin 10 mg/ml, Gentamicin 50 mg/ml, guinea pig erythrocytes, chicken erythrocytes, porcine erythrocytes, Negative Control (sterile cell culture medium), Positive Controls: VERO and MRC-5 Cells: Poliovirus type 1 attenuated, (ATCC VR-1 92) and Measles virus, Edmonston strain, (ATCC VR-24), PK-1 5 and ST Cells: Swine influenza type A, (ATCC VR-99), Porcine Parvovirus, (ATCC VR-742), and Transmissible gastroenteritis of swine, (ATCC VR-743). Equipment: tissue Culture Incubator, Inverted Microscope, Biological Safety Cabinet.

These materials can be used in a co-cultivation assay (a process whereby a test article is inoculated into cell lines (VERO, MRC-5, PK1 5, and ST) capable of detecting a broad range of human, porcine and other animal viruses). Hsuing, G. D., "Points to Consider in the Characterization of Cell Lines Used to Produce Biologicals" in Diagnostic Virology, 1982 (Yale University Press, New Haven, Conn., 1982).

Experimental Design and Methodology

A total of three flasks (T25) of each cell line are inoculated with at least 1 ml of test article. Three flasks of each cell line can also be inoculated with the appropriate sterile cell culture medium as a negative control. Positive control viruses are inoculated into three flasks of each cell line. After an absorption period, the inoculate is removed and all flasks incubated at 35–37° C. for 21 days. All flasks are observed at least three times per week for the development of cytopathic effects, (CPE), of viral origin. Harvests are made from any flasks inoculated with the test article that show viral CPE.

At Day 7 an aliquot of supernatant and cells from the flasks of each test article are collected and at least 1 ml is inoculated into each of three new flasks of each cell line. These subcultures are incubated at 35–37° C. for at least 14 days. All flasks are observed and tested as described above.

At Day 7, the flasks from each test article are also tested for viral hemadsorption, (HAd), using guinea pig, monkey and chicken erythrocytes at 2–8° C. and 35–37° C. at 14 days postinoculation.

At Day 21, if no CPE is noted, an aliquot of supernatant from each flask is collected, pooled, and tested for viral hemagglutination, (HA), using guinea pig, monkey, and chicken erythrocytes at 2–8° C. and 35–37° C. Viral identification is based on characteristic viral cytopathic effects (CPE) and reactivity in HA HAd testing.

The test samples are observed for viral cytopathic effects in the following manner: All cultures are observed for viral CPE at least three times each week for a minimum of 21 days incubation. Cultures are removed from the incubator and observed using an inverted microscope using at least 40× magnification. 100× or 200× magnification is used as appropriate. If any abnormalities in the cell monolayers, including viral CPE, are noted or any test articles cause total destruction of the cell monolayer, supernatant and cells are collected from the flasks and samples are subcultured in additional flasks of the same cell line. Samples can be stored at −60° to −80° C. until subcultured. After 7 and 14 days incubation, two blind passages are made of each test article by collecting supernatant and cells from all flasks inoculated with each sample. Samples can be stored at −60° to −80° C. until subcultured.

Hemadsorbing viruses are detected by the following procedure: after 21 days of incubation, a hemadsorption test is performed to detect the presence of hemadsorbing viruses. Supernatant fluids are collected and pooled from each flask inoculated with test articles or controls. Fluids are tested using guinea pig, monkey, and chicken erythrocytes. Hemagglutination testing is also performed after 21 days of incubation of the subcultures. Viral isolates are identified based on the cell line where growth was noted, the characteristics of the viral CPE, the hemadsorption reaction, and hemagglutination reactions, as appropriate. The test article is considered negative for the presence of a viral agent, if any of the cell lines used in the study demonstrate viral, CPE, HA, or HAd in a valid assay.

C. Procedure for Preparing and Maintaining Cell Lines Used to Detect Viruses in Pig Cells
Materials
Fetal calf serum (FCS), DMEM, Penicillin 10,000 unit/ml, Streptomycin 10 mg/ml, Gentamicin 50 mg/ml, T25 tissue culture flasks, tissue culture incubator (5% $CO_2$, 37° C.)
Procedure
Aseptic techniques are followed when performing inoculations and transfers. All inoculations and transfers are performed in a biological safety cabinet. Media is prepared by adding 10% FCS for initial seeding, 5% FCS for maintenance of cultures, as well as 5.0 ml of penicillin/streptomycin and 0.5 ml of gentamicin per 500 ml media. Sufficient media is added to cover the bottom of a T25 tissue culture flask. The flask is seeded with the desired cell line and incubated at 37° C., 5% $CO_2$ until cells are 80 to 100% confluent. The flasks are then inoculated with virus (QCP25).

D. Preparation of Erythrocyte (rbc) Suspensions Used in Hemadsorption (HAd) and Hemagglutination (HA) Virus Detection Testing
Materials
Phosphate buffered saline, (PBS), pH 7.2, guinea pig erythrocytes stock solution, porcine erythrocytes stock solution, chicken erythrocytes stock solution, sterile, disposable centrifuge tubes, 15 or 50 ml Laboratory centrifuge
Procedure
An appropriate amount of erythrocytes (rbc) is obtained from stock solution. The erythrocytes are washed 3 times with PBS by centrifugation at approximately 1000×g for 10 minutes. A 10% suspension is prepared by adding 9 parts of PBS to each one part of packed erythrocytes. The 10% rcb suspensions are stored at 2–8° C. for no more than one week. 0.5% ecb suspensions are prepared by adding 19 parts of PBS to each one part of 10% rbc suspension. Fresh 0.5% rbc suspensions are prepared prior to each day's testing.
Hemagglutination (HA) Test
A hemagglutination test is a test that detects viruses with the property to agglutinate erythrocytes, such as swine influenza type A, parainfluenza, and encephalomyocarditus viruses, in the test article. Hsuing, G. D. (1982) Diagnostic Virology (Yale University Press, New Haven, Conn.); Stites, Daniel P and Terr, Abba I, (1991), Basic and Clinical Immunology (Appleton & Lange, East Norwalk, Conn.).
Materials
Supernatants from flasks of the VERO cell line, MRC-5 inoculated with the test article, flasks of positive and negative controls, phosphate buffered saline (PBS), pH 7.2, guinea pig erythrocytes (GPRBC), 0.5% suspension in PBS, chicken erythrocytes (CRBC), 0.5% suspension in PBS, porcine erythrocytes (MRBC), 0.5% suspension in PBS
Procedure
All sample collection and testing is performed in an approved biological safety cabinet. 0.5% suspensions of each type of erythrocytes are prepared as described above. The HA test on all cell lines inoculated with samples of the test articles at least 14 days post-inoculation. Positive and negative control cultures are included for each sample and monolayers are examined to ensure that they are intact prior to collecting samples.

At least 1 ml of culture fluid from each flask inoculated with the test article is collected and pooled. 1 ml samples from the negative and positive control cultures are also collected and pooled. A set of tubes is labeled with the sample number and type of erythrocyte (distinguish positive and negative suspension) to be added. Racks may be labeled to differentiate the type of erythrocyte. 0.1 ml of sample is added to each tube. 0.1 ml of the appropriate erythrocyte suspension is added to each tube. Each tube is covered with parafilm and mixed thoroughly. One set of tubes is incubated at 2–8° C. until tight buttons form in the negative control in about 30–60 minutes. Another set of tubes is incubated at 35–37° C. until tight buttons form in the negative control in about 30–60 minutes.

Formation of a tight button of erythrocytes indicates a negative result. A coating of the bottom of the tube with the erythrocytes indicates a positive result.

E. Methods Used for Fluorescent Antibody Stain of Cell Suspensions Obtained from Flasks Used in Detection of Viruses in Porcine Cells Using Cell Culture Techniques (as Described in Sections B and C)

Materials

Pseudorabies, parvovirus, enterovirus. adenovirus, transmissible Gastroenteritis Virus. bovine viral diarrhea, encephalomyocarditus virus, parainfluenza, vesicular stomatitis virus., microscope slides, PBS, incubator with humidifying chamber at 36° C., Evan's blue coutner stain, DI Water, fluorescent microscope, trypsin, serum containing media, acetone, T25 Flask.

Procedure

Cells (described in Sections B and C) are trypsinized to detach them from the T25 flask and sufficient media is added to neutralize trypsin activity. A drop of cell suspension is placed on each microscope slide and allowed to air dry. A slide for each fluorescent antibody is prepared. Cells are fixed by immersion in acetone for five minutes. Each fluorescent antibody solution is placed on each slide to cover cells and the slides are incubated in humidifying chamber in incubator at 36° C. for 30 minutes. The slides are then washed in PBS for five minutes. The wash is repeated in fresh PBS for five minutes followed by a rinse with DI water.

The cells are counterstained by placing Evan's blue solution on each slide to cover cells for five minutes at room temperature. The slides are then washed in PBS for five minutes. The wash is repeated in fresh PBS for five minutes followed by a rinse with DI water. The slides are then allowed to air dry. Each slide is inspected under a fluorescent microscope. Any fluorescent inclusion bodies characteristic of infection are considered a positive result for the presence of virus.

F. Procedures for Defining Bacteremic Pigs

Materials

Anaerobic BMB agar (5% sheep blood, vitamin K and hemin [BMB/blood]), chocolate Agar with Iso Vitalex, Sabaroud dextrose agar/Emmons, 70% isopropyl alcohol swabs, betadine solution, 5% $CO_2$ incubator at 35–37° C., anaerobic blood agar plate, gram stain reagents (Columbia Broth Media), aerobic blood culture media (anaerobic brain heart infusion with vitamin K & hemin), septicheck media system, vitek bacterial identification system, laminar flow hood, microscope, and bacteroids and Bacillus stocks.

Procedure

Under a laminar flow hood, disinfect the tops of bottles for aerobic and anaerobic blood cultures of blood obtained from pig with 70% isopropyl alcohol, then with betadine The rubber stopper and cap from the aerobic blood culture bottle are removed and a renal septicheck media system is attached to the bottle. The bottles are incubated in 5% $CO_2$ for 21 days at 35–37° C., and observed daily for any signs of bacterial growth (i.e. gas bubbles, turbidity, discoloration or discrete clumps). Negative controls consisting of 5 cc of sterile saline in each bottle and positive controls consisting of *Bacillus subtilis* in the aerobic bottle and Bacteriodes Vulgaris in the anaerobic bottle are used. If signs of bacterial growth are observed, a Gram stain is prepared and viewed microscopically at 100× oil immersion for the presence of any bacteria or fungi. The positive bottles are then subcultured onto both chocolate agar plates with Iso Vitlex and onto BMB plates. The chocolate plate is incubated at 35–37° C. in 5% $CO_2$ for 24 hours and the BMB anaerobically at 35–37° C. for 48 hours. Any yeast or fungi that is in evidence at gram stain is subcultured onto a Sabaroud dextrose/Emmons plate. The Vitek automated system is used to identify bacteria and yeast. Fungi are identified via their macroscopic and microscopic characteristic. If no signs of growth are observed at the end of 21 days, gram stain is prepared and observed microscopically for the presence of bacteria and fungi.

Absence of growth in the negative control bottles and presence of growth in the positive control bottles indicates a valid test. The absence of any signs of growth in both the aerobic and anaerobic blood culture bottles, as well as no organisms seen on gram stain indicates a negative blood culture. The presence and identification of microorganism(s) in either the aerobic or anaerobic blood culture bottle indicates of a positive blood culture; this typicall is due to a bacteremic state.

EXAMPLE VIII

Protocol for Transplantation of Porcine Neural Cells into Patients with Parkinson's Disease A. Protocol Patient Inclusion Criteria All human patients selected for this study have advanced Parkinson's disease of 7 to 20 years duration. In all patients, medical therapy has failed or begun to fail with signs of severe bradykinesia, dyskinesia and marked on/off phenoma. The Core Assessment Program for Intracerebral Transplantation (CAPIT) was used to evaluate patients. CAPIT is consensus criteria for inclusion of patients in a transplantation trial and their subsequent evaluation. The core inclusion criteria are based on clinical diagnostic criteria and L-dopa responsiveness. Diagnosis of Parkinson's disease must be clearly established according to recognized signs and symptoms of the disease. Parkinsonism must be idiopathic in nature and not due to tumors, infection, cerebrovascular disease or trauma.

Parkinsonism must be idiopathic as determined by exhibiting two of the following: 1) bradykinesia, 2) tremors, 3) rigidity or 4) postural instability, at least one of which is either tremor or bradykinesia. Patients must be unequivocally responsive to L-dopa therapy by showing a 33% improvement in their Unified Parkinson's Disease Rating Scale (UPDRS) score over that measured in their worst off as defined in CAPIT. Patients must have intractable symptoms despite optimal drug therapy including frequent Off episodes, disabling dyskinesias or freezing while On. Patients must also be Magnetic Resonance Imaging (MRI) negative.

Patient Exclusion Criteria

Patients are excluded based on diagnosis of secondary Parkinson's as indicated by Parkinson "Plus" syndromes. Patients with a mini-mental state score of 22 or less (maximum=30) will be excluded to eliminate dementia, since dementia could indicate the presence of an accompanying Alzheimer disease or diffuse Lewy body disease, and dementia would interfere with tolerance to medication or the ability of the examiners to adequately test the subject. Patients with a Hamilton Depression Scale score of 20 or more points will be excluded to eliminate patients with major depression, since depression could interfere with obtaining accurate UPDRS scores and global rating results. Patients are also excluded based on the presence of significant medical disease which could interfere with any long term follow-up and evaluation.

Evaluation of Patient Parkinsonism

Baseline—Core Evaluation

Patients are evaluated by using the UPDRS as a primary clinical assessment scale. Ratings will be also be established according to Hoehn and Yahr Staging and Dyskinesia Rating Scale evaluation systems per CAPIT.

Evaluations are complemented by timed tests of motor function including; pronation-supination test, hand/arm movement between two points, finger dexterity and stand-walk-sit test. Pharmacologic testing is done as a single dose L-dopa test in defined Off state as defined in CAPIT. Patients and their families keep a daily diary for one week prior to each evaluation session and each of the sessions are video taped. MRI is performed and Positron Emission Tomography (PET) scans are done.

Because of the day-to-day variability in Parkinson's disease, patients are evaluated over a 1–3 month period to establish a reliable base-line clinical status. There will be one to three separate evaluations including all day observations. During the evaluation period, patients medication should be kept constant. The actual number of months of valuation and observation will be dependent upon how long the individual patient has already been followed at Lahey Clinic prior to their entry to this study.

Post-operative Evaluations

Patients are followed for three years post-operatively with Core Evaluations conducted every three months. Follow-up PET scans are conducted at 6–8 months and between year 2 and year 3 post operatively.

The pre and post operative videotapes are rated by independent examiners. The examiners are blinded to the time and taping of the patients in relation to surgery.

Type, Number and Concentration of Cells to be Implanted

Fetal mesencephalic cell suspensions are prepared from dissection of the rostral half of the ventral mesencephalon of porcine embryonic tissue from E26–28 aged fetuses. Time-mated, ultrasound confirmed pregnant Yorkshire pigs are euthanized according to the standard veterinary procedures at Tufts University School of Veterinary Medicine (North Grafton, Mass.). The ventral mesencephalon from the fetuses are carefully dissected under microscopic guidance, then pooled, incubated and trypsinized to prepare a cell suspension for transplantation. Cells are prepared at a concentration of 50,000 cells per microliter and are assessed for viability. Up to forty microliter volumes of cell suspension at each of the six stereotaxic targets in the putamen on one side are implanted. Thus up to a total of 240 $\mu$l is injected. It has been found in rat experiments that 10% of the cells survive after implantation. Therefore, up to $12 \times 10^6$ cells are injected, to yield approximately $12 \times 10^5$ surviving cells of which about 10% have been found to be mesencephalic dopaminergic cells (Brundin, P., et al. (1985) *Brain Res.* 331:251–259; Dunnett, S. B. (1994) "Improving Viability of Nigral Grafts in Transplantation in Neurodegenerative Disease" 5th *International Symposium of Neural Transplantation* Chatery-Malabry, Paris. AGON. S. 27). Consequently, $12 \times 10^4$ cells are replaced. In advanced Parkinson's disease, patients have lost at least 80–90% of $25 \times 10^4$ dopaminergic cells normally providing dopamine to the putamen.

Implantation Sites and Procedure

Two sites in the anterior putamen and four in the posterior putamen are targeted for transplantation of porcine neural cells. All patients undergo unilateral stereotaxic implantation of cells using MRI guided technique. The CRW stereotaxic frame is utilized for this procedure. This apparatus is routinely used for precise targeting of structures in the brain for biopsies or functional ablation therapy. The cannula to be used was developed at Diacrin, Inc., Charlestown, Mass. and was manufactured by the Radionics Company in Burlington, Mass. The outer diameter of the cannula is 1.0 mm and the inner dimension is 0.5 mm. A micromanipulator apparatus is used in conjunction with the stereotaxic frame localizer. The patient is taken to the MRI Scanner where a study is performed to target specific locations in the putamen. The patient is then taken to the operating room and under sterile conditions, a 3 cm incision is made in the right front scalp. A burr hole is made in the calvarium, 2 cm lateral to the midline and 1 cm anterior to the coronal suture. The meninges are opened with a coagulator to allow safe and smooth penetration of the catheter. The catheter is placed to targets in the putamen as previously calculated. The patient is awake during the entire procedure and receives only subcutaneous lidocaine in the scalp and some mild intravenous sedation. Since there are no pain receptors in the brain, the passage of the catheter and the grafting procedure is painless. At the end of the grafting procedure, the incision is closed with nylon sutures, a sterile dressing is applied and the stereotaxic frame is removed. The patient is taken to the recovery room and observed closely for 24 hours. The patient is allowed to eat and resume normal activities on the first postoperative day. If the patient is in good condition 2 days after the operation they are discharged with close follow-up.

Immunosuppression

Patients are given cyclosporine orally. The major adverse reactions of cyclosporine therapy are increased risk of infection, renal dysfunction, hypertension, hirsutism and gum hyperplasia. The first dose of cyclosporine is given 12 hours prior to transplantation as a single dose of 15 mg/kg. A daily dose of 14 to 18 mg/kg is used. Two weeks after surgery, cyclosporine is tapered off by 5% per week to a maintenance dose of 5–10 mg/kg. Blood cyclosporine levels are monitored and frequent tests of hematologic and renal function are undertaken in each patient and corrections in dosage are made accordingly.

C. Evaluation Protocol

Evaluation of Parkinsonism

Patients are evaluated for degree of Parkinsonism as previously described. In that this safety study, patients are be primarily monitored for untoward side effects of the implanted cells.

Laboratory Tests

Liver and kidney function are assessed regularly by serum creatinine, BUN, liver enzymes, serum bilirubin, complete blood count and platelet function, electrolytes and cyclosporine levels.

MRI Scan

Each patient undergo a pre and postoperative MRI scan. The MRI scan is performed within 3 months prior to surgery and again seven days after surgical implantation of cells. A follow-up MRI again is undertaken at six months.

PET Imaging with 6-[$^{10}$F] Flouro-L-Dopa (FD)

Preoperative PET scanning are performed within a three month period prior to implantation and again at nine and eighteen months postoperatively. The patients are fasted overnight and all antiparkinsonian medications are withheld for 12 hours prior to PET imaging. PET studies are performed with a PC-4096 scanner (Scanditronix A B, Sweden). The performance characteristics of this instrument are well-described in the literature (Roto Kops, F. et al. (1990) *J. Comput. Assist. Tomogr.* 14:(3):437–445). The primary imaging parameters of the PC-4096 camera are in-plane and axial resolutions of 6.0 mm FWHM, 15 contiguous slices of 6.5 mm separation and a sensitivity of=5.000 cps/$\mu$Ci. All images are reconstructed using a conventional tiltered back-projection algorithm to an in-plane resolution of 7 mm FWHM. Attenuation corrections are performed from transmission data acquired using a rotating pin source containing $^{68}$GE. FD is prepared by the procedure described by Luxen (Luxen, A. et al. (1990) *Appl Radiat Isot,* 41:275–281); radiochemical purity>95% specific activity=400 mCi/mmole.

Patients are positioned in the scanner in individually fabricated head holders (Tru Scan Image Inc., Annapolis, Md.) with laser alignment. The gantry angle is adjusted to be parallel to the orbitomeatal line. All studies are performed with eyes open in a dimly illuminated room and minimal auditory stimulation.

Carbidopa (200 mg) is given orally 1 hour before each tracer injection to inhibit decarboxylation; FD (5–10 mCi) is injected intravenously as a bolus at the start of imaging. Twelve 10 minute, sequential emission scans are acquired starting immediately after injection.

Whole blood samples (1 ml) are drawn from a radial artery catheter as follows: 8 during the first minute beginning during the tracer injection; 4 samples during the next minute; 1 sample at 3, 4, 5, 7, 12 and 17 minutes; and 1 sample every 10 minutes from 25 to 115 minutes. The blood is centrifuged and total plasma radioactivity is determined on 0.5 ml samples. Plasma metabolites of FD (3-0-methyl-FD) are measured from 5 ml samples drawn at 2.5, 5, 7, 10, 15, 20, 30, 45, 60, 75, 90 and 120 minutes by a batch contact alumina extraction method (Chan, G. et al. (1991) *Life Sci.* 50:309–318).

Data Analysis

The images acquired from 60 to 120 minutes after FD injection are be summed to produce a high count density integral image. Regions of interest (ROI's) are be drawn on this image as follows: One circular ROI (8 MM diameter) is positioned by inspection on each caudate nucleus and adjusted on the integral image to maximize average ROI activity. Three circular ROI's (8 mm diameter) is placed along the axis of each putamen and adjusted similarly. Three background circular ROI's (20 mm diameter) are placed on each side of the temporo-parietal cortex. This procedure is repeated for all slices where the caudate and putamen are clearly seen. The complete set of ROI's is then be replicated over all time frames. For each frame, the ROI's of like structures are averaged to yield separate measurements for the right and left caudate, right and left putamen and background. The same set of ROI's is used to analyze each scan for a single subject. When necessary, locations are adjusted to compensate for repositioning.

Corrections for FD and 3-0-methyl-FD in the striatal time activity data are performed by subtracting the background from the striatal activity (Martin, W. R. W. et al. (1989) *Ann Neurol* 26:535–542). The rate constant for striatal accumulation of FD is calculated by the graphical method described by Pallak and colleagues (Martin, W. R. W. et al. (1989) *Ann Neurol* 26:535–542; Patlak, C. S. et al. (1983) *J. Cereb Blood Flow Metab.* 3:1–7; Patlak, C. S. et al. (1985) *J. Cereb Blood Flow Metab.* 5:584–590). This analysis is performed for all ROI's on the data acquired from 20 to 120 minutes after injection. The scans are also analyzed as the ratio of target-to-background (ratio method) on the integral image. After correction for area of the ROI's, the striatal activity is divided by the background activity.

Equivalents

Those skilled in the art will recognize, or be able to ascertain using no more than routine experimentation, many equivalents of the specific embodiments of the invention described herein. Such equivalents are intended to be encompassed by the following claims.

What is claimed is:

1. An isoloated porcine cerebral cortical cell, dissociated from porcine cerebral cortex which, in unmodified form, has at least one antigen on the cell surface which is capable of stimulating an immune response against the cell in a xenogeneic subject, wherein the antigen on the cell surface is altered to inhibit rejection of the cell when introduced into the xenogeneic subject.

2. The porcine cerebral cortical cell of claim 1, wherein the antigen on the cell surface which is altered is an MHC class I antigen.

3. The porcine cerebral cortical cell of claim 2, which is contacted prior to transplantation into a xenogeneic subject with at least one anti-MHC class I antibody, or fragment or derivative thereof, which binds to the MHC class I antigen on the cell surface but does not activate complement or induce lysis of the cell.

4. The porcine cerebral cortical cell of claim 3, wherein the anti-MHC class I antibody is an anti-MHC class I F(ab')$_2$ fragment.

5. The porcine cerebral cortical cell of claim 4, wherein the anti-MHC class I F(ab')$_2$ fragment is a F(ab')$_2$ fragment of a monoclonal antibody PT85.

6. The porcine cerebral cortical cell of claim 1, wherein the xenogeneic subject is a human.

7. The porcine cerebral cortical cell of claim 1, which is an embryonic cortical cell.

8. The porcine cerebral cortical cell of claim 7, which is obtained from basal forebrain.

9. The porcine cerebral cortical cell of claim 7, which is obtained from an embryonic pig between about days 27 and 50 of gestation.

10. The porcine cerebral cortical cell of claim 9, which is obtained from an embryonic pig between about days 27 and 40 of gestation.

11. An isolated porcine cerebral cortical cell, dissociated from porcine cerebral cortex having an antibody, antibody fragment or derivative, bound to its surface.

12. The porcine cerebral cortical cell of claim 11, wherein the antibody is an anti-MHC class I antibody.

13. The porcine cerebral cortical cell of claim 12, wherein the anti-MHC class I antibody is an anti-MHC class I F(ab')$_2$ fragment.

14. The porcine cerebral cortical cell of claim 13, wherein the anti-MHC class I F(ab')$_2$ fragment is a F(ab')$_2$ fragment of a monoclonal antibody PT85.

15. An isolated porcine cerebral cortical cell, dissociated from fetal cerebral cortex obtained from an embryonic pig between about days 27 and 40 of gestation, the cortical cell having an antibody bound to an antigen on its surface.

16. A composition for use in transplantation consisting essentially of porcine cerebral cortical cells dissociated from porcine cerebral cortex and an agent or factor selected from the group consisting of: an angiogenic factor, a neurotrophic factor, an antiapoptotic factor, an antioxidant, and an agent which inhibits nitric oxide production.

17. The composition of claim 16, wherein the angiogenic factor is selected from the group consisting of: vascular endothelial growth factor, platelet-derived growth factor, fibroblast growth factor, and epidermal growth factor.

18. The composition of claim 16, wherein the neurotrophic factor is selected from the group consisting of: glial cell line-derived growth factor, brain-derived neurotrophic factor, ciliary neurotrophic factor, midkine, insulin-like growth factor I, insulin like growth factor II, insulin, fibroblast growth factor, neurotrophin-3, neurotrophin 4/5, transforming growth factor β, FK506, and cyclosporine A.

19. The composition of claim 16, wherein the antiapoptotic factor is selected from the group consisting of: the bcl-2 gene product, the bcl-xL gene product, the bcl-Xβ gene product, the crmA gene product, nerve growth factor, platelet-derived growth factor, superoxide dismutase, catalase, and N-acetyl cysteine.

20. The composition of claim 16, wherein the antioxidant is selected from the group consisting of: superoxide dismutase, glutathione peroxidase, N-acetyl cysteine, a lazaroid, vitamin C, vitamin E, and beta carotene.

21. The composition of claim 16, wherein the agent which inhibits nitric oxide production is selected from the group consisting of: gangliosides, FK506, cyclosporine A, and superoxide dismutase.

22. An isolated population of porcine cerebral cortical cells, dissociated from porcine cerebral cortex which, in unmodified form, have at least one antigen on the cell surface which is capable of stimulating an immune response against the cell in a xenogeneic subject, wherein the antigen on the cell surface is altered to inhibit rejection of the cell when introduced into the xenogeneic subject.

23. The population of cells of claim 22, wherein the antigen on the cell surface which is altered is an MHC class I antigen.

24. The population of cells claim 23, which is contacted prior to transplantation into a xenogeneic subject with at least one anti-MHC class I antibody, or fragment or derivative thereof, which binds to the MHC class I antigen on the cell surface but does not activate complement or induce lysis of the cell.

25. The population of cells of claim 22, comprising embryonic porcine cortical cells.

26. The population of cells of claim 25, which is obtained from an embryonic pig between about days 27 and 50 of gestation.

27. The population of cells of claim 26, which is obtained from an embryonic pig between about days 27 and 40 of gestation.

* * * * *

UNITED STATES PATENT AND TRADEMARK OFFICE
CERTIFICATE OF CORRECTION

PATENT NO. : 6,140,116
DATED : October 31, 2000
INVENTOR(S) : Jonathan Dinsmore

It is certified that error appears in the above-identified patent and that said Letters Patent is hereby corrected as shown below:

Clerical Error(s):

On page 1, in the section entitled: "Related Applications", the continuing data should be corrected to: This application is a continuation-in-part application of U.S. Serial No. 08/424,856, filed april 19, 1995, which is a continuation-in-part application of U.S. Serial No. 08/336,856, filed November 8, 1994, abandoned. The contents of these applications are hereby incorporated by reference.

Signed and Sealed this

Nineteenth Day of June, 2001

*Attest:*

NICHOLAS P. GODICI
*Attesting Officer*   *Acting Director of the United States Patent and Trademark Office*